(12) United States Patent
Kompella et al.

(10) Patent No.: US 8,821,943 B2
(45) Date of Patent: Sep. 2, 2014

(54) METHODS AND COMPOSITIONS FOR TARGETED DELIVERY OF THERAPEUTIC AGENTS

(75) Inventors: Uday Bhaskar Kompella, Omaha, NE (US); Swita Raghava Singh, Omaha, NE (US); Sneha Sundaram, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1701 days.

(21) Appl. No.: 11/854,209

(22) Filed: Sep. 12, 2007

(65) Prior Publication Data

US 2009/0087494 A1    Apr. 2, 2009

Related U.S. Application Data

(60) Provisional application No. 60/844,037, filed on Sep. 12, 2006.

(51) Int. Cl.
*A61K 9/16* (2006.01)
*A61K 31/7088* (2006.01)
*A61K 39/395* (2006.01)
*A61K 38/16* (2006.01)

(52) U.S. Cl.
USPC ........ 424/499; 424/130.1; 424/489; 435/455; 514/44; 514/12

(58) Field of Classification Search
None
See application file for complete search history.

(56) References Cited

U.S. PATENT DOCUMENTS

| | | | |
|---|---|---|---|
| 5,393,527 A | 2/1995 | Malick et al. | |
| 5,534,496 A | 7/1996 | Lee et al. | |
| 5,635,383 A | 6/1997 | Wu et al. | |
| 5,785,969 A | 7/1998 | Magdassi et al. | |
| 5,972,707 A | 10/1999 | Roy et al. | |
| 6,063,400 A | 5/2000 | Geho et al. | |
| 6,153,587 A * | 11/2000 | Delansorne et al. | 514/15 |
| 6,254,890 B1 | 7/2001 | Hirosue et al. | |
| 6,288,040 B1 | 9/2001 | Mueller et al. | |
| 6,372,250 B1 | 4/2002 | Pardridge | |
| 6,410,517 B1 | 6/2002 | Truong et al. | |
| 6,652,873 B2 | 11/2003 | Deaver et al. | |
| 7,060,291 B1 | 6/2006 | Meers et al. | |
| 7,090,864 B2 | 8/2006 | Pardridge | |
| 7,132,404 B2 | 11/2006 | Goomer | |
| 2003/0044407 A1* | 3/2003 | Chang et al. | 424/130.1 |
| 2005/0255152 A1 | 11/2005 | Edwards et al. | |
| 2006/0073182 A1* | 4/2006 | Wong et al. | 424/426 |

FOREIGN PATENT DOCUMENTS

WO    2005/072710 A2    8/2005

OTHER PUBLICATIONS

Gomes dos Santos et al in "Sustained release of nanosized complexes of polyethylenimine and anti-TGF-beta2 oligonucleotide improves the outcome of glaucoma surgery" (Journal of Controlled Release, 2006, vol. 112, pp. 369-381, available online Mar. 6, 2006).*
Kompella et al (Investigative Ophthalmology & Visual Science, 2003, vol. 44, No. 3, pp. 1192-1201).*
Aukunuru, J.V. et al., "Nanoparticle Formulation Enhances the Delivery and Activity of a Vascular Endothelial Growth Factor Antisense Oligonucleotide in Human Retinal Pigment Epithelial Cells," Journal of Pharmacy and Pharmacology, 2003, 55: 1199-1206.
Suzuki, S. et al., "Modulation of Doxorubicin Resistance in a Doxorubicin-Resistant Human Leukaemia Cell by an Immunoliposome Targeting Transferring Receptor," British Journal of Cancer (1997) 76(a), pp. 83-89.
Koushik, K. et al., "Preparation of Large Porous Deslorelin-PLGA Microparticles with Reduced Residual Solvent and Cellular Uptake Using a Supercritical Carbon Dioxide Process," Pharmaceutical Research, vol. 21, No. 3, Mar. 2004, pp. 524-535.
Kompella, U.B. et al., "Luteinizing Hormone-Releasign Hormone Agonist and Transferrin Functionalizations Enhance Nanoparticle Delivery in a Novel Bovine Ex Vivo Eye Model," Moleculor Vision 2006: 12: 1185-98.

* cited by examiner

Primary Examiner — Catherine Hibbert
(74) Attorney, Agent, or Firm — Edell, Shapiro & Finnan, LLC

(57) ABSTRACT

Compositions and methods for targeted delivery of therapeutic agents, and particularly for mucosal, oral, nasal, or parenteral delivery of therapeutic agents. The compositions comprise carrier particles containing or encapsulating a therapeutic agent or agents, which have been modified on their surface to contain one or more targeting moieties that enable the enhanced uptake and transport of the therapeutic agent via receptor-mediated processes such as endocytosis or transcytosis.

22 Claims, 27 Drawing Sheets

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID (pGlu)
<220> FEATURE:
<221> NAME/KEY: MISC_FEATURE
<222> LOCATION: (6)..(6)
<223> OTHER INFORMATION: Xaa at position 6 is a D-amino acid residue
<220> FEATURE:
<221> NAME/KEY: MOD_RES
<222> LOCATION: (10)..(10)
<223> OTHER INFORMATION: Pro at position 10 is prolyl N-ethylamide
      residue

<400> SEQUENCE: 1

Glu His Trp Ser Tyr Xaa Trp Leu Arg Pro
1               5                   10
```

```
<210> SEQ ID NO 2
<211> LENGTH: 21
<212> TYPE: DNA
<213> ORGANISM: Artificial
<220> FEATURE:
<223> OTHER INFORMATION: Artificial primer sequence

<400> SEQUENCE: 2
gaccttgtct gggaaagatc c                                              21

<210> SEQ ID NO 3
<211> LENGTH: 20
<212> TYPE: DNA
<213> ORGANISM: Artificial
<220> FEATURE:
<223> OTHER INFORMATION: Artificial primer sequence

<400> SEQUENCE: 3
caggctgatc accaccatca                                                20

<210> SEQ ID NO 4
<211> LENGTH: 20
<212> TYPE: DNA
<213> ORGANISM: Artificial
<220> FEATURE:
<223> OTHER INFORMATION: Artificial primer sequence

<400> SEQUENCE: 4
aggaaccgag tctccagtga                                                20

<210> SEQ ID NO 5
<211> LENGTH: 20
<212> TYPE: DNA
<213> ORGANISM: Artificial
<220> FEATURE:
<223> OTHER INFORMATION: Artificial primer sequence

<400> SEQUENCE: 5
atcaactatg atcaccgagt                                                20

<210> SEQ ID NO 6
<211> LENGTH: 21
<212> TYPE: DNA
<213> ORGANISM: Artificial
<220> FEATURE:
<223> OTHER INFORMATION: Artificial primer sequence

<400> SEQUENCE: 6
gtggtcagtt gaggatgtca a                                              21

<210> SEQ ID NO 7
<211> LENGTH: 28
<212> TYPE: DNA
<213> ORGANISM: Artificial
<220> FEATURE:
<223> OTHER INFORMATION: Artificial primer sequence

<400> SEQUENCE: 7
ccacacgtgg tccagcttct ggcgggag                                       28

<210> SEQ ID NO 8
<211> LENGTH: 21
<212> TYPE: DNA
<213> ORGANISM: Artificial
<220> FEATURE:
<223> OTHER INFORMATION: Artificial primer sequence
```

```
<400> SEQUENCE: 8
gatatggctc atgtggtgtt g                                              21

<210> SEQ ID NO 9
<211> LENGTH: 20
<212> TYPE: DNA
<213> ORGANISM: Artificial
<220> FEATURE:
<223> OTHER INFORMATION: Artificial primer sequence

<400> SEQUENCE: 9
aatcttcttc agtcgctcca                                                20

<210> SEQ ID NO 10
<211> LENGTH: 20
<212> TYPE: DNA
<213> ORGANISM: Artificial
<220> FEATURE:
<223> OTHER INFORMATION: Artificial primer sequence

<400> SEQUENCE: 10
gaccttgtct ggaaagatcc                                                20
```

METHODS AND COMPOSITIONS FOR TARGETED DELIVERY OF THERAPEUTIC AGENTS

CROSS REFERENCE TO RELATED APPLICATIONS

The present invention claims priority to U.S. Provisional Patent Application No. 60/844,037, filed Sep. 12, 2006, which is incorporated herein by reference in its entirety.

STATEMENT REGARDING FEDERALLY-SPONSORED RESEARCH

This work was made with government support under Grant Nos. DK064172 and EY013842 awarded by The National Institutes of Health. The government has certain rights in the invention.

COPYRIGHT STATEMENT

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

This invention relates to the prophylactic and therapeutic treatment of disorders using targeted delivery of therapeutic agents, and more particularly to the prophylactic and therapeutic treatment of disorders associated with the eye or nasal tissues.

2. Description of the Background Art

Drug delivery takes a variety of forms, depending on the agent to be delivered and the administration route. The most convenient way to administer drugs in the body is by oral administration, however many drugs, in particular proteins and peptides, are poorly absorbed and unstable during passage through the GI tract. Further, oral delivery is ineffective for treating many disorders of the eye, the brain, and other tissues, due to the presence of barriers such as the blood-retinal barrier, and the blood-brain barrier, which limit the passage of most agents. Oral delivery also results in high systemic levels, thus potentially leading to systemic side effects.

Targeted drug delivery means are increasingly desirable, because they minimize toxic side effects, lower the required dosage amounts, localize drug release and delivery, and decrease costs for the patient. Targeted drug delivery is particularly advantageous for administration methods that are not particularly effective, or that result in poor bioavailability, for example topical administration to the mucosal, ocular, or nasal tissues. In particular, targeted drug delivery provides a non-invasive method of delivering drugs to a tissue to be treated, as well as enabling patients to self-administer medication. Targeted drug delivery also enables the potential of remotely administering medicine, for example nasally administering a targeted compound to treat a disorder of the reproductive system or remote cancers.

Topical treatment of ophthalmic disorders is preferred in many cases because a topical composition may be self-administered by a patient, and does not require the co-administration of anesthetics. Topical compositions are generally ineffective at delivering a therapeutically effective amount of an active ingredient to the anterior and posterior segments of the eye, however, due to short residence time and inadequate penetration. For example, the secretion and drainage of the lacrimal fluid bring about a rapid elimination of conventional dosage forms administered to the eye. For example, only about 50% of an instilled drop remains about 1 minute after administration, and the remainder is rapidly cleared within the next 5 minutes. Due to this brief contact time, only a small fraction of a drug is able to enter the eye tissue, and then cross through the conjunctiva, cornea, and sclera to reach intraocular tissues. Moreover, even if a drug is able to penetrate through some layers of tissue, many drugs do not possess requisite penetration ability with regard to some other tissues of the eye such that an effective dose can be imparted.

The nasal administration route has emerged in recent years as convenient for the delivery of drugs, particularly peptide and protein drugs that have poor oral availability, for example, calcitonin, buserelin, and nafarelin. Because the nasal route is non-invasive and makes self-medication practical, it improves patient compliance when compared with the parenteral route. However, proteins and peptide intra-nasal delivery is considerably less effective than the parenteral route, and the bioavailability is often less than 5%. This poor bioavailability is due in part to pre-systemic elimination due to enzymatic degradation and poor mucosal membrane permeability. Further, some medications administered in the olfactory region are able to access parts of the brain without entering the blood stream, and thus nasal administration can be a direct pathway for brain delivery of drugs. However, the efficiency and the extent of drug absorption using conventional nasal to brain delivery means is low.

Pulmonary delivery is desirable for delivery of protein and peptide drugs, because the large absorptive surface area of the lungs (140 $m^2$ vs 180 $cm^2$ for the nasal route) promotes high absorption. For example, the bioavailability of leuprolide is 2.9% when administered as a nasal solution, but 28% when administered as a suspension aerosol. However, there are several barriers in the lungs that must be overcome before a drug can reach systemic circulation. First, the bioavailability is limited by the maximum deposition of drugs in the alveolar region with the existing devices, which is about 30%. In addition, degradation of peptides in the lungs by alveolar macrophages, epithelial cells, and secreted proteolytic enzymes in the alveolar fluids limit peptide delivery via the lungs. Poor membrane permeability is also a major barrier. These problems have not been overcome by particulate delivery systems, which tend to make engulfment by macrophages (and expulsion from the lungs) more efficient.

What is needed is an improved delivery vehicle for targeting therapeutic agents that overcomes these tissue permeability difficulties, and results in increased uptake and transport of drugs across tissue, particularly mucosal tissues including ocular and nasal tissues. Also needed are methods of targeting the delivery of a therapeutically effective amount of a therapeutic agent, for prophylactic, therapeutic, and diagnostic purposes.

SUMMARY OF THE INVENTION

The present invention relates to compositions for targeted delivery of therapeutic agents, and particularly to such compositions for mucosal, oral, nasal, or pulmonary delivery of therapeutic agents. In particular, the present invention relates to carrier particles containing or encapsulating a therapeutic agent or agents, which have been modified on their surface to contain one or more targeting moieties that enable the enhanced uptake and transport of the therapeutic agent via receptor-mediated processes such as endocytosis or transcytosis.

Particularly provided compositions are those where the targeting moieties are LHRH-receptor-targeting moieties, transferrin-receptor-targeting moieties, or a combination of both, and compositions for administration by nasal, pulmonary, or injection means. Also provided are compositions where the carrier particles are nanoparticles, or the carrier particles are selected from the group consisting of poly(lactide-co-glycolide), poly(lactide), poly ε-caprolactone, albumin, and chitosan. Further provided compositions are those in which the therapeutic agent is an anti-VEGF agent, a glaucoma therapeutic agent, a dry eye therapeutic agent, an antibiotic, an anti-inflammatory, a nucleic acid based therapeutic agent, or a combination of two or more therapeutic agents.

The present invention also provides methods for treating disorders in a mammal in need of such treatment, or preventing disorders in a mammal susceptible to developing such disorders, comprising administering a composition capable of delivering a therapeutically effective amount of a therapeutic agent, wherein the composition comprises a plurality of carrier particles comprising a therapeutic agent and a plurality of targeting moieties conjugated to said carrier particles, and wherein said administration is ocular, nasal, pulmonary, or mucosal.

The present invention further provides methods for treating ophthalmic disorders in a mammal in need of such treatment, or preventing ophthalmic disorders in a mammal susceptible to developing such disorders, comprising administering to the eye a composition capable of delivering a therapeutically effective amount of a therapeutic agent, wherein the composition comprises a plurality of carrier particles comprising a therapeutic agent and a plurality of targeting moieties conjugated to said carrier particles.

The present invention also provides compositions for use in treating or preventing disorders in a mammal comprising a plurality of carrier particles comprising a therapeutic agent and a plurality of targeting moieties conjugated to said carrier particles, wherein the compositions are capable of delivering a therapeutically effective amount of the therapeutic agent. Further provided are ophthalmic compositions for use in treating or preventing ophthalmic disorders, e.g., of the anterior segment, posterior segment, or both, of the eye, which comprise a plurality of carrier particles comprising a therapeutic agent and a plurality of targeting moieties conjugated to said carrier particles.

Further provided are methods where the administration is topical administration, nasal administration, pulmonary administration, administration by injection, and administration to the brain via the nose. Also provided are methods of treating disorders of the anterior segment of the eye, such as dry eye, glaucoma, inflammatory conditions of the anterior segment, and infectious conditions of the anterior segment, and disorders of the posterior segment of the eye, such as macular degeneration, diabetic retinopathy, inflammatory conditions of the posterior segment, infectious conditions of the posterior segment, and vascular disease of the posterior segment.

The present invention further provides a composition for use in treating or preventing disorders in a mammal, comprising: a plurality of carrier nanoparticles comprising a therapeutically effective amount of a therapeutic agent; and means for targeting said nanoparticles to a tissue receptor, as well as methods using these compositions in the treatment and prevention of diseases and disorders, including ophthalmic disorders, neural and brain disorders, tumors and cancers, and the like.

Additional advantages and features of the present invention will be apparent from the following detailed description, drawings and examples, which illustrate preferred embodiments of the invention.

BRIEF DESCRIPTION OF THE DRAWINGS

FIG. 27 depicts uptake in bovine cornea, and FIG. 28 depicts uptake in bovine conjunctiva.

FIG. 45: PC-3 cells).

FIG. 48); inferior turbinate posterior (ITP; FIG. 49); and medium turbinate anterior (MTA; FIG. 50).

DETAILED DESCRIPTION

Figure 1:
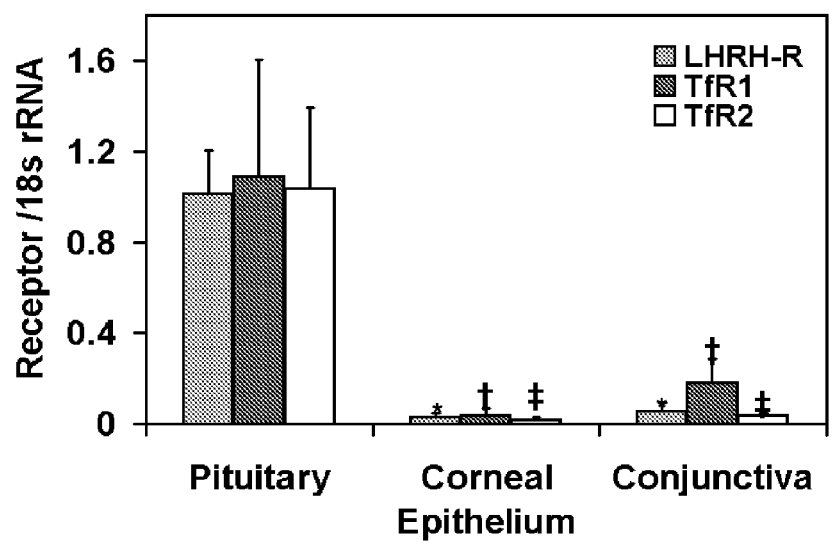
FIG. 1 depicts the expression (mRNA) levels of receptors for LHRH and transferrins in bovine ocular tissue.

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

One skilled in the art may refer to general reference texts for detailed descriptions of known techniques discussed herein or equivalent techniques. These texts include Current Protocols in Molecular Biology (Ausubel et al., eds., John Wiley & Sons, N.Y., and supplements through July 2007), Current Protocols in Immunology (Coligan et al., eds., John Wiley & Sons, N.Y., and supplements through August 2007), Current Protocols in Pharmacology (Enna et al., eds., John Wiley & Sons, N.Y., and supplements through June 2007), The Pharmacological Basis of Therapeutics (Goodman & Gilman, 11$^{th}$ ed., 2006), Remington: The Science and Practice of Pharmacy (Lippincott Williams & Wilkins, 21st edition (2005)), Biomedical Aspects of Drug Targeting (Muzykantov & Torchilin, eds., Springer (2003)), Ophthalmic Drug Delivery Systems (AK Mitra, ed., Informa Healthcare, 2$^{nd}$ ed. (2003)), Principles and Practice of Ophthalmology (Albert and Jakobiec eds., 2d. ed., W.B. Saunders Company (1999)), and Enhancement in Drug Delivery (Touitou & Barry, eds., CRC Press (2006)) for example.

The present invention concerns methods and compositions for the prophylactic and therapeutic treatment of disorders using targeted delivery of therapeutic agents, and more particularly to the prophylactic and therapeutic treatment of disorders by administering compositions containing targeted carrier particles to the eye, nose, and mucosal tissue. The carrier particles are conjugated to a targeting moiety designed to interact with a receptor known to be in the tissue being treated, or a tissue through which the therapeutic agent must travel in order to reach the tissue being treated, e.g., the corneal epithelium or the blood-brain barrier. The compositions and the methods employing them have been found to unexpectedly deliver therapeutically effective amounts of the therapeutic agent when administered to an animal model. The therapeutic agent is transported through the tissue via active transport, that is, receptor-mediated endocytosis and transcytosis.

The targeted carrier particles are useful for enhancing cellular uptake of poorly permeable therapeutic agents, reducing cellular and tissue clearance of therapeutic agents, and sustaining therapeutic agent delivery, particularly in the hard-to-treat ocular tissues. Although it is known that use of appropriately sized nanoparticles can somewhat improve residence and uptake of therapeutic agents in the eye, particularly in the retinal pigment epithelium (RPE), they have been relatively ineffective in improving delivery to other epithelial tissues such as the cornea and conjunctiva. However, as shown in the Examples herein, the targeted carrier particles of the present invention exhibit unexpectedly significant enhancement of residence, uptake and transport times as compared to both known particle delivery systems and conventional delivery of non-particulate therapeutic agents, particularly in the hard to treat ocular epithelial tissues such as cornea and conjunctiva. The advantages of the targeted carrier particles are particularly beneficial for the delivery of macromolecular agents such as peptides, proteins, and nucleic acid based therapeutic agents, and for treatment of chronic conditions such as glaucoma, diabetic retinopathy and age related macular degeneration.

A. LHRH and Transferrin Receptors

As a mechanism for targeting the carrier particles of the invention, the expression of receptors that mediate endocytosis and transcytosis was examined in ocular and nasal tissues. In particular, it was determined for the first time that receptors for Luteinizing Hormone-Releasing Hormone ("LHRH"), also known as gonadotrophin releasing hormone ("GnRH") were present in bovine corneal epithelium and conjunctiva. It was also confirmed that receptors for transferrin (type 1) were present in corneal epithelium, and that LHRH receptors are present in nasal tissue. The findings that nasal tissue expressed LHRH receptors are important, in that it was previously thought that nasal absorption of small peptide drugs occurred by passive paracellular permeability. Nasal tissue was also found to differentially express LHRH receptor, in the order MTA<MTP<ITP.

LHRH receptors are G-protein-coupled receptors expressed primarily in pituitary, reproductive tissues including ovary, testes, and prostate, and liver, heart, skeletal muscle, kidney and placenta. There are two isoforms of LHRH receptors-I and II, however II is inactive in human and bovine tissues. It was previously determined that LHRH receptors are also expressed in bovine nasal tissue, rat trachea, and rat lungs, as well as human bronchial epithelial cells (Calu-3 cells). Koushik et al. (2004) Pharm. Research 21(6): 1034-1046. LHRH receptors are also overexpressed in certain tumors of the breast, ovary, endometrium and prostate, which has led to the development of chemotherapy drugs conjugated to LHRH agonists in order to facilitate intracellular accumulation of the chemotherapy drugs in tumor tissue. Volker et al. (2002) Am. J. Obstet. Gynecol. 186:171-179; Arencibia et al. (2002) Anticancer Drugs 13:949-956.

LHRH agonists trigger an endocytotic process in which LHRH-receptor-agonist complexes are surrounded by clathrin-coated vesicles, which then bud from the plasma membrane and travel into the cell as clathrin-coated endosomes. Subsequently, the receptor is recycled to the plasma membrane for re-use. Part of the endosomes containing the ligand or receptor-agonist complex reach the basolateral surface, leading to the transcytosis of LHRH agonists. This is similar to the transcellular transport processes reported to occur in endothelial cells for gonadotropins, lutropin (luteinizing hormone) and chorionic gonadotropin in endothelial cells. Ginea & Milgrom (2001) Semin. Reprod. Med. 19:97-101. It has been previously shown that LHRH agonists such as deslorelin can be internalized and transcytosed across cell monolayers and epithelial tissues. Koushik et al. (2004) Pharm. Res. 21(6):1034-46; Koushik et al. (2004) J. Pharm. Pharmacol. 56(7):861-8.

The N-terminal (pGlu1-His2-Trp3) and the C-terminal (Pro9-Gly10-NH2) of LHRH are important for receptor binding and activation. Both domains are involved in receptor binding, but the residues in the N-terminal are predominantly responsible for receptor activation. Arg8 is required for high-affinity binding to the mammalian receptor, and substitutions at the sixth position with D-amino acids having bulky hydrophobic side chains, particularly aromatics, result in increased binding affinity and activity. Also, a type II β-turn conformation, which is important for receptor binding, has been identified in the middle region (residues 5-8) of LHRH structure. This conformation may be the reason D-amino acid substitutions, which stabilize the β-turn, result in high receptor binding affinities for deslorelin and buserelin, both analogs of LHRH.

The transferrins are a family of nonheme iron-binding proteins found in vertebrates, including serum transferrins, lacto transferrins (lactoferrins), ovotransferrins, and melanotransferrins. Transferrins play a variety of biological roles, primarily in the transport of iron and other metal ions into tissues and cells, but also potentially in immune and inflammatory responses. Serum transferrin is a glycoprotein with a molecular weight of about 80 kDa, comprising a single polypeptide chain with two N-linked polysaccharide chains that are branched and terminate in multiple antennae, each with terminal sialic acid residues. There are two main domains, the N domain of about 330 amino acids, and the C domain of about 340 amino acids, each of which is divided into two subdomains, N1 and N2, and C1 and C2. Receptor binding of transferrin occurs through the C domain, regardless of glycosylation. Lactoferrin is an iron-binding protein having antibacterial, antiviral, antineoplastic and anti-inflammatory activity, which has high sequence homology with serum transferrin. Melanotransferrin is a glycosylated protein possessing high sequence homology with human serum transferrin, human lactoferrin, and chicken transferrin. Two forms exist—one is bound to cell membranes by a glycosyl phosphatidylinositol anchor while the other form is soluble and actively secreted.

At least two transferrin receptors are known in humans: transferrin receptor 1 (TfR1) and transferrin receptor 2 (TfR2). TfR1 is known to be expressed in a variety of cells such as red blood cells, monocytes, hepatocytes, intestinal cells, and erythroid cells, and is upregulated in rapidly dividing cells such as tumor cells (non small cell lung cancer, colon cancer, and leukemia) as well as in tissue affected by disorders such as acute respiratory distress syndrome (ARDS). TfR2 is primarily expressed in liver and erythroid cells, is found to a lesser extent in lung, spleen and muscle, and has a 45% identity and 66% similarity with TfR1. TfR1 is a transmembrane receptor that forms a homodimer of 760 residues with disulfide bonds and a molecular weight of 90 kDa. Affinity for transferrin varies between the two receptor types, with the affinity for TfR1 being at least 25-30 fold higher than that of TfR2.

The transferrin receptors mediate an endocytotic transport process across the cell membrane, which is understood to occur as follows: a transferrin-iron complex binds to the receptor, triggering the formation of clathrin-coated vesicles surrounding the receptor, which then bud from the plasma membrane and travel into the cell as clathrin-coated endosomes. Upon maturation of the endosomes, the clathrin coat is lost, and the pH of the endosomal compartment is rapidly acidified, releasing the iron from the transferrin. The iron is then transported out of the endosome into the cytosol, the transferrin-bound receptor is transported back to the cell surface through exocytic vesicles, and the transferrin dissociates from the receptor so that both the transferrin and receptor can be re-used. This process is described by Z M Qian et al. (2002) Pharmacol Rev. 54(4):561-87. Transferrin receptors are also involved in iron transport across the blood-brain barrier, but this process is not well understood. It is believed that the transferrin receptors enable the cerebral endothelial cells to uptake iron, but it is not known how iron crosses the abluminal membrane. It has been suggested that iron is transported across the blood-brain barrier by receptor-mediated transcystosis, but this has not been clarified. T Moos & E H Morgan (1998) J. Neurosci. Res. 54:486-494.

The discovery of LHRH receptors in ocular tissue, and the confirmation that transferrin receptors are present at least in corneal epithelium enables the targeting of carrier particles by using these receptors to facilitate active transport of therapeutic agents into the ocular tissue.

B. Carrier Particle Compositions

The carrier particles used in the compositions of the present invention can be based on any biologically suitable material and may take a variety of forms, such as biodegradable particles, liposomes, microspheres, nanoparticles, microbubbles, polymersomes, polyplexes, and synthetic secretory granules. Preferred carrier particles include nanoparticles, which herein refers to particles of the nanometer range (i.e., less than 1 nm in diameter up to several microns in diameter) that are free from gas and thereby distinguishable from the micro- or nano-bubbles of the type described in U.S. Pat. No. 5,215,680.

All types of materials and structures, including inorganic and organic materials, can be used for the carrier particles of the present invention. Non-limiting examples of these materials and structures include polyesters (such as poly(lactic acid), poly(L-lysine), poly(glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), copolymers of these monomers and the like), poly(anhydride-co-imides), poly(amides), poly(orthoesters), poly(phosphoesters), poly(iminocarbonates), poly(urethanes), poly(phosphazenes), poly(organophosphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, copolymers, polystyrene, and blends or co-polymers thereof. In certain preferred aspects, the carrier particles include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. and their derivatives, co-polymers, and mixtures thereof.

In a preferred embodiment, nanoparticles may be formed from compatible polymers and biomaterials such as poly(lactide-co-glycolide) (PLGA), poly(lactide) (PLA), poly ε-caprolactone, albumin, and chitosan. In preferred embodiments, the carrier particles are formed from the biodegradable polymers PLGA or PLA. PLGA and PLA are able to control the release of bioactive macromolecules (e.g., therapeutic agents). PLGA is a well-studied polymer for drug delivery and is FDA-approved for a number of in vivo applications. PLGA degradation times can be varied from days to years by altering the type of polymer, the polymer molecular weight, or the structure of the nanospheres. Further, modifying the end groups of PLGA with acid groups (COOH) allows for greater conjugation of peptide or protein molecules thereby allowing the nanoparticles to be targeted to specific cell types.

In certain embodiments, the carrier particles are associated with a therapeutic agent (e.g., the therapeutic agent is entangled, embedded, incorporated, encapsulated, bound to the surface, or otherwise associated with the carrier particle). In certain embodiments, the therapeutic agent is a drug such as a pure drug (e.g., drugs processed by crystallization or supercritical fluids), an encapsulated drug (e.g., polymers), a surface associated drug (e.g., drugs that are adsorbed or bound to the carrier particle surface), a complexed drug (e.g., drugs that are associated with the material used to form the carrier particle). In a different embodiment, the carrier particles exhibit fluorescent activity or a measurable signal when exposed to light or another external stimulus, which is useful for diagnostics, imaging and sensing.

The carrier particles of the present invention, in certain embodiments, do not include a functional group. In other aspects, however, the carrier particles can include a functional group such as, for example, a carboxyl, sulfhydryl, hydroxyl, or amino group, or any other functional group that can be used to bind a targeting moiety or moieties to the surface of the carrier particles.

The carrier particles may be formed by suitable means known in the art, for example liposomes may be formed as described in U.S. Pat. Nos. 4,089,801 and 4,675,310, microspheres may be formed as described in U.S. Pat. No. 7,083,572, nanoparticles may be formed as described in U.S. Pat. No. 6,632,671, microbubbles may be formed as described in U.S. Pat. No. 5,849,727, etc. It is also known in the art how to incorporate or encapsulate one or more therapeutic agents in the carrier particles for delivery. Large porous particles may be prepared using conventional techniques such as spray drying or emulsion solvent evaporation, or through supercritical fluid derived processes such as those described by Koushik & Kompella (2004) Pharm. Res. 21:524-35.

The composition and size of the carrier particles is selected by the practitioner depending on the desired method of administration, in accordance with the therapeutic agent to be delivered. For example, for pulmonary administration, large (diameters greater than about 5 μm) porous microparticles of PLGA are desirable for maximizing deep-lung delivery, because a size of greater than about 5 μm helps avoid alveolar macrophage clearance, thus enabling sustained drug delivery through the lungs. These large particles also increase the dispersibility and entrainment of the drug particles from an inhaler, thus making it possible to efficiently deliver a dose using a passive dry powder inhaler. In a preferred embodiment, carrier particles with average diameters less than 50 μm are used.

For periocular delivery, sustained release is enhanced by larger particles of greater than 200 nm, which are retained at the administration site for up to 60 days, as reported by Amrite & Kompella (2005) J. Pharm. Pharmacol. 57(12):1555-63. Smaller particles (e.g., 20 nm) may be desirable for some ocular applications even though the smaller size particles generally have a reduced residence time in ocular tissue, because reduced residence time can be offset by increasing the administration frequency of the composition (e.g., eye drops). For ocular topical and intravitreal delivery, particles smaller than 50 micrometers are preferred to avoid foreign body sensation, although some therapeutic agents (e.g., triamcinolone acetonide) permit a larger carrier particle to be tolerated.

In a preferred embodiment, the carrier particles are microparticles (about 1-1000 μm) or nanoparticles (about 1-1000 nm). In another preferred embodiment, the carrier particles have an average diameter less than about 100 μm, about 75 μm, about 60 μm, about 50 μm, about 40 μm, about 25 μm, about 20 μm, about 15 μm, about 10 μm, about 5 μm, about 2.5 μm, about 1000 nm (1 μm), 500 nm, 300 nm, 200 nm, 150 nm, 100 nm, 75 nm, 50 nm, 30 nm, 20 nm, 15 nm, 10 nm, 5 nm, or 1 nm. In another preferred embodiment, the carrier particles have an average diameter of about 1 nm to about 1 micron, about 5 nm to about 500 nm, about 5 nm to about 200 nm, about 5 nm to about 150 nm, about 5 nm to about 100 nm, about 5 nm to about 75 nm, about 5 nm to about 50 nm, about 10 nm to about 300 nm, about 10 nm to about 200 nm, about 10 nm to about 150 nm, about 10 nm to about 100 nm, about 10 nm to about 75 nm, about 10 nm to about 50 nm, or about 15 nm to about 75 nm.

In another preferred embodiment, the carrier particles have an average diameter greater than about 100 nm, about 200 nm, about 300 nm, about 400 nm, about 500 nm, 600 nm, 700 nm, 800 nm, 900 nm, 950 nm, 1000 nm (1 μm), 5 μm, 10 μm, 15 μm, 20 μm, 25 μm, 40 μm, 50 μm, 60 μm, 75 μm or 100 μm. In still another preferred embodiment, the carrier particles have an average diameter of about 500 nm to about 500 μm, about 600 nm to about 400 μm, about 700 nm to about 300 μm, about 750 nm to about 250 μm, about 800 nm to about 200 μm, about 900 nm to about 100 μm, about 950 nm to about 50 μm, about 975 nm to about 25 μm, and about 1000 nm to about 15 μm.

C. Targeting Moieties

The carrier particles of the invention include targeting moieties. As used herein, the terms "targeting moiety" and "targeting agent" are used interchangeably and are intended to mean any agent, such as a functional group, that serves to target or direct the carrier particle to a particular location or association (e.g., a specific binding event). Thus, for example, a targeting moiety may be used to target a molecule to a specific target protein or enzyme, or to a particular cellular location, or to a particular cell type, to selectively enhance accumulation of the carrier particles. Suitable targeting moieties include, but are not limited to, polypeptides, nucleic acids, carbohydrates, lipids, hormones including proteinaceous and steroid hormones, growth factors, receptor ligands, antigens and antibodies, and the like. For example, the carrier particles may include a targeting moiety to target the carrier particles (including therapeutic or diagnostic agents associated with the carrier particles) to a specific cell type, or a particular subcellular location. More than one targeting moiety can be conjugated or otherwise associated with each carrier particle, and the target molecule for each targeting moiety can be the same or different.

The targeting moiety can function to target or direct the carrier particle to a particular location, cell type, diseased tissue, or association. In general, the targeting moiety is directed against a target molecule. As will be appreciated by those in the art, the carrier particles of the invention can be applied locally or systemically administered (e.g., injected intravenously), thus, preferred targeting moieties are those that allow concentration of the therapeutic agents in a particular localization. In preferred embodiments, the targeting moiety allows targeting of the carrier particles of the invention to a particular tissue or the surface of a cell.

In some embodiments, the targeting moiety is an antibody. The term "antibody" includes entire antibodies as well as antibody fragments (such as Fv, Fab, Fab', F(ab')$_2$ or other antigen-binding subsequences of antibodies), and encompasses human antibodies, fully human antibodies such as those produced via phage display or transgenic mice having human immunoglobulin genes, humanized antibodies, chimeric antibodies, etc., either produced by the modification of whole antibodies or those synthesized de novo using recombinant DNA technologies. In a preferred embodiment, the antibody is directed against a receptor on the cell-surface, including, but not limited to an LHRH receptor or a transferrin receptor.

In a preferred embodiment, the targeting moiety is all or a portion (e.g., a binding portion) of a ligand for a cell surface receptor. Suitable ligands include, but are not limited to, peptides, hormones, lipids, proteins, glycoproteins, signal transducers, growth factors, cytokines, and others. The ligands may be human or derived from a human, or may be from any other animal, including cow, pig, sheep, dog, rabbit, rat, mouse, hamster, chicken, frog, monkey, or any other bovine, canine or avian species. The native sequences of suitable ligands are readily available in GenBank and other public databases, for example sequences of human transferrins are available in GenBank as Accession numbers NM001063, XM002793, XM039847, NM002343 and NM013900, among others.

In a preferred embodiment, the targeting moiety is an LHRH-receptor-targeting moiety, that is, a targeting moiety directed to an LHRH receptor. Suitable LHRH-receptor-targeting moieties include LHRH agonists such as, but not limited to deslorelin, buserelin, nafarelin, or leuprolide. In another preferred embodiment, the targeting moiety is an LHRH analog having a substitution at the sixth amino acid residue, a D-amino acid substitution (on or around the sixth amino acid residue), the N-terminal domain of LHRH, the C-terminal domain of LHRH, the amino acid sequence of LHRH with additional amino acids at the C-terminus (for example as described in U.S. Pat. No. 5,897,863), and/or a type II β-turn conformation, or any combination of the foregoing. Preferred D-amino acids are D-amino acids having bulky hydrophobic side chains, particularly aromatics, and particularly preferred D-amino acids are D-lysine, D-ornithine, D-glutamic acid, D-aspartic acid, D-cysteine, and D-tyrosine. Particularly preferred targeting moieties are LHRH analogs having the N-terminal domain of LHRH and a D-amino acid substitution at the sixth amino acid residue, and LHRH analogs having the N-terminal domain of LHRH and a type II β-turn conformation. In a particularly preferred embodiment, the targeting moiety is deslorelin, a nonapeptide with the amino acid sequence pGlu-His-Trp-Ser-Tyr-D-Trp-Leu-Arg-ProNHEt (SEQ ID NO: 1).

In a preferred embodiment, the targeting moiety is a transferrin-receptor-targeting moiety, that is, a targeting moiety directed to a transferrin receptor. Suitable transferrin-receptor-targeting moieties include a transferrin or transferrin variant, such as, but not limited to, a serum transferrin, lacto transferrin (lactoferrin) ovotransferrin, or melanotransferrin. In another embodiment, the targeting moiety is a serum transferrin or transferrin variant such as, but not limited to a hexasialo transferrin, a pentasialo transferrin, a tetrasialo transferrin, a trisialo transferrin, a disialo transferrin, a monosialo transferrin, or an asialo transferrin, or a carbohydrate-deficient transferrin (CDT) such as an asialo, monosialo or disialo transferrin, or a carbohydrate-free transferrin (CFT) such as an asialo transferrin. In still another embodiment, the targeting moiety is a transferrin variant having the N-terminal domain of transferrin, the C-terminal domain of transferrin, the glycosylation of native transferrin, reduced glycosylation as compared to native (wild-type) transferrin, no glycosylation, at least two N terminal lobes of transferrin, at least two C terminal lobes of transferrin, at least one mutation in the N domain, at least one mutation in the C domain, a mutation wherein the mutant has a weaker binding avidity for transferrin receptor than native transferrin, and/or a mutation wherein the mutant has a stronger binding avidity for transferrin receptor than native transferrin, or any combination of the foregoing.

In another preferred embodiment, the targeting moiety is an "ocular targeting moiety" or a "nasal targeting moiety", which is a targeting moiety directed to either an LHRH or a transferrin receptor, including any of the LHRH-receptor-targeting moieties and transferrin-receptor-targeting moieties described above.

The terms "linked" and "conjugated" in the context of the carrier particles of the invention, are used interchangeably to refer to any method known in the art for functionally connecting moieties (such as targeting moieties), including, without limitation, recombinant fusion, covalent bonding, disulfide bonding, ionic bonding, hydrogen bonding, and electrostatic bonding.

As shown in Examples 5-8, uptake of untargeted carrier particles by the corneal epithelium was about 1.1 to 1.6% at 5 minutes, and remained at this level even after 60 minutes. Total corneal uptake in 5 minutes was about 2.4 percent. Removal of the corneal epithelium resulted in ~22% particle uptake in the corneal stroma at 5 and 60 minutes, indicating that corneal epithelium is a significant barrier to topical carrier particle delivery. When carrier particles were conjugated to targeting moieties (deslorelin and transferrin), however, corneal epithelial uptake was enhanced by 3- and 4.5-fold at 5 min and by 4.5- and 3.8-fold at 60 min, respectively. The total corneal uptake in 5 min was also greatly improved to approximately 9 and 16% for carrier particles with deslorelin and transferrin targeting moieties, respectively, with greater percent of particles accumulating in stroma. In all groups, the carrier particle uptake per unit tissue weight was in the order: corneal epithelium>stroma>endothelium. In excised cornea and conjunctiva studies, the transport and uptake was elevated for both deslorelin and transferrin targeted carrier particles. With isolated cornea and conjunctiva, minimal transport of unconjugated carrier particles across cornea as well as conjunctiva was observed at the end of 4 hours. Further, there was a significant lag time in the transport of unconjugated carrier particles, consistent with no uptake into aqueous humor in the ex vivo eyeball study. Conjugating the carrier particles to deslorelin and transferrin targeting moieties increased the uptake and transport of carrier particles by both conjunctiva and cornea. Further, low temperatures reduced transport of all carrier particle formulations across both tissues, suggesting energy-dependence of carrier particle transport. Confocal pictures of cornea and conjunctiva confirmed the enhanced uptake of targeted carrier particles as compared to un-targeted (unconjugated) particles. The pictures also reveal that carrier particle accumulation is localized to the corneal epithelium, and transferrin-targeted carrier particles are primarily localized to the conjunctival epithelium.

In a preferred embodiment, the uptake, transport, or both uptake and transport of carrier particles conjugated to a targeting moiety is at least 3 fold greater than that of unconjugated carrier particles that are otherwise identical, or at least 4 fold, 4.5 fold, 5 fold, 5.5 fold, 6 fold greater, or more than 6 fold greater. In another preferred embodiment, the uptake, transport, or both uptake and transport of carrier particles conjugated to a targeting moiety is at least 125 percent of that of unconjugated carrier particles that are otherwise identical, or at least 150 percent, 175 percent, 200 percent, 250 percent, 300 percent, 350 percent, 400 percent, 450 percent, 500 percent, or more than 500 percent.

D. Therapeutic Agents

The term "therapeutic agent" refers to any pharmaceutically acceptable acid, salt, ester, derivative, stereoisomer, pro-drug, or mixture of stereoisomers of a therapeutic agent, or to the therapeutic agent itself. Pharmaceutically acceptable acids, salts, esters, derivatives, stereoisomers, pro-drugs, and mixtures of therapeutic agents may also be used in the methods and compositions of the present invention. The term "pharmaceutically acceptable" used herein refers to those modifications of the parent compound (acids, salts, esters, etc.) that do not significantly or adversely affect the pharmaceutical properties (e.g., toxicity, efficacy, etc.) of the parent compound. For example, exemplary pharmaceutically acceptable salts administrable by means of the compositions of this invention include chloride, iodide, bromide, hydrochloride, acetate, nitrate, stearate, palmoate, phosphate, and sulfate salts. Exemplary techniques for producing pharmaceutically acceptable derivatives include methylation, halogenation, acetylation, esterification, and hydroxylation. Other examples also include those selected or derived from those described in U.S. Pat. No. 5,917,090.

"Therapeutic agents", as used herein, include agents for therapeutic, prophylactic, and diagnostic purposes. Therapeutic agents useful in the methods and compositions of the present invention include antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), vascular endothelial growth factor (VEGF) inhibitors or antagonists or intraceptors, receptor antagonists, RNA aptamers, antibodies, hydroxamic acids and macrocyclic anti-succinate hydroxamate derivatives, nucleic acids, plasmids, siRNAs, vaccines, DNA binding (minor groove) compounds, hormones, vitamins, proteins, peptides, polypeptides and peptide-like therapeutic agents, as well as diagnostic agents such as dyes, contrast agents, radioisotopes (e.g., $P^{32}$, $Tc^{99}$, $F^{18}$, $I^{131}$, etc.) and the like that are useful in prevention, diagnosis and treatment of diseases, conditions, syndromes, and symptoms thereof.

In a preferred embodiment, the therapeutic agent is a dry eye therapeutic agent, such as an anti-inflammatory (e.g., an immunomodulator or corticosteroid such as such as Restasis (cyclosporine)), a mucin stimulator, a mucin simulator, a lacrimal gland stimulator, a topical or systemic hormonal agent, an ocular surface protectant, a healing enhancer, or a tear film stabilizers, or other agent for treating and/or preventing dry eye. In another preferred embodiment, the therapeutic agent is an anti-VEGF agent, such as a VEGF inhibitor, VEGF antagonist, VEGF intraceptor, aptamer (e.g., Macugen (pegaptanib)), antibodies to VEGF (e.g., Avastin (bevacizumab) or Lucentis (ranibizumab)), or anti-inflammatories (e.g., triamcinolone acetonide or Retaane (anecortave acetate)). In yet another preferred embodiment, the therapeutic agent is useful in treating disorders of the posterior segment of the eye such as retinopathies (e.g., diabetic retinopathy, proliferative retinopathy, retinopathy of prematurity, choroidal vascularization, proliferative vitreoretinopathy, etc.), macular degeneration, and other vascular disease. Therapeutic agents for treating disorders of the posterior segment of the eye include anti-angiogenics, anti-neovascularization agents, anti-VEGF agents, and the like. In a different preferred embodiment, the therapeutic agent is an glaucoma therapeutic agent, such as a beta blocker (e.g., timolol, levobunol), parasympathomimetic (e.g., pilocarpine, carbachol, phospholine iodide), carbonic anhydrase inhibitor (e.g., acetazolamide, dorzolamide), alpha agonist (e.g., epinephrine, apraclonidine), prostaglandin agonist (e.g., latanoprost), or hyperosmotic (e.g., mannitol). In another preferred embodiment, the therapeutic agent is a nucleic-acid based agent, such as a nucleic acid, aptamer, plasmid, or siRNA, for example a plasmid that is selectively expressed only in certain tissues or cells and thus can be used in a diagnostic assay for certain conditions or disorders.

In addition, the compositions of the invention may be enriched with one or more of the stereoisomers of a therapeutic agent, or may be substantially optically pure with respect to one stereoisomer. The methods for using therapeutic agents may also comprise enriched stereoisomers or mixtures. One skilled in the art is familiar with designing synthetic schemes that employ one or more optically pure reagents or intermediates, or stereoisomerically enriched reagents or intermediates, resulting in either a substantially optically pure composition or a stereoisomerically enriched composition. A substantially optically pure composition contains about 85 to about 95 percent, or higher, of one stereoisomer. Chromatographic, enzymatic, or selective crystallization techniques for enriching or purifying stereoisomers of therapeutic agents, mixtures of therapeutic agents, or any intermediate or reagent used to prepare a therapeutic agent may also be used.

In a preferred embodiment, the compositions of the present invention comprise a therapeutically effective amount of a therapeutic agent in a vehicle. The therapeutic amount will vary on the method of administration, condition to be treated, therapeutic agent, and the like. For example, for batimastat as a therapeutic agent to be administered topically to the eye, the therapeutically effective amount may be generally within the range of from about 0.01 to 50%, more typically 0.1 to 20%, for fluid compositions. Preferred concentrations of therapeutic agent(s) in the compositions of the present invention are in the range of about 0.01 to about 50 percent (wt/wt). A more preferred range of concentrations is from about 0.05 to about 25 percent, and even more preferred concentrations are from about 0.1 to about 10 percent.

As used herein, the term "therapeutically effective amount" means the total amount of each active component of the pharmaceutical composition or method that is sufficient to show a meaningful patient benefit, i.e., healing or amelioration of chronic conditions, a reduction in neovascularization or other symptoms, an increase in rate of healing of such conditions, or a detectable change in the levels of MMP or other related proteinases in the retina or surrounding tissue. When applied to an individual active ingredient, administered alone, the term refers to that ingredient alone. When applied to a combination, the term refers to combined amounts of the active ingredients that result in the therapeutic effect, whether administered in combination, serially, or simultaneously.

Therapeutic efficacy and toxicity of the compositions may be determined by standard pharmaceutical, pharmacological, and toxicological procedures in cell cultures or experimental animals. For example, numerous methods of determining $ED_{50}$ (the dose therapeutically effective in 50 percent of the population) and $LD_{50}$ (the dose lethal of 50 percent of the population) exist. The dose ratio between therapeutic and toxic effects is the therapeutic index, and it can be expressed as the ratio $ED_{50}/LD_{50}$. Compositions exhibiting high therapeutic indices are preferred. The data obtained from cell culture assays or animal studies may be used in formulating a range of dosages for human use. The dosage is preferably within a range of concentrations that includes the $ED_{50}$ with little or no toxicity, and may vary within this range depending on the dosage form employed, sensitivity of the patient, and the route of administration. If administration is not on a daily basis, for example if injections are given every few days or every few months, then more therapeutic agent will be included in each administration, so that daily release of the agent is adequate to meet therapeutic needs.

E. Pharmaceutical Compositions

The subject invention includes pharmaceutical compositions comprising targeted carrier particles associated with one or more therapeutic agents, within a pharmaceutically acceptable carrier. The pharmaceutical compositions can be formulated according to known methods for preparing pharmaceutically useful compositions. The carrier may be liquid, solid, or semi-solid, for example. Formulations are described in a number of sources which are well known and readily available to those skilled in the art.

The physical and chemical characteristics of the compositions of the invention may be modified or optimized according to the skill in the art. Thus, pH, osmotic pressure, viscosity, and the content of various additional components may be chosen from any appropriate range known or modified from the examples given here. In general, the pharmaceutical compositions of the invention may be manufactured in a manner that is itself known, e.g., by means of conventional mixing, dissolving, emulsifying, encapsulating, entrapping, spray drying, or lyophilizing processes.

The pH of the inventive compositions is preferably between about 4.5 and about 8, and may be adjusted for the particular therapeutic agent(s) used. Purified water USP and various acids and bases suitable for pharmaceutical use, or combinations of acids and bases, may be used for adjusting the pH of the compositions. Non-limiting examples of acids and bases include acetic acid, boric acid, citric acid, lactic acid, phosphoric acid, hydrochloric acid, sodium hydroxide, sodium phosphate, sodium borate, sodium citrate, sodium acetate, sodium lactate, and TRIS.

The osmotic pressure of the liquid compositions or vehicles may be adjusted by methods known in the art to be between about 10 to about 400 milliosmolar (mOsM), more preferably between about 100 to about 300 mOsM. A preferred method of adjusting osmotic pressure is the addition of physiologically and pharmaceutically acceptable salts. Sodium chloride, which approximates physiological fluid, is the preferred salt, for use in concentrations ranging from about 0.01 to about 1 percent by weight, or any value in that range. Preferably, the concentration is between about 0.1 to about 1 percent. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like, can also be used in addition to or instead of sodium chloride to achieve osmotic pressures within the above-stated ranges.

Additional components of the composition may be chosen from any of those used in or capable of being used in a pharmaceutical formulation, especially those designed for topical administration to the eye. A non-exclusive list of components includes preservatives, stabilizers, chelating agents, dyes, antibiotics, antimicrobials, and anti-fungal agents. Preservatives such as benzalkonium chloride may be used in a range between about 0.001 to 1 percent by weight, or any value in this range. The compositions of the present invention may further comprise pharmaceutically acceptable carriers, excipients, gels, solutions, or diluents suitable for topical ophthalmic administration, and may include pharmaceutically acceptable polymeric suspension agents. Suitable carriers or excipients include, but are not limited to, calcium carbonate, calcium phosphate, various sugars, starches, cellulose derivatives, gelatin, and polymers such as polyethylene glycol. Suitable techniques for the formulation and administration of the compositions of the present invention are known in the art.

The compositions may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions can include other agents conventional in the art having regard to the type of formulation in question.

The compositions may also be included in a kit. The kit can include, in non-limiting aspects, the carrier particles, therapeutic agents, targeting moieties, and/or other components. In preferred embodiments, the kit can include a composition ready for administration. Containers of the kits can include a bottle, dispenser, package, compartment, or other types of containers, into which a component may be placed. The container can include indicia on its surface. The indicia, for example, can be a word, a phrase, an abbreviation, a picture, or a symbol. The containers can dispense a pre-determined amount of the component (e.g. compositions of the present invention). The composition can be dispensed in a spray, an aerosol, or in a liquid form or semi-solid form. The containers can have spray, pump, or squeeze mechanisms. In certain aspects, the kit can include a syringe for administering the compositions of the present invention.

Where there is more than one component in the kit (they may be packaged together), the kit also will generally contain a second, third or other additional containers into which the additional components may be separately placed. The kits of the present invention also can include a container housing the components in close confinement for commercial sale. Such containers may include injection or blow-molded plastic containers into which the desired bottles, dispensers, or packages are retained. A kit can also include instructions for employing the kit components as well the use of any other compositions, compounds, agents, active ingredients, or objects not included in the kit. Instructions may include variations that can be implemented. The instructions can include an explanation of how to apply, use, and maintain the products or compositions, for example.

In a preferred embodiment, the carrier particles are in a non-viscous aqueous formulation, such as a pharmaceutically acceptable vehicle or buffer. Such preparations allow the ease of drop or spray formulation and administration, and allow injection into various compartments of the eye.

F. Methods of Treatment

The administration of the compositions of the present invention may be for a "prophylactic" or "therapeutic" purpose, or alternatively can be used for diagnostic purposes. The compositions of the present invention are said to be administered for a "therapeutic" purpose if the amount administered is physiologically significant to provide a therapy for an actual manifestation of the disease. When provided therapeutically, the compound is preferably provided at (or shortly after) the identification of a symptom of actual disease. The therapeutic administration of the compound serves to attenuate the severity of such disease or to reverse its progress. The compositions of the present invention are said to be administered for a "prophylactic" purpose if the amount administered is physiologically significant to provide a therapy for a potential disease or condition. When provided prophylactically, the compound is preferably provided in advance of any symptom thereof. The prophylactic administration of the compound serves to prevent or attenuate any subsequent advance of the disease.

Providing a therapy or "treating" refers to any indicia of success in the treatment or amelioration of an injury, pathology or condition, including any objective or subjective parameter such as abatement, remission, diminishing of symptoms or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, neuropsychiatric exams, and/or a psychiatric evaluation. For example, the methods of the invention successfully treat a patient's retinal neovascularization by decreasing the number of neovascular nuclei evident upon an examination of the retina.

Preferred subjects for treatment include animals, most preferably mammalian species such as humans, and domestic animals such as dogs, cats and the like, subject to disease and other pathological conditions. A "patient" refers to a subject, preferably mammalian (including human).

A variety of administration routes for the compositions of the present invention are available. The particular mode selected will depend, of course, upon the particular therapeutic agent selected, whether the administration is for prevention, diagnosis, or treatment of disease, the severity of the medical disorder being treated and dosage required for therapeutic efficacy. The methods of this invention may be practiced using any mode of administration that is medically acceptable, and produces effective levels of the active compounds without causing clinically unacceptable adverse effects. Such modes of administration include, but are not limited to, oral, buccal, sublingual, inhalation, mucosal, rectal, intranasal, topical, ocular, periocular, intraocular, transdermal, subcutaneous, intra-arterial, intravenous, intramuscular, parenteral, or infusion methodologies.

Ocular delivery of the compositions of the present invention may be accomplished in any suitable manner, such as by topical administration, intraorbital administration, periocular administration, tissue specific microinjection, or intravitreal injection. In a preferred embodiment, the composition is topically applied to an eye of a human or non-human animal, the latter including cows, sheep, horses, pigs, goats, rabbits, dogs, cats, and other mammals. The composition can be applied as a liquid drop, ointment, a viscous solution or gel, a ribbon or as a solid. The composition can be topically applied, without limitation, to the front of the eye, under the upper eyelid, on the lower eyelid and in the cul-de-sac. The application can be as a treatment of an infection in the eye or as a preventive such as prior to surgery.

Exemplary ophthalmic disorders that may be treated by various embodiments of the present invention include, but are not limited to, diabetic retinopathies, retinopathy of prematurity, proliferative retinopathies, retinal vascular diseases, vascular anomalies, macular degeneration, age-related macular degeneration and other acquired disorders, endophthalmitis, infectious diseases, inflammatory diseases, AIDS-related disorders, ocular ischemia syndrome, pregnancy-related disorders, peripheral retinal degeneration, retinal degenerations, toxic retinopathies, retinal tumors, choroidal tumors, choroidal disorders, vitreous disorders, retinal detachment and proliferative vitreoretinopathy, non-penetrating trauma, penetrating trauma, post-cataract complications, inflammatory optic neuropathies, retinitis pigmentosa, macular edema, glaucoma, posterior uveitis, endophthalmitis, corneal infections, corneal wounds or injuries or burns, corneal angiogenesis, corneal transplant rejection, ocular insult and systemic disease such as viral infection, arthritis and rosacea. In a preferred embodiment, the ophthalmic disorder to be treated or prevented is a disorder of the anterior segment of the eye, e.g., a disorder of the cornea, conjunctiva, ciliary body, iris and the lens. In a different preferred embodiment, the ophthalmic disorder to be treated or prevented is a disorder of the posterior segment of the eye, e.g., a disorder of the vitreous body, retina, optic nerve, and choroid.

Nasal delivery of the compositions of the present invention may be accomplished in any suitable manner, such as by topical administration, nasal sprays, nasal drops, irrigation, inhaled particles or powders, injection, or the like. Nasal delivery may be used for the treatment of nasal and sinus conditions as well as non-nasal conditions in the central nervous system or elsewhere in the body. Exemplary nasal disorders that may be treated by various embodiments of the present invention include, but are not limited to, nasal inflammation or rhinitis, nasal or sinus congestion, nasal polyps, infections, colds, and the like. A wide variety of non-nasal conditions may be treated via nasal delivery of the compositions of the present invention, including, but not limited to, prostate cancer, endometriosis, erectile dysfunction, Parkinson's disease, asthma, osteoporosis, Alzheimer's disease, GI tract disorders, herpes, diabetes, and the like.

The compositions and methods of the present invention have application in the treatment and prevention of prostate cancer. Angiogenesis plays a major role in the development, invasion and metastasis of prostate cancers, and vascular endothelial growth factor (VEGF) is the predominant proangiogenic factors commonly expressed in prostate cancers. High VEGF expression is shown to be associated with impaired response to chemotherapy in prostate cancers. The VEGF intraceptor Flt-23k is a recombinant construct of the subunits of high affinity VEGF receptor 1 (Flt) with the ER retention signal sequence (KDEL), which targets VEGF and VEGF receptor, thereby retaining VEGF in the ER and inhibiting angiogenesis. Such inhibition of VEGF secretion could be superior to other methods of sequestering VEGF, such as extracellular blockade by antibodies or aptamers or forming heterodimers of VEGF and placental growth factor (PlGF-KDEL).

Also provided are methods for prophylactic and therapeutic treatment of diseases and conditions manifesting or associated with the eye comprising administering a composition containing targeted carrier particles and a therapeutic agent to an animal in need of such treatment. For example, a topical ophthalmic composition or an intranasal spray may be administered. Another method provided is a method for identifying or selecting a topical ophthalmic composition for administering a therapeutic agent.

The dosage schedule and amounts effective for therapeutic and prophylactic uses, i.e., the "dosing regimen", will depend upon a variety of factors, including the stage of the disease or condition, the severity of the disease or condition, the general state of the patient's health, the patient's physical status, age and the like. In calculating the dosage regimen for a patient, the mode of administration also is taken into consideration. The dosage regimen also takes into consideration pharmacokinetics parameters well known in the art, i.e., the rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington, supra). The state of the art allows the clinician to determine the dosage regimen for each individual patient, therapeutic agent and disease or condition treated. Single or multiple administrations of the compositions of the present invention can be administered depending on the dosage and frequency as required and tolerated by the patient.

The duration of prophylactic and therapeutic treatment will vary depending on the particular disease or condition being treated. Some diseases lend themselves to acute treatment whereas others require long-term therapy. For example, proliferative retinopathy can reach a threshold in a matter of days as seen in retinopathy of prematurity, some cases of diabetic retinopathy, and neovascular glaucoma. Premature infants are at risk for neovascularization around what would be 35 weeks gestation, a few weeks after birth, and will remain at risk for a short period of time until the retina becomes vascularized. Diabetic retinopathy can be acute but may also remain in the proliferative phase for a longer period of time. Diabetic retinopathy will eventually become quiescent as the vasoproliferative signal diminishes due to neovascularization and destruction of the retina.

In another embodiment, the carrier particles may be loaded with a diagnostic or imaging agent, for use in medical diagnosis or imaging methods. For example, a composition comprising carrier nanoparticles may be administered to the ocular tissue of a subject, wherein said nanoparticles are coupled to at least one LHRH-receptor-targeting moiety, and said nanoparticles comprise at least one diagnostic contrast agent (such as, e.g., a magnetic resonance imaging contrast agent, such as chelated paramagnetic ion, or gadolinium), allowing the carrier nanoparticles to bind to ocular tissue, and then detecting a diagnostic contrast image of the ocular tissue.

Application of the teachings of the present invention to a specific problem or environment is within the capabilities of one having ordinary skill in the art in light of the teachings contained herein. Examples of the products and processes of the present invention appear in the following examples.

Example 1

Assay for Receptor mRNA Expression in Ocular Tissue

The expression of LHRH receptor (LHRH-R), transferrin receptor 1 (TfR1) and transferrin receptor 2 (TfR2) mRNA levels were quantified relative to the expression of these receptors in pituitary by real time polymerase chain reaction (real-time PCR). RNA isolation from bovine conjunctiva and corneal epithelium was carried out using RNA STAT-60 RNA isolation kit (TEL-TEST, Friendswood, Tex.). Briefly, freshly excised tissues (pituitary, corneal epithelium, and conjunctiva) were homogenized in 1 ml RNA STAT-60 (TEL-TEST, Friendswood, Tex.) solution followed by extraction with 200 µl of chloroform. The tissue debris, DNA as well as proteins were separated into the organic phase by centrifugation at 12,000 g for 15 min at 4° C. The aqueous phase contained the RNA. Further extraction was carried out with isopropanol (1:1 v/v ratio with the aqueous phase). The RNA was precipitated and separated by centrifugation at 12,000 g for 15 min at 4° C. The RNA pellet obtained was washed with 70% ethanol. Purified RNA was separated by centrifugation at 7500 g for 5 min at 4° C. The pellet was air dried and redissolved in 100 µl of nuclease free water by incubation at 55° C. for 15 min. Care was taken not to over dry the pellet in order to facilitate redissolution. The RNA samples were analyzed with UV spectrophotometry. Samples with $A_{260}$ to $A_{280}$ ratio equal to or more than 1.8 were considered to be free of DNA and protein contamination.

The RNA (5 μg) isolated from bovine corneal epithelium and conjunctiva was converted into cDNA by reverse transcription. Real-time PCR was carried out using the ABI PRISM 7500 Sequence Detection System (Applied Biosystems). The reactions were performed with 2×SYBR Green PCR master mix (Applied Biosystems), in the presence of 30 ng cDNA and 300 nM of specific primer sets, as shown in Table 1 below. Samples were analyzed in triplicates. Amounts of input RNAs in each sample were corrected for by dividing threshold cycle (Ct) of each specific gene by the Ct for 18s rRNA. Fold values were calculated as $2^{-\Delta Ct}$, where $\Delta Ct=Ct$ for the specific gene—Ct for 18s rRNA in the same RNA. The sample with the lowest expression was set to 1.0 fold and other data were adjusted to that baseline, as described in Roth et al. (2001) J. Endocrinology 169(2):361-71 and Schirman-Hildesheim et al. (2005) Endocrinology 146(8):3401-8.

TABLE 1

Primers Used for PCR

| Receptor Primer | Sequence (5' to 3') | SEQ ID NO. |
| --- | --- | --- |
| LHRH-R sense | GACCTTGTCTGGGAAAGATCC | 2 |
| LHRH-R antisense | CAGGCTGATCACCACCATCA | 3 |
| TfR1 sense | AGGAACCGAGTCTCCAGTGA | 4 |
| TfR1 antisense | ATCAACTATGATCACCGAGT | 5 |
| TfR2 sense | GTGGTCAGTTGAGGATGTCAA | 6 |
| TfR2 antisense | CCACACGTGGTCCAGCTTCTGGCGGGAG | 7 |
| 18S sense | GATATGGCTCATGTGGTGTTG | 8 |
| 18S antisense | AATCTTCTTCAGTCGCTC CA | 9 |

Real time PCR results showed quantifiable levels of LHRH-R, TfR1 and TfR2 mRNA in both bovine corneal epithelium as well as conjunctiva. FIG. 1 depicts the differential expression of LHRH and transferrin receptors in various bovine ocular tissues. The fold difference ($2^{-\Delta Ct}$) of LHRH-R, TfR1 and TfR2 between the corneal epithelium and conjunctive is presented as mean±standard deviation for n=3 samples. For this and other experiments, comparison of means of various groups was done using non parametric statistical analysis. Comparison of two groups was carried out using Mann Whitney test, however for comparison of more than two groups, Kruskal Wallis non parametric ANOVA was employed. Differences were considered statistically significant at $P \leq 0.05$. The asterisk indicates a $p<0.05$ compared with LHRH-R in the pituitary, the double asterisk indicates a $p<0.05$ compared with TfR1 in the pituitary, and the hash mark (#) indicates a $p<0.05$ compared with TfR2 in the pituitary. As shown in FIG. 1, the LHRH-R, TfR1 and TfR2 mRNA levels in bovine corneal epithelium were 36, 25 and 100 fold lower than their respective levels in pituitary, and the LHRH-R, TfR1 and TfR2 mRNA levels in bovine conjunctiva were found to be 20, 5 and 25 fold lower than their respective levels in pituitary.

Example 2

Western Blot Assay for Receptors in Ocular Tissue

The expression of LHRH receptor (LHRH-R), transferrin receptor 1 (TfR1) and transferrin receptor 2 (TfR2) in ocular tissue was assayed by Western blot. Homogenates of freshly excised bovine tissues (pituitary, corneal epithelium, and conjunctiva) were prepared as follows. About 200 mg of tissue was homogenized using a Tissue Tearor™ in tissue protein extraction reagent (T-PER, Pierce Biotechnology, Rockford, Ill.). After homogenization, the suspension was centrifuged at 3000 rpm at 4° C. to separate the tissue debris. The supernatant was aliquoted and stored at −80° C. until further use. Total protein content of each of tissue homogenate was estimated using Pierce's BCA kit (Pierce Biotechnology, Rockford, Ill.). Tissue samples (20 μg of protein) were then loaded onto polyacrylamide gels. Molecular weight markers ranging from 220 Da to 14.3 kDa (Amersham Life Science, Arlington Heights, Ill.) were used to identify LHRH receptor, transferrin receptors, and α-actin protein bands. The proteins were separated using preformed 10% polyacrylamide gels (Bio-Rad, Hercules, Calif.) and sodium dodecyl sulfate-polyacrylamide gel electrophoresis (SDS-PAGE). The gels were run at 60 V for 10 min and then continued at 120 V for another 1.5 hours. The proteins were then transferred to polyvinylidene fluoride (PVDF) membranes (Millipore, Bedford, Mass.) at 4° C. using a current of 480 mA. Immunoblotting was performed with specific antibodies for LHRH-R (1:100 dilution) (LabVision, Freemont, Calif.), TfR1 (1:1000 dilution) (Biodesign International, Saco, Me.), and TfR2 (1:1000 dilution) (Abcam Inc, Cambridge, Mass.) or the monoclonal anti α-actin antibody (1:1000 dilution) (Sigma-Aldrich, St Louis, Mo.) after treatment with blocking buffer containing 0.3% Tween, 1% BSA, and 5% non-fat dry milk (NFDM). Incubation with antibody was done overnight at 4° C. Following washes with Tris buffer at pH 7.4, secondary antibody, horseradish peroxidase conjugated mouse or rabbit immunoglobulin (Ig) (Jackson Immunoresearch, West Grove, Pa.), was added (1:1500) as needed and incubated at 4° C. for 1 hour. Protein bands were visualized using a ECL-Plus chemiluminescence kit (Amersham Biosciences, Piscataway, N.J.).

Figure 2:
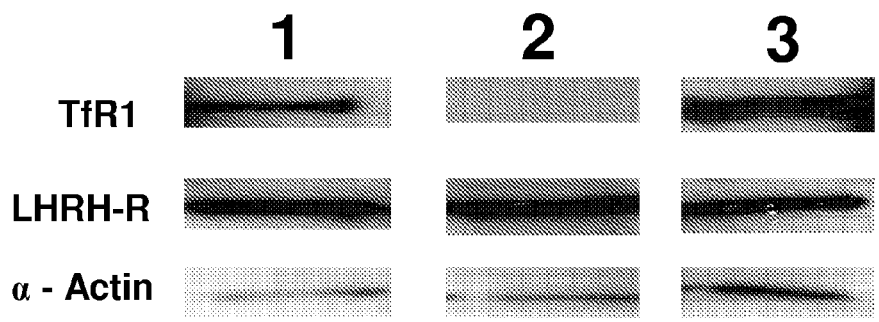
FIG. 2 is a Western blot assay to detect the presence of receptors for LHRH and transferrins in bovine ocular tissue.

As shown in FIG. 2, Western blot analysis indicated the presence of LHRH-R protein in bovine corneal epithelium and conjunctiva. TfR1 protein was clearly detectable in conjunctiva but only a faint band was observed in the corneal epithelium. TfR2 was not detected in any of the tissues. Lane 1 represents pituitary, lane 2 represents corneal epithelium, and lane 3 represents conjunctiva.

Example 3

Preparation of Targeted Compositions Using Polystyrene Carrier Particles

Due to their ease of use, polystyrene particles were used first, although they are not generally desirable for drug delivery because of their poor biodegradability. Fluorescent polystyrene particles (Fluospheres®) of 20 nm size surface modified with either carboxylate or aldehyde sulphate functionalities were purchased from Molecular Probes (Carlsbad, Calif.). Because particles in the nanometer range cannot be detected by bright field light, fluorescent nanoparticles were used so that the fluorescent label could be used to detect the nanoparticles on a cellular surface. Deslorelin, an LHRH agonist, was a gift from Balance Pharmaceuticals, Inc. (Santa Monica, Calif.). Transferrin, propidium iodide and the chemicals required for making buffer solutions were purchased from Sigma-Aldrich (St. Louis, Mo.).

Targeting moieties for both LHRH and transferrin receptors were attached to the carrier particles by conjugation. Four types of nanoparticles were prepared: deslorelin-carboxylate-conjugated nanoparticles (deslorelin-CA), transferrin-carboxylate-conjugated nanoparticles (transferrin-CA), deslorelin-aldehyde sulphate-conjugated nanoparticles (deslorelin-AS), and transferrin-aldehyde sulphate-conjugated nanoparticles (transferrin-AS).

The nanoparticles with carboxylate functionalities were conjugated to deslorelin or transferrin by covalent conjugation of the protein to the carboxylate surface functionality on the nanoparticles using carbodiimide. Briefly, 5 ml of 2 mg/ml NP suspension in 3(N-Morpholino) propanesulfonic acid (MOPS) buffer was added dropwise to 5 ml of 200 µg/ml protein solution. The mixture was allowed to react at room temperature for 15 min. Carbodiimide (4 mg) was added to the reaction mixture and the pH adjusted to 7.3-7.4. The reaction mixture was allowed to incubate at room temperature for 2 hours with vortexing. After 2 hours, the reaction was quenched by the addition of 100 mM glycine. The conjugated particles were separated from unreacted protein by dialyzing across a membrane with 50,000 molecular weight cut off (Spectra/Por, Spectrum Laboratories, CA). The nanoparticles with aldehyde sulphate functionalities were conjugated to deslorelin or transferrin via formation of a Schiff's base between the aliphatic aldehyde sulphate groups and the lysine ε-amines of proteins using a one step mix and wash protocol according to Technologies MPID, Working with FluoSpheres fluorescent microspheres (2004). Briefly, 100 µl of peptide (deslorelin or transferrin) solution (1 µg/ml) was added to 1 ml of particle suspension (1 mg/ml). The reaction mixture was allowed to stand overnight at room temperature. The conjugated particles were separated from free peptide/protein by dialysis using a cellulose ester dialysis tubing of 50,000 molecular weight cut off.

Compositions of the targeted carrier particles were formulated by suspending particles in assay buffer (pH 7.4), containing 1.14 mM $CaCl_2$, 1.2 mM $MgSO_4$, 3 mM KCl, 0.4 mM $KH_2PO_4$, 25 mM $NaHCO_3$, 10 mM glucose, 122 mM NaCl, and 10 mM HEPES (N-2-hydroxyethylpiperazine-N'-2-ethanesulphonic acid). Assay buffer was pre-equilibrated to 37° C. or 4° C. for 30 min prior to each experiment.

Example 4

Characterization of Targeted Nanoparticles

Nanoparticle carrier particles were formed by the methods of the preceding Example, and characterized as follows. The particle size and the zeta-potential were measured using Zeta Plus zeta-potential analyzer (Brookhaven Instruments Ltd., New York, N.Y.), which employs the dynamic light scattering technique for particle size measurement. The particle size and zeta-potential measurements were made after 1:1000 dilution of particle stock in filtered deionized water. Further, the particles were visualized using a transmission electron microscope (TEM). The carbon-coated grids were floated on a suspension droplet of plain or functionalized nanoparticles on a flexible plastic film (Parafilm, Pechiney Plastic Packaging, Neenah, Wis.) to allow the adsorption of nanoparticles onto the grid. After drying the particles, uranyl acetate was added as a negative stain to the carbon grid and allowed to react with the particles. This procedure makes the particles electron dense, allowing their visualization using an electron microscope. The particles were photographed using EM410 Philips electron microscope (Eindhoven, The Netherlands) set at 60 kV and a magnification of 153000×.

Figure 3:
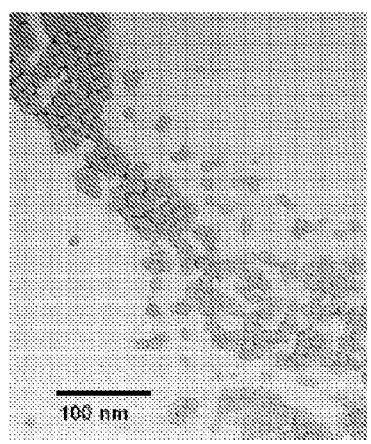
FIGS. 3-5 are TEM micrographs of various carrier nanoparticles of the present invention: unconjugated nanoparticles (FIG. 3), deslorelin-targeted nanoparticles (FIG. 4), and transferrin-targeted nanoparticles (FIG. 5).
Figure 4:
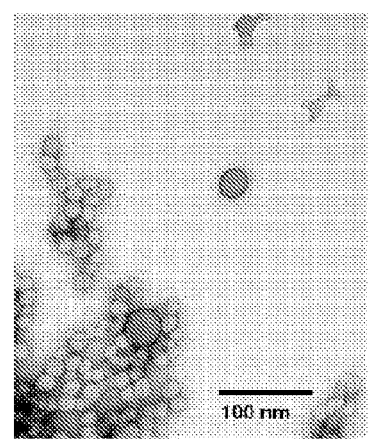
Figure 5:
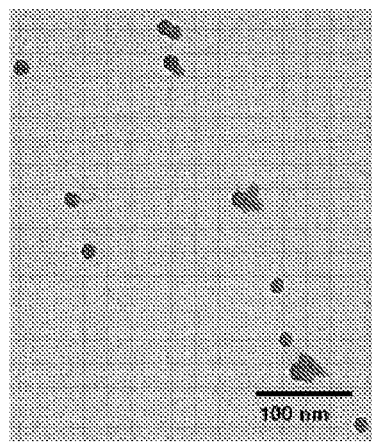

Table 2 presents physical properties measured for the nanoparticles. The diameters shown include a hydrodynamic layer around particles and the actual physical diameter is expected to be smaller, as evidenced in the transmission electron micrographs (FIGS. 3-5). In TEM images, deslorelin-CA and transferrin-CA nanoparticles exhibited somewhat darker surfaces compared to unconjugated nanoparticles. This is consistent with the uptake of electron microscopy stain by peptide/protein ligands on particle surfaces.

TABLE 2

Physical Properties of Various Nanoparticles

| Nanoparticle Type | Measured Diameter (nm) | Polydispersity Index | Zeta potential (mV) |
|---|---|---|---|
| Carboxylate | 85.2 ± 0.6 | 0.282 ± 0.004 | −57.93 ± 4.55 |
| Deslorelin-CA | 98.2 ± 0.6 | 0.223 ± 0.021 | −35.76 ± 1.73 |
| Transferrin-CA | 84.7 ± 0.8 | 0.224 ± 0.010 | −29.24 ± 4.33 |
| Aldehyde sulphate | 60.2 ± 1.2 | 0.259 ± 0.011 | −52.26 ± 3.09 |
| Deslorelin-AS | 133.8 ± 1.8 | 0.219 ± 0.004 | −25.57 ± 1.17 |
| Transferrin-AS | 67.5 ± 1.0 | 0.288 ± 0.012 | −20.62 ± 0.82 |

Key:
Data is expressed as mean ± standard deviation for n = 3

Example 5

Eye Drop Studies in Excised Bovine Eye Model

The precorneal residence of eye drops is very short and effective delivery to the cornea requires rapid binding and entry of drugs or carriers in vivo. The in vivo situation was simulated using an intact bovine eye for an ex vivo model. Using such a model with cornea facing upwards and the lower half of the eye maintained in a 37° C. bath, a drop was administered on the corneal surface and allowed to freely drain, to simulate in vivo clearance. Then, the particle uptake at 5 and 60 min was measured following thorough washing of the eye surface to remove any loosely adherent particles. The uptake was expected to be the highest for the solutes or carriers tightly bound to the corneal surface or for those that are rapidly taken up by the corneal epithelium. To maintain the surface moisture and to simulate tear flow in part, buffer drops (50 µl) were administered every 15 min, and the water bath was sealed.

Freshly excised bovine eyes were obtained from a local slaughterhouse (Nebraska Beef, Omaha, Nebr.). The experiments were initiated within 2-3 hours after sacrifice. For the experiment, bovine eyes were placed in Teflon coated wells containing assay buffer to immerse the posterior segment, while exposing the cornea towards the surface. The Teflon coated well plate was placed in a shaking water bath maintained at 37° C. and the water bath was sealed with Saran Wrap™ (S.C. Johnson & Son, Inc., Racine, Wis.). Alternatively, the setup was placed in a cold room maintained at 4° C. Prior to dosing, the eyes were equilibrated for about 30 min with assay buffer at 37° C. or 4° C. as required. The measured temperatures of the vitreous humor and aqueous humor in the 37° C. study were ~37° C. and ~35° C., respectively. The measured temperature was ~5° C. for both vitreous humor as well as aqueous humor in the 4° C. study. In the ex vivo studies, either 5 or 60 min time points were chosen since eye drops are rapidly cleared from the tissue surface and because high solute uptake is desired in a short time with eye drops.

Ex vivo model studies involved administration of a 50 µl dosing solution/suspension drop to the cornea followed by 50 µl drops of assay buffer on the cornea every 15 minutes to maintain corneal moisture. At the end of 0, 5, or 60 minutes study, the corneal surface was washed thrice with assay buffer (1 ml each time) followed by three washes with acid buffer (1 ml each time; assay buffer adjusted to pH 5.0 with HCl) to remove any loosely adherent nanoparticles prior to tissue analysis. The same protocol was followed even when plain buffer drops were assessed. To initiate the uptake experiment, a 50 µl eye drop of 10 mg/ml (in studies assessing the influence of epithelium in particle uptake) or 1 mg/ml nanoparticle suspension (unconjugated nanoparticles with carboxylate functionalities, deslorelin-CA and transferrin-CA) was topically administered to isolated bovine eyeballs. Buffer and wash treatments were performed as described above. At 5 and 60 minutes after drop instillation, the incubation was terminated and the corneal epithelium, stroma, endothelium and aqueous humor (0.5 ml) were isolated from the eyeball. The tissues were homogenized in 2% Triton-X. The supernatant obtained after centrifuging tissue homogenate at 5000 rpm (Marathon Micro AR, Fisher Scientific) for 10 minutes was analyzed by spectrofluorometry at excitation and emission wavelengths of 505 and 515 nm, respectively.

Unconjugated Nanoparticles

Figure 6:
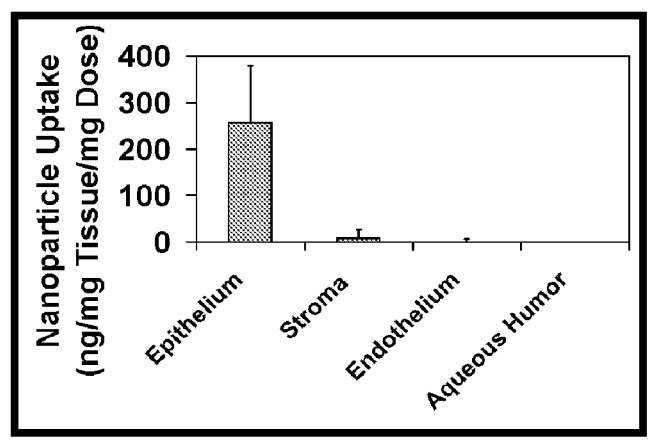
FIGS. 6-9 are charts depicting the results of targeted nanoparticle uptake studies in bovine ocular tissue. Intact bovine eyes were compared at 5 and 60 minutes (FIGS. 6 and 7) with bovine eyes devoid of corneal epithelium at the same times (FIGS. 8 and 9).
Figure 7:
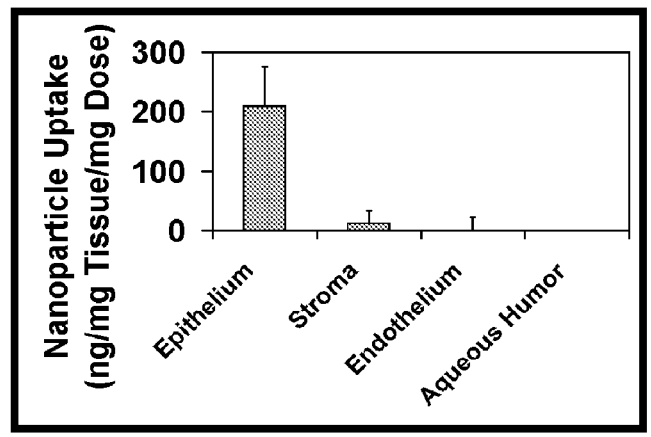

Results indicated that unconjugated nanoparticle uptake was significantly hindered by the corneal epithelium in the ex vivo eye model. The concentration of nanoparticles in various layers of cornea, at 5 and 60 minutes after topical instillation of a 50 µl drop of 10 mg/ml carboxylate nanoparticle suspension to isolated bovine whole eyeball at 37° C. followed the order: epithelium>stroma>endothelium. Tissue layers were isolated, homogenized, and particle uptake was quantified. As shown in FIGS. 6-7, corneal epithelium is a substantial barrier for unconjugated nanoparticle delivery. The concentration of nanoparticles detected after 5 minutes and 60 minutes in tissue including the epithelium is shown in FIGS. 6 and 7, respectively, and expressed as mean±standard deviation for n=3. The asterisk indicates a p<0.05 compared to the group on the left with epithelium, and the double asterisk indicates a p<0.05 compared to stroma, endothelium, and aqueous humor. Nanoparticles were detected in the corneal epithelium and corneal stroma after both 5 and 60 minutes, however, no nanoparticles were detected in the endothelium or aqueous humor at the two time points.

Figure 8:
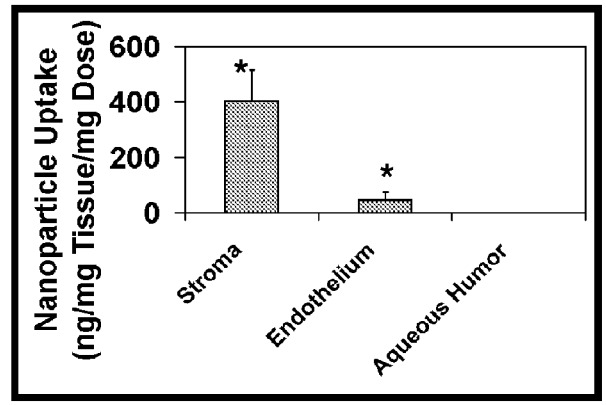
Figure 9:
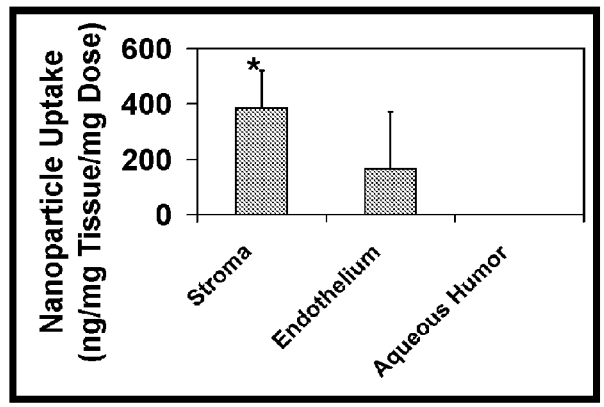
Figure 10:
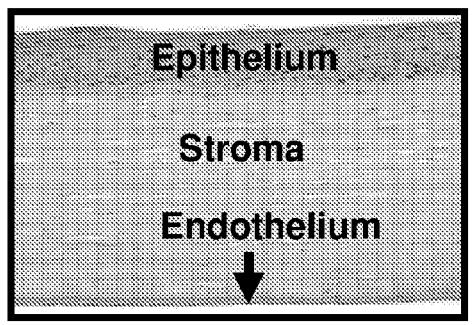
FIGS. 10 and 11 are histology pictures illustrating the nanoparticle concentration in bovine ocular tissue, with (FIG. 10) and without (FIG. 11) epithelium.
Figure 11:
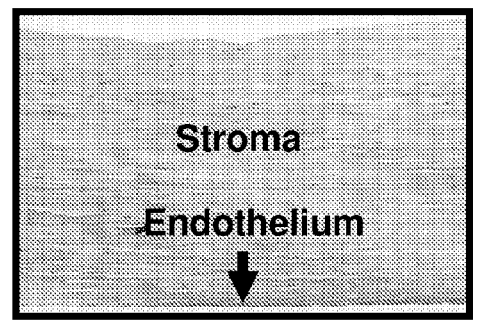

When the corneal epithelium was removed prior to topical nanoparticle suspension administration, the particle uptake at 5 and 60 min in corneal stroma increased by 45- and 32-fold, respectively. However, no nanoparticles could be detected up to 60 minutes in the aqueous humor even in the absence of corneal epithelium. Concentrations after 5 minutes and 60 minutes are shown in FIGS. 8 and 9, respectively. FIGS. 10 and 11 are histology pictures (magnification of 5×) of cornea after hematoxylin and eosin staining, illustrating the increased concentration of nanoparticles in the endothelium after removal of the corneal epithelium. Comparison of the unmodified nanoparticle dose entering the entire cornea at 5 minutes revealed a 2.05% dose in the presence of corneal epithelium and 22.93% dose in the absence of corneal epithelium. This result indicates that corneal epithelium is the most significant barrier to topical nanoparticle delivery.

Table 3 summarizes the measured concentrations in tissue, and the percent nanoparticle dose delivered with and without the epithelium. Tissue weights with epithelium were measured at time zero and those without epithelium were measured at the end of 60 min incubation; there were no significant differences in the weights of stroma and endothelium between the two time points. A dosing solution of 10 mg/ml nanoparticles at 50 µl volume was used. All other studies employed 1 mg/ml concentration. Total tissue amounts were calculated by multiplying tissue concentrations with the average weights indicated for each tissue in its entirety. As indicated below, neither the corneal endothelial weight or the corneal stromal weight (after removal of epithelium) increased during the 60 minute study, suggesting that there is no significant swelling of the tissues during the study.

TABLE 3

Nanoparticle Uptake Into Bovine Corneal Layers

| | Epithelium | Stroma | Endothelium |
|---|---|---|---|
| Measured with epithelium | | | |
| Tissue weight (g) | 0.0627 ± 0.002 | 0.5139 ± 0.021 | 0.0083 ± 0.001 |
| NP uptake at 5 min (%) | 1.60 | 0.45 | ND |
| Concentration at 5 min | 255.76 ± 123.6 | 8.85 ± 18 | ND |
| NP uptake at 60 min (%) | 1.31 | 0.63 | ND |
| Concentration at 60 min | 208.7 ± 67 | 12.2 ± 21 | ND |
| Measured without epithelium | | | |
| Tissue weight (g) | n/a | 0.5601 ± 0.038 | 0.0086 ± 0.001 |
| NP uptake at 5 min (%) | n/a | 22.54 | 0.039 |
| Concentration at 5 min | n/a | 402.6 ± 113 | 45.67 ± 29.7 |
| NP uptake at 60 min (%) | n/a | 21.56 | 0.143 |
| Concentration at 60 min | n/a | 385.02 ± 136 | 166.75 ± 204 |

Key:
Data is expressed as mean ± standard deviation for n = 3;
ND = not detectable;
concentration was measured as ng/mg tissue/mg dose.

Conjugated Nanoparticles

Figure 12:
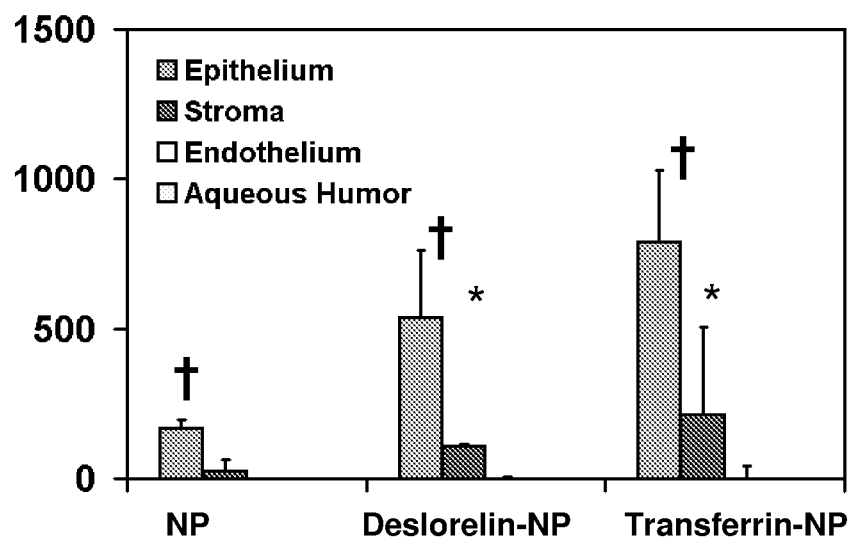
FIGS. 12 and 13 are charts depicting the results of targeted nanoparticle uptake studies in bovine ocular tissue at 5 and 60 minutes, respectively.
Figure 13:
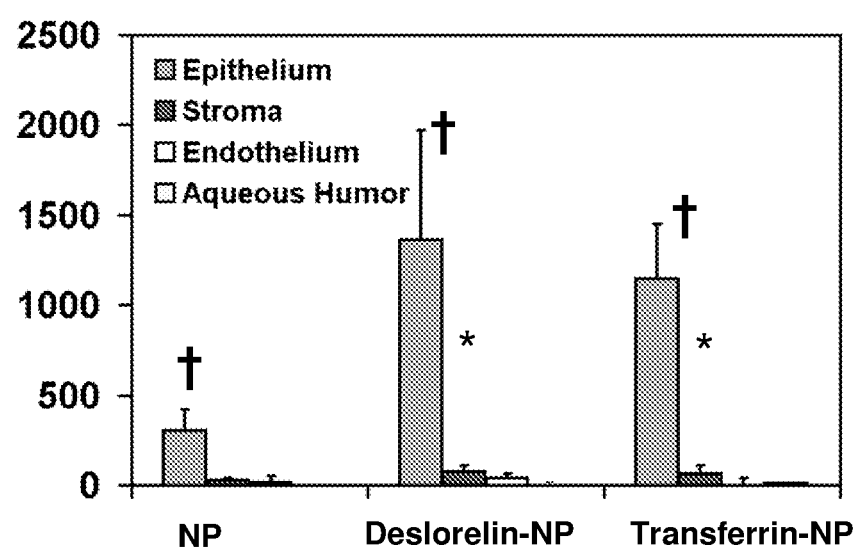

Results indicated that conjugated nanoparticles, both deslorelin-CA and transferrin-CA, exhibited improved uptake in the ex vivo eye model. Compared to unconjugated nanoparticles, deslorelin-CA and transferrin-CA nanoparticles had significantly higher uptake into corneal epithelium of ex vivo bovine eye model following topical instillation of 50 µl of 1 mg/ml particle suspension. As shown in FIGS. 12 and 13, the corneal epithelial uptake for deslorelin-NP and transferrin-NP was 3-fold and 4.5-fold higher than unconjugated nanoparticles after 5 minutes, and 4.5- and 3.8-fold higher after 60 minutes, respectively. The asterisk indicates a p<0.05 compared to the unconjugated group, and the hash (#) mark indicates a p<0.05 compared to stroma, endothelium, or aqueous humor. Table 4 summarizes the measured concentrations in tissue, and the percent nanoparticle dose delivered.

The corneal epithelial uptake of deslorelin-NP and transferrin-NP was also assessed in the presence of free conjugating ligand and at low temperature (4° C.). As shown in Table 5 the uptake of these particles was significantly decreased in the presence of free deslorelin (1 mg/ml) and transferrin (1 mg/ml), respectively, and at 4° C., indicating the involvement of a receptor mediated process.

TABLE 4

Nanoparticle Uptake Into Bovine Corneal Layers

|  | Unconjugated | Deslorelin-CA | Transferrin-CA |
|---|---|---|---|
| Corneal Epithelium | | | |
| NP uptake at 5 min (%) | 1.05 | 3.38 | 4.96 |
| Concentration at 5 min | 169 ± 28 | 539 ± 225 | 791 ± 239 |
| NP uptake at 60 min (%) | 1.90 | 8.54 | 7.19 |
| Concentration at 60 min | 304 ± 120 | 1362 ± 612 | 1146 ± 307 |
| Corneal Stroma | | | |
| NP uptake at 5 min (%) | 1.32 | 5.54 | 10.98 |
| NP uptake at 60 min (%) | 1.58 | 3.82 | 3.31 |

Key:
Data is expressed as mean ± standard deviation for n = 3;
ND = not detectable;
concentration was measured as ng/mg tissue/mg dose.

TABLE 5

Influence of Free Ligands and Low Temperature On Uptake

| | Corneal epithelial uptake (60 min) (ng/mg tissue/mg dose) | | |
|---|---|---|---|
| Nanoparticle type | Control (37° C.) | With free ligand (37° C.) | Control (4° C.) |
| Deslorelin-CA | 1361.8 ± 611.9 | 579.5 ± 237.4* | 463.3 ± 54.5* |
| Transferrin-CA | 1146.3 ± 306.6 | 467.1 ± 131.9* | 307.1 ± 124* |

Key:
The data is expressed as mean ± s.d. for n = 3.
*P < 0.05 compared to controls at 37° C.

Example 6

Corneal Histology and Immunohistochemistry Analysis

For histological analysis, at 0 (control), 5, and 60 minutes after instillation of 50 μl assay buffer drop and buffer treatments as described in Example 5, corneas were isolated and immediately transferred to a 10% neutral buffered formalin solution. The tissues were subsequently embedded in paraffin and 4 μm thick sections were cut. The sections were stained with hematoxylin and eosin and viewed with a Zeiss Axioscope 40 microscope. Images were taken with a Hitachi HV-D25 digital camera using EPIX-XCAPLite software V2.2 for Windows.

For immunohistochemical analysis of the tight junctional architecture in the ex vivo bovine eye model for the duration of the uptake studies, corneas isolated at the beginning and end of the experiments described in Example 5 were labeled with anti-ZO1 antibody (rabbit anti-ZO1 antibody, Zymed, Carlsbad, Calif.). For the experiment, 50 μl drop of assay buffer was topically administered to isolated bovine eyeballs. The cornea was kept moist for the duration of experiment by instilling 50 μl drops of assay buffer on the cornea every 15 minutes. At 5 and 60 minutes after first drop instillation, the eyes were washed thrice with 1 ml assay buffer followed by three washes (1 ml each time) with acid buffer and the corneas were excised and fixed in 2% paraformaldehyde for 15 minutes at room temperature. The tissues were then permeabilized for 30 min at room temperature with 0.1% Triton-X solution in PBS containing 5% goat serum. The tissues were subsequently incubated with rabbit anti-ZO1 primary antibody (1:100) for 1 hour. The tissues were washed thrice with PBS for 15 min. Subsequently tissues were incubated for 1 hr with Alexa 488 secondary antibody (1:500) (Molecular Probes, Carlsbad, Calif.). The tissues were again washed thrice with PBS and were finally stained with 1 μg/ml propidium iodide for 5 min. The stained tissues were then imaged using a confocal microscope at 63× magnification.

Figure 14:
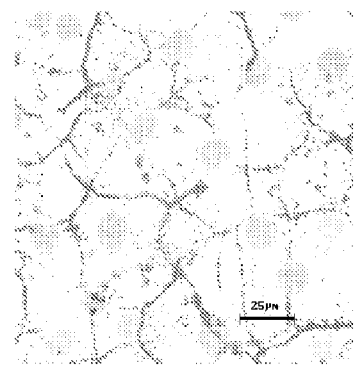
FIGS. 14-16 are confocal images of bovine corneas double labeled with anti-ZO1 antibody (web-like network) and propidium iodine (gray circular objects) at 0, 5 and 60 minutes, respectively, after application of unconjugated nanoparticles.
Figure 15:
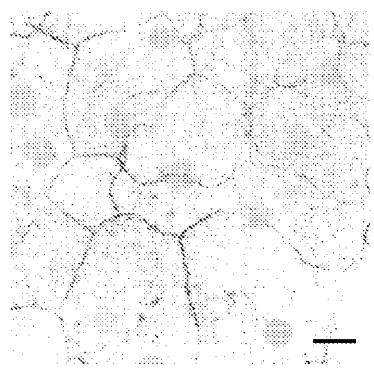
Figure 16:
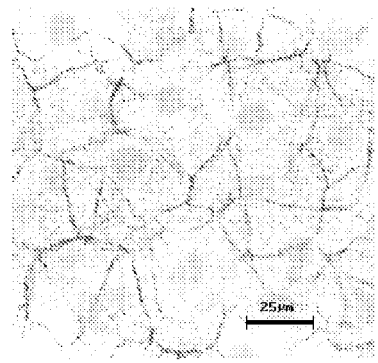
Figure 17:
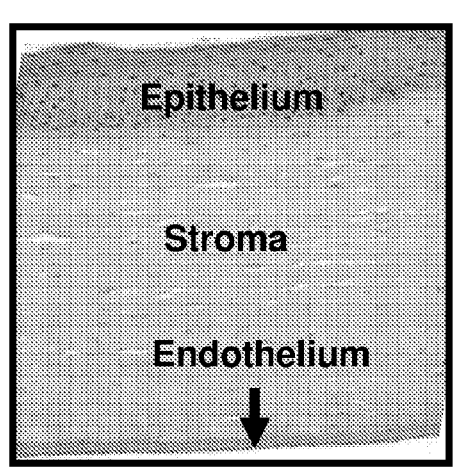
FIGS. 17-19 are histology pictures showing the nanoparticle concentration in bovine ocular tissue, at 0, 5 and 60 minutes, respectively, after application of unconjugated nanoparticles.
Figure 18:
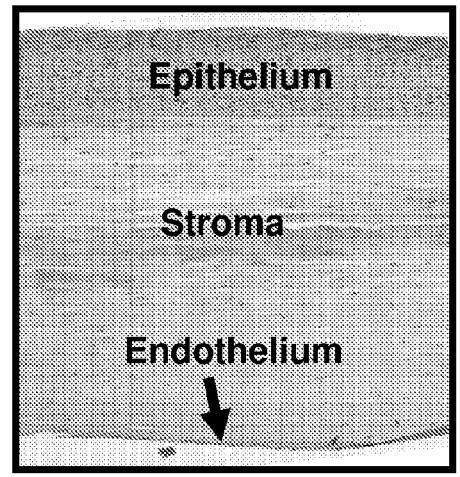
Figure 19:
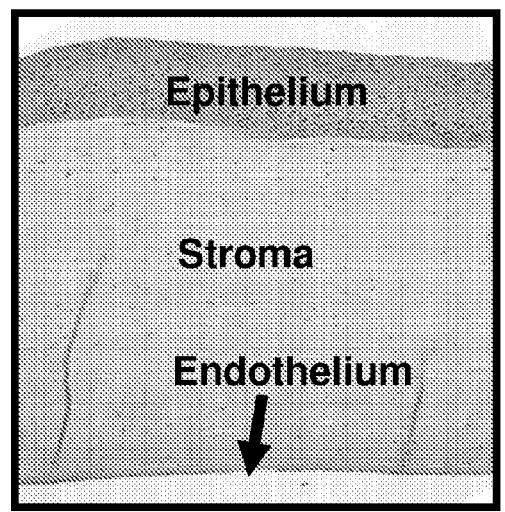

Histological and immunohistochemical analysis reveal that corneal integrity is preserved in the ex vivo bovine eye model of Example 5, and the nanoparticle formulations did not alter corneal integrity. FIGS. 14-16 are confocal images (magnification of 63×) of bovine corneas double-labeled with anti-ZO1 antibody (green) and propidium iodide (red) at 0 (control), 5, and 60 minutes, respectively. No significant differences were seen in the ZO1 staining pattern in freshly excised cornea and corneas following incubation for 5 or 60 minutes. FIGS. 17-19, which are histology pictures (magnification of 5×) of cornea after hematoxylin and eosin staining at 0 (control), 5, and 60 minutes, respectively, reveal no observed differences in the histology of these preparations.

Figure 20:
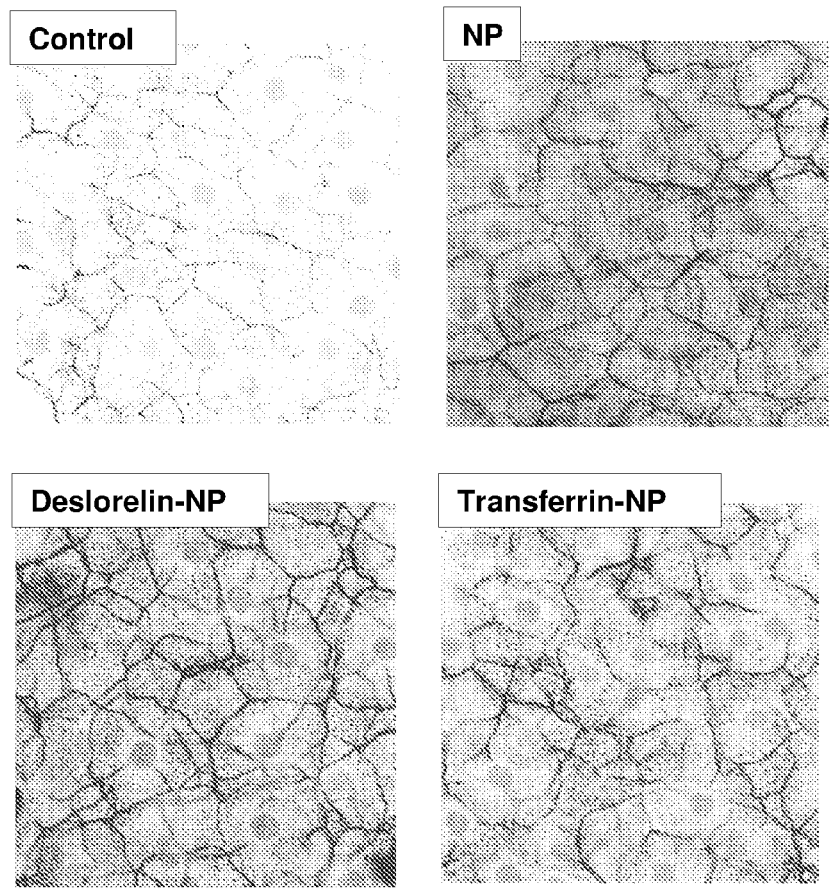
FIG. 20 are confocal images of bovine corneas double labeled with anti-ZO1 antibody (web-like network) and propidium iodine (gray circular objects) at 60 minutes after application of various nanoparticles, as labeled in the Figure.

FIG. 20 represents experimental data from the ex vivo study at 37° C. with three types of nanoparticles: unconjugated nanoparticles with carboxylate functionalities ("NP"), deslorelin-CA nanoparticles ("Deslorelin-NP"), and transferrin-CA nanoparticles ("Transferrin-NP"). The images are confocal images (magnification of 63×) of bovine corneas double-labeled with anti-ZO1 antibody (green) and propidium iodide (red). The corneal ZO1 staining pattern in the presence of the unconjugated nanoparticles, deslorelin-CA and transferrin-CA nanoparticles were also similar to controls instilled with similar volume of assay buffer.

Example 7

$^3$H-Mannitol Transport Analysis

The corneal barrier integrity in the ex vivo bovine model of Example 5 was also studied by analysis of $^3$H-mannitol transport, with or without nanoparticle exposure. $^3$H-mannitol was obtained from American Radiolabeled Chemicals, Inc. (St. Louis, Mo.). $^3$H-mannitol transport across excised bovine cornea was performed without any treatment or after dosing the bovine ex vivo eye model with a 50 μl drop of assay buffer or 50 μl of 1 mg/ml nanoparticle suspension followed by incubation up to 60 min with buffer treatments as described above. Temperature was maintained at 37° C.

Figure 21:
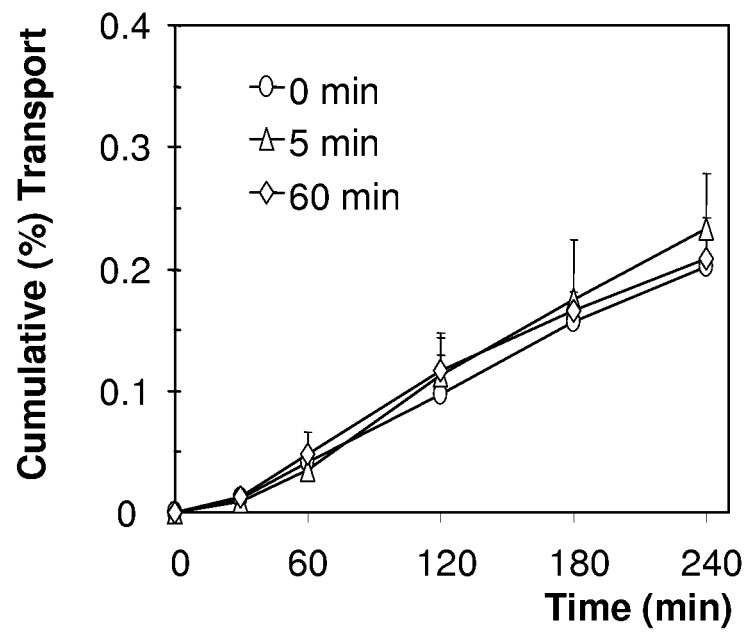
FIGS. 21 and 22 are graphs depicting the percent cumulative transport at various timepoints for control (plain) assay buffer (FIG. 21) and various nanoparticles (FIG. 22).
Figure 22:
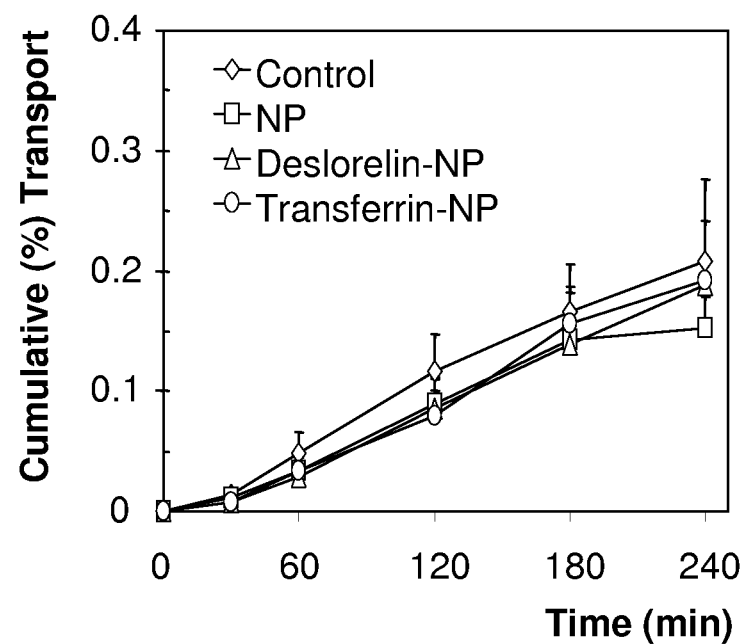

At 0, 5 and 60 minutes after assay buffer drop instillation and 60 min after nanoparticles drop instillation, the eyes were washed thrice with assay buffer (1 ml each time) and the corneas were isolated from the eyeball. The tissues were then mounted in modified Ussing chambers (Navicyte, Reno, N.Y.) for mannitol transport study. The aperture area of the chambers is 0.64 cm$^2$. The corneal area exposed was expected to be slightly greater than the chamber aperture area due to corneal curvature. $^3$H-mannitol (1.5 ml; 1 μCi/ml) was placed in the donor chamber (epithelial to endothelial transport) and plain assay buffer (1.5 ml) was placed in the receiver chamber. At various time points up to 4 hours, 200 μl samples were removed from the receiver chamber and replaced with an equal volume of fresh assay buffer. To each sample, 4 ml of scintillation fluid (Fisher Scientific, NJ) was added and the radioactivity was quantified using a liquid scintillation counter. Percentage cumulative transport was plotted for corneas obtained at various time points for the assay buffer, as shown in FIG. 21, and at 60 minutes after nanoparticle suspension administration, as shown in FIG. 22. Data are expressed as mean±standard deviation for n=4.

The apparent permeability coefficient of mannitol, a paracellular marker, did not differ significantly between freshly isolated corneas ($0.4\pm0.1\times10^{-6}$ cm/sec) and the corneas isolated at 5 ($0.5\pm0.1\times10^{-6}$ cm/sec) and 60 min ($0.47\pm0.04\times10^{-6}$ cm/sec) following exposure to 50 µl assay buffer drop in the ex vivo study. Additionally, mannitol permeability did not differ between NP ($0.41\pm0.18\times10^{-6}$) and deslorelin-NP ($0.41\pm0.04\times10^{-6}$) or transferrin-NP ($0.37\pm0.08\times10^{-6}$ cm/sec) groups or between nanoparticle groups and assay buffer treated group when permeability was assessed across corneas isolated at 60 min following exposure to 50 µl of various formulations in assay buffer.

Example 8

Uptake and Transport Studies in Bovine Ocular Tissue

Nanoparticle uptake and transport studies were performed using excised bovine cornea and conjunctiva mounted in vertical diffusion chambers. Modified Ussing chambers (Navicyte, Reno, N.Y.) were used to mount bovine corneas and conjunctivas for transport studies. The tissues were exposed to 1.5 ml of assay buffer with either conjugated or unconjugated nanoparticles (100 µg/ml) on the mucosal/tear side (donor side). The area of exposure is 0.64 cm$^2$ for conjunctiva and slightly greater for cornea due to curvature. The receiver side was exposed to 1.5 ml of assay buffer without nanoparticles. The buffers were pre-equilibrated to 37° C. or 4° C. as required and the chambers were maintained at the desired temperature. Samples were collected from the receiver chamber at various intervals up to 4 hours and the receiver chamber was replenished with an equal volume of temperature pre-equilibrated assay buffer. The experiment was terminated at 4 hours and the samples were stored in polypropylene tubes at 4° C. until analysis.

At the end of 4 hour transport studies, the tissue area exposed to particle suspension (aperture area: 0.64 cm$^2$) were cut and washed thrice with assay buffer followed by the acid buffer (pH 5.0). The tissues were then homogenized in 2% Triton-X using Tissue Tearor™. The tissue debris was separated by centrifugation at 3000 rpm (Marathon Micro AR) for 10 minutes. The supernatant was collected to analyze the amount of nanoparticles taken up by the tissue. The supernatant was analyzed by spectrofluorometry at excitation and emission wavelengths of 505 and 515 nm, respectively.

Figure 23:
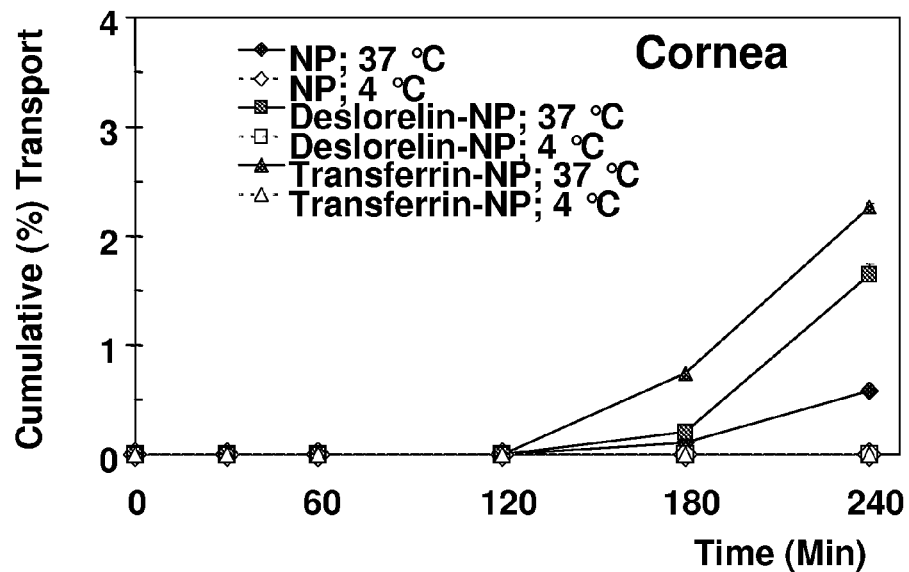
FIGS. 23 and 24 are graphs depicting the percent cumulative transport at various timepoints for various nanoparticles at two temperatures, for cornea (FIG. 23) and conjunctiva (FIG. 24).
Figure 24:
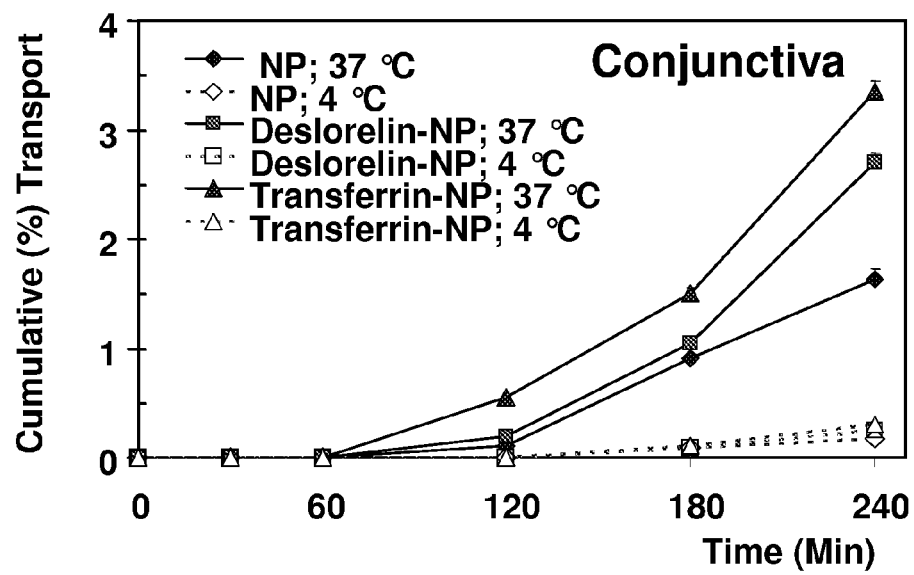

Results indicated that the targeted nanoparticles exhibited significantly enhanced transport and uptake in excised bovine cornea and conjunctiva. The cumulative transport of unconjugated nanoparticles, deslorelin-CA and transferrin-CA in 4 hours across isolated bovine cornea at 37° C. was $0.65\pm0.01$, $1.85\pm0.09$, and $2.76\pm0.03\%$, respectively, as shown in FIG. 23, and the corresponding values for conjunctiva were $1.8\pm0.09$, $3\pm0.09$ and $3.5\pm0.1\%$, respectively, as shown in FIG. 24. Thus, conjugation of deslorelin and transferrin to the surface of nanoparticles increased percent transport of nanoparticles across bovine cornea by 64 and 74%, respectively, and across conjunctiva by 40 and 51%, respectively. Interestingly, the nanoparticles were below detection limits in the receiver chamber up to 180 min for cornea and up to 120 min for conjunctiva, suggesting a significant lag time for the transport of nanoparticles. When the transport study was conducted at 4° C., corneal transport of all nanoparticles was completely abolished, with no detectable amounts of nanoparticles in the receiver chamber even at 4 hours. In conjunctiva, on the other hand, the reduction in the cumulative transport was 87, 88, and 89%, respectively, for unconjugated nanoparticles, deslorelin-CA, and transferrin-CA.

Figure 25:
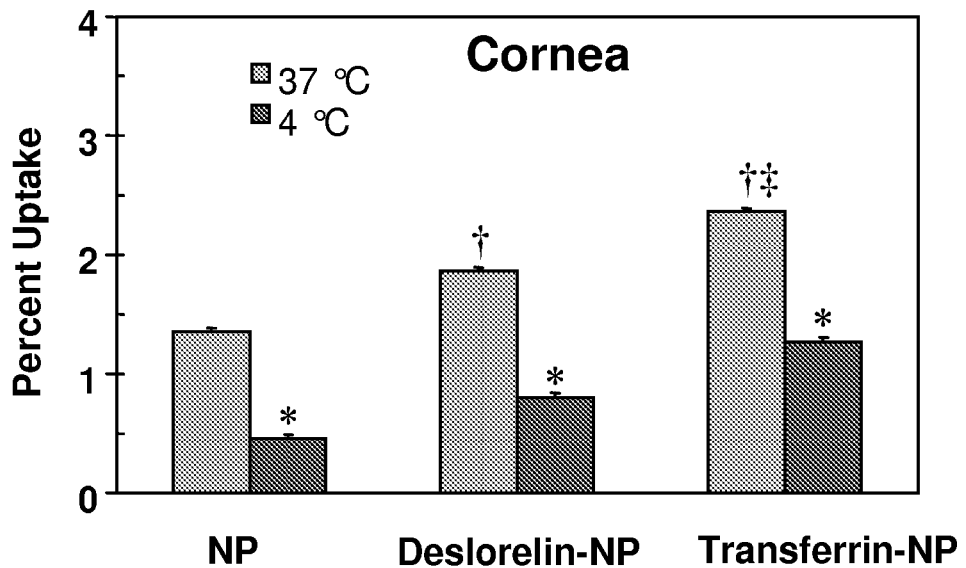
FIGS. 25 and 26 are charts depicting the percent uptake for various nanoparticles at two temperatures, for cornea (FIG. 25) and conjunctiva (FIG. 26).
Figure 26:
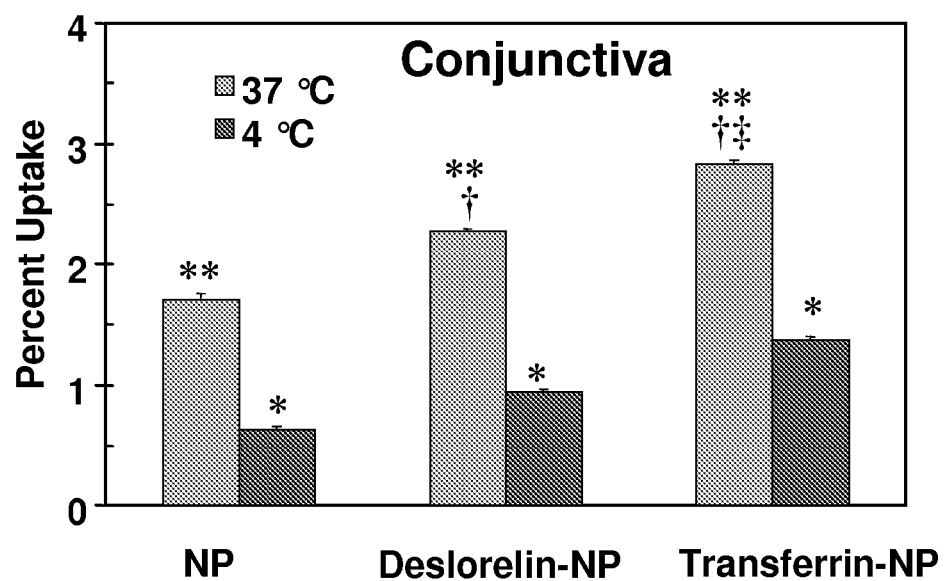

Conjugation of deslorelin and transferrin to nanoparticle surface significantly enhanced the uptake of nanoparticles by isolated bovine conjunctiva and cornea. The uptake of unconjugated nanoparticles, deslorelin-CA and transferrin-CA by isolated bovine cornea at 37° C. was $1.35\pm0.03$, $1.83\pm0.03$, and $2.36\pm0.03\%$, respectively, at the end of 4 hours, as shown in FIG. 25. The corresponding uptake in bovine conjunctiva was $1.71\pm0.05$, $2.27\pm0.02$ and $2.83\pm0.03\%$, respectively, as shown in FIG. 26. At 4° C., uptake nanoparticle uptake was reduced significantly. The reduction in corneal uptake was 66, 56, and 47%, respectively for unconjugated nanoparticles, deslorelin-CA and transferrin-CA, respectively. The corresponding reduction in conjunctival uptake was 63, 59, and 52%, respectively.

For FIGS. 23-26, data is expressed as mean±standard deviation for n=4. The asterisk indicates a $p<0.05$ compared to corresponding particles at 37° C., the hash (#) mark indicates a $p<0.05$ compared to unconjugated nanoparticles at 37° C., the double hash (##) mark indicates a $p<0.05$ compared to deslorelin-CA at 37° C., and the double asterisk indicates a $p<0.05$ compared to corresponding data for corneal uptake.

Confocal microscopy to determine nanoparticle uptake in different layers of cornea and conjunctiva was performed after the transport procedure. At the end of 4 hours, the tissue exposed to the particles suspension were isolated and frozen in a tissue freeze solution and 4 µm thick sections were cut. The tissue sections were then imaged using a confocal microscope at 20× magnification to determine nanoparticle uptake in the various regions of cornea (epithelium, stroma, and endothelium) and conjunctiva (epithelium and stroma). Control cornea and conjunctiva were not exposed to nanoparticles. Both tissues exhibited some background auto-fluorescence. In all particle groups, the fluorescence intensities were greater than those in the controls.

Figure 27:
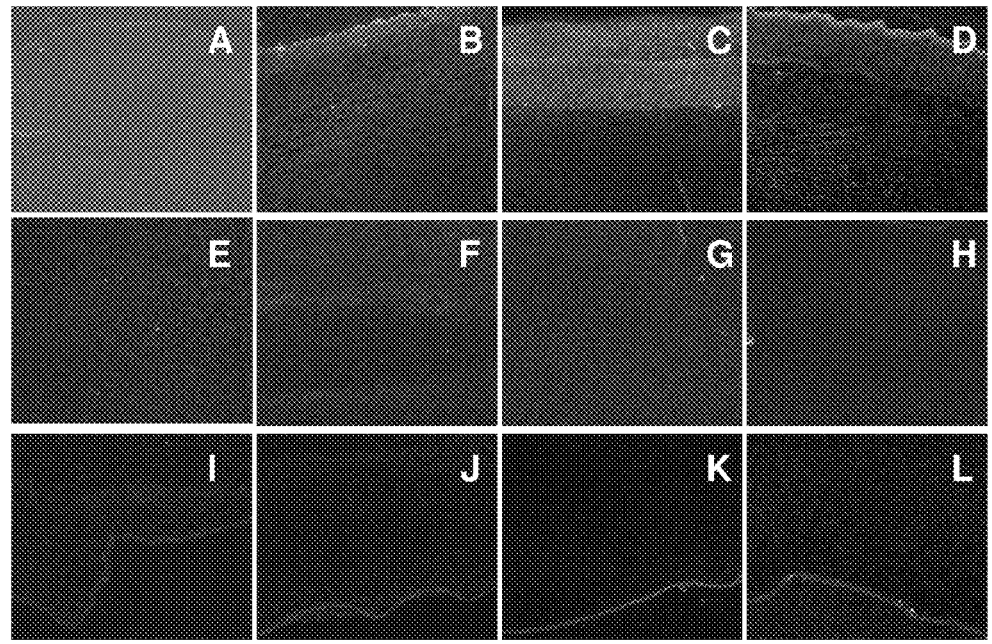
FIGS. 27 and 28 are panels of confocal images illustrating the uptake of nanoparticles in multiple layers of bovine ocular tissue after transport studies.
Figure 28:
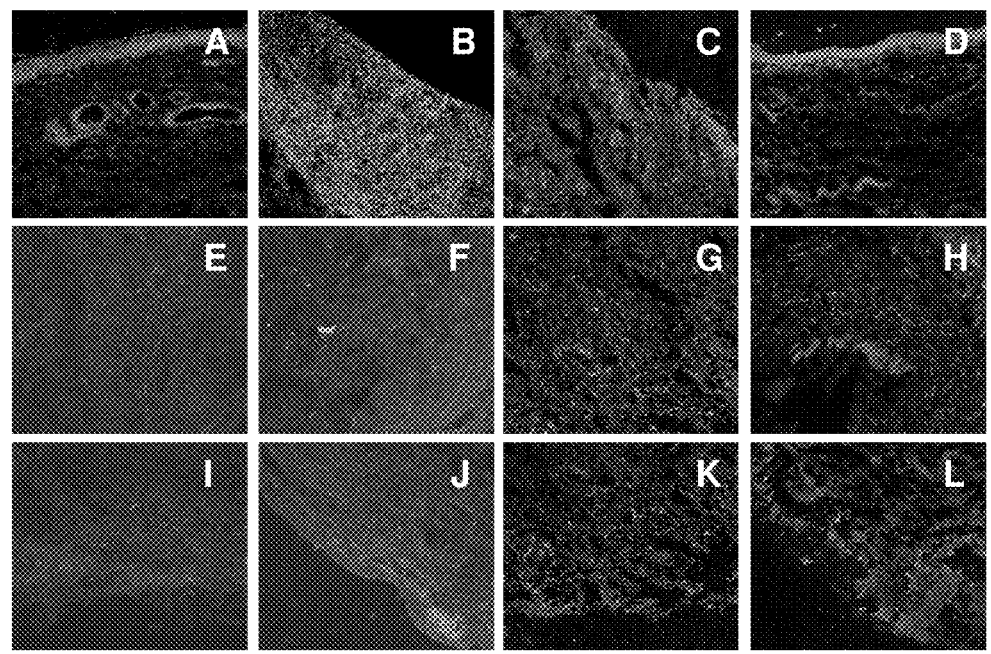

The fluorescent intensities of nanoparticles in various layers of cornea, followed the order: epithelium>stroma>endothelium, as shown in FIG. 27. In conjunctiva, the fluorescence intensities followed the order: epithelium>stroma for transferrin-NP, as shown in FIG. 28. For the other nanoparticles, the regions were less distinguishable in conjunctiva, possibly due to tissue folding upon isolation. However, nanoparticle distribution appeared less restricted in the conjunctiva compared to the cornea. The intensities of the different particles in the cornea and conjunctiva were generally in the order: NP<deslorelin-NP<transferrin-NP. For both FIGS. 27 and 28, panels A-D represent the top region of corneal tissue, panels E-H represent the middle region, and I-L represent the lower regions. Exposure to nanoparticles was as follows: the column entitled "blank" (panels A, E and I) was not exposed to any nanoparticles; the column entitled "NP" (panels B, F and J) was exposed to unconjugated nanoparticles; the column entitled "Deslorelin-NP" (panels C, G and K) was exposed to deslorelin-CA nanoparticles; and the column entitled "Transferrin-NP" (panels D, H and L) was exposed to transferrin-CA nanoparticles.

Example 9

Preparation of Biodegradable & Non-Biodegradable Carrier Particles

Two types of carrier particles were made: non biodegradable polystyrene carrier nanoparticles (FluoSpheres®, Molecular Probes, Carlsbad, Calif.) and biodegradable poly-(lactide-co-glycolide) (PLGA) carrier nanoparticles. Both types of nanoparticles were surface modified by conjugating either deslorelin or transferrin targeting moieties. The particle size and zeta potential of all the nanoparticles was determined by dynamic light scattering.

Preparation of peptide/protein conjugated FluoSpheres®: Deslorelin (Deslorelin-PS) or transferrin (Transferrin-PS) conjugated FluoSpheres® (PS) were prepared using a one-step mix and wash technique. Briefly, 100 µl of deslorelin or transferrin solution (100 µg/µl) was added to 1 ml of aldehyde sulfate nanoparticle suspension (1 mg/ml). The reaction was allowed to proceed overnight at room temperature. The conjugation occurs due to the formation of Schiff's base between the aliphatic aldehyde surface groups and the lysine 1-amine groups of the peptide/protein. The product was purified by separating the unbound ligand using a 10,000 molecular weight cut off cellulose ester dialysis tubing (Spectra/Por, Spectrum Laboratories, Rancho Dominguez, Calif.). Polystyrene FluoSpheres® bearing aldehyde sulfate surface functional group were obtained from Molecular Probes (Carlsbad, Calif.). Deslorelin was a gift from Balance Pharmaceuticals, Inc. (Santa Monica, Calif.). Transferrin was purchased from Sigma (St. Louis, Mo.).

Preparation of nile red loaded PLGA nanoparticles: Resomer 503H(COOH modified PLGA 50:50; i.v. 0.44 dl/g; Boehringer Ingelheim, Petersburg, Va.) (200 mg) was used for the preparation of nile red loaded particles. Briefly, nile red solution in dichloromethane 0.5 mg/ml (500 µl) was added into PLGA solution (100 mg/ml) in dichloromethane. This organic phase was poured into 2% w/v poly (vinyl alcohol), PVA (25 ml) and sonicated using a probe sonicator at 27 W for 3 min to form an emulsion. The emulsion was subsequently poured into 50 ml of 2% w/v PVA and stirred overnight at room temperature. The nanoparticle suspension was subjected to rotary evaporation (Rotovap, Buchi Rotavapor R200, Buchi Analytical Inc., New Castle, Del.) for 2 hours in a water bath at 40° C. (Buchi Heat Bath B490) to remove residual solvent. Nanoparticles were retrieved by centrifugation at ~30000 g for 40 min at 4° C. The particle pellet was resuspended in double distilled water (20 ml; repeated twice to remove surface bound PVA and plasmid) and lyophilized.

Preparation of deslorelin and transferrin conjugated PLGA nanoparticles: PLGA nanoparticles (PLGA-NP; 20 mg) were resuspended in 10 ml of MOPS buffer (pH 6.5). N-(3-dimethylaminopropyl)-N-ethylcarbodiimide (EDAC; 4 mg) was added to particle suspension. The nanoparticles were allowed to react with EDAC at room temperature for 2 h. Following incubation, 10 ml of 200 µg/ml protein solution was added drop-wise to the particle suspension and incubated at room temperature for 12 hours. The reaction was stopped using 100 µl of 100 mM glycine solution. Deslorelin (Deslorelin-PLGA) or transferrin (Transferrin-PLGA) conjugated nanoparticles were harvested by centrifugation at ~30000 g for 40 min. The particle pellet was resuspended in double distilled water (20 ml) and lyophilized.

Characterization of particles: The particle size and the zeta-potential were measured using ZetaPlus® zeta-potential analyzer, Brookhaven Instruments Ltd. (New York, N.Y.), which employs the dynamic light scattering technique for particle size measurement. The particle size and zeta-potential measurements were carried out after 1:1000 dilution of particle stock in filtered deionized water before lyophilization in filtered deionized water. The effective diameter, polydispersity index, and zeta potential for each type of nanoparticle have been summarized in Table 6. The effective diameter of conjugated nanoparticles was higher than that of unconjugated nanoparticles. The zeta potential of conjugated nanoparticles was also higher as compared to unconjugated nanoparticles, suggesting the conjugation of some of the surface functional groups with the deslorelin or transferrin.

TABLE 6

Physicochemical Properties of Various Nanoparticles

| Particle type | Effective diameter (nm) | Polydispersity index | Zeta potential (mV) |
|---|---|---|---|
| Polystyrene (PS) | 60.2 ± 1.2 | 0.259 ± 0.011 | −52.26 ± 3.09 |
| Deslorelin-PS | 133.8 ± 1.8 | 0.219 ± 0.004 | −25.57 ± 1.17 |
| Transferrin-PS | 67.5 ± 1.0 | 0.288 ± 0.012 | −20.62 ± 0.82 |
| PLGA | 290.7 ± 3.1 | 0.225 ± 0.028 | −22.54 ± 2.4 |
| Deslorelin-PLGA | 394.5 ± 4.6 | 0.239 ± 0.012 | −17.69 ± 2.3 |
| Transferrin-PLGA | 385.8 ± 4.6 | 0.206 ± 0.04 | −17.94 ± 1.5 |

Example 10

Comparison of Uptake of Carrier Particles in Human Retinal Pigment Epithelial Cells A study was performed to examine the effect of targeting moieties on biodegradable and non-biodegradable carrier particles and their uptake in ocular cells. The biodegradable and non-biodegradable targeted carrier particles of the preceding Example were used. Uptake of nanoparticles by human retinal pigment epithelial cells (ARPE-19 cell line) was quantified by measuring fluorescence in cell lysate obtained after incubation of targeted or untargeted (unconjugated) nanoparticles with ARPE-19 cell monolayers. Results indicated that carrier nanoparticles conjugated to a targeting moiety had higher particle size, higher zeta potential, and significantly higher uptake as compared to unconjugated carrier nanoparticles.

ARPE-19 cells were obtained from American Type Culture Collection (ATCC, Manassas, Va.). The cells were maintained in culture according to supplier's recommendation. All studies were conducted using confluent cells of passages 20-30. Dulbecco's modified Eagle's medium (DMEM-F/12), fetal bovine serum, penicillin-streptomycin and L-glutamine were obtained from Gibco-BRL (Invitrogen Inc., Carlsbad, Calif.). Cell culture flasks (T-75 cm$^2$) and plates were purchased from Corning Inc., (Corning, N.Y.). To investigate the uptake of particles, ARPE-19 cells between 20-30 passages were cultured in 24-well plates until confluency. Confluent monolayers were incubated with either unconjugated, deslorelin conjugated or transferrin conjugated nanoparticles (1 ml of 100 µg/ml suspension in serum free DMEM/F12), for 3 h. The monolayers were washed thrice with of phosphate buffered saline (PBS pH 7.4), followed by washing thrice with PBS pH 5.0. Finally, the cells were lysed using Cellytic M® (Sigma, St. Louis, Mo.). Fluorescence intensity of the cell lysates was determined at an excitation and emission wavelength of 505 and 515 nm, respectively, for FluoSpheres®. The excitation and emission wavelength used for nile red loaded PLGA nanoparticle uptake studies was 544 and 590 nm, respectively.

Figure 37:
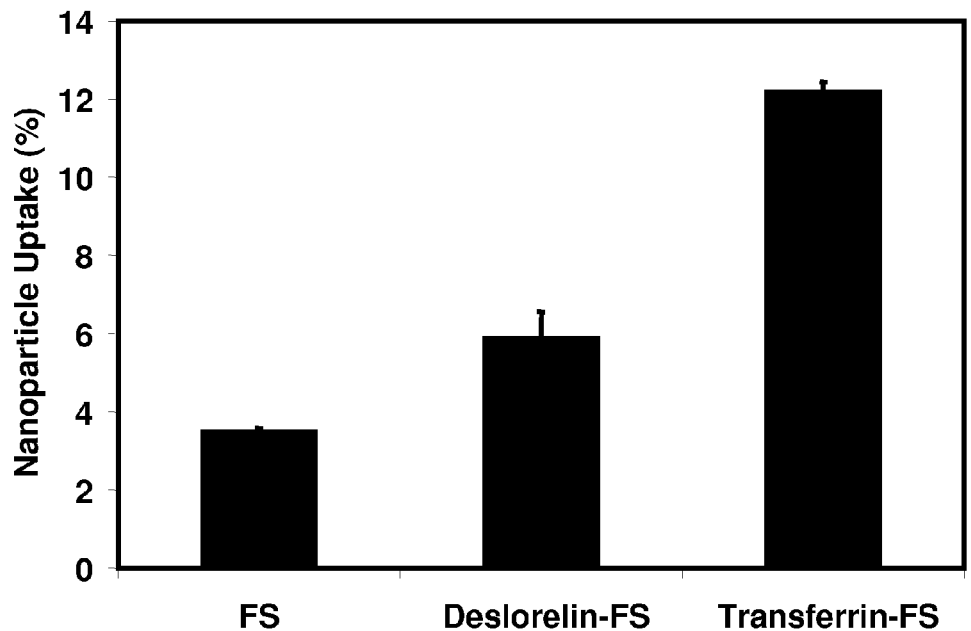
FIGS. 37 and 38 illustrate the uptake of non-biodegradable and biodegradable, respectively, nanoparticles in human retinal pigment epithelial cells (ARPE-19).
Figure 38:
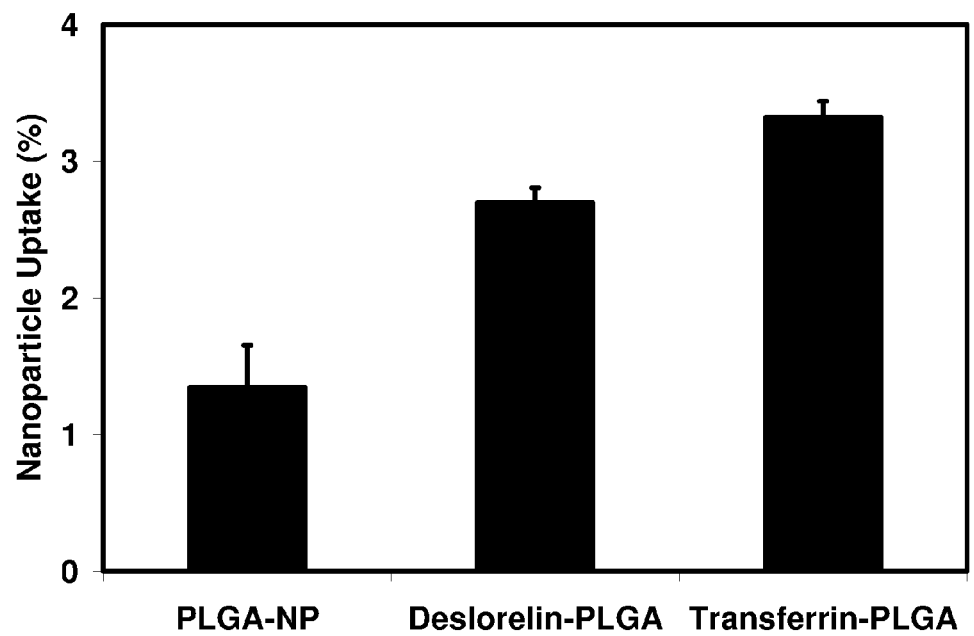
Figure 39:
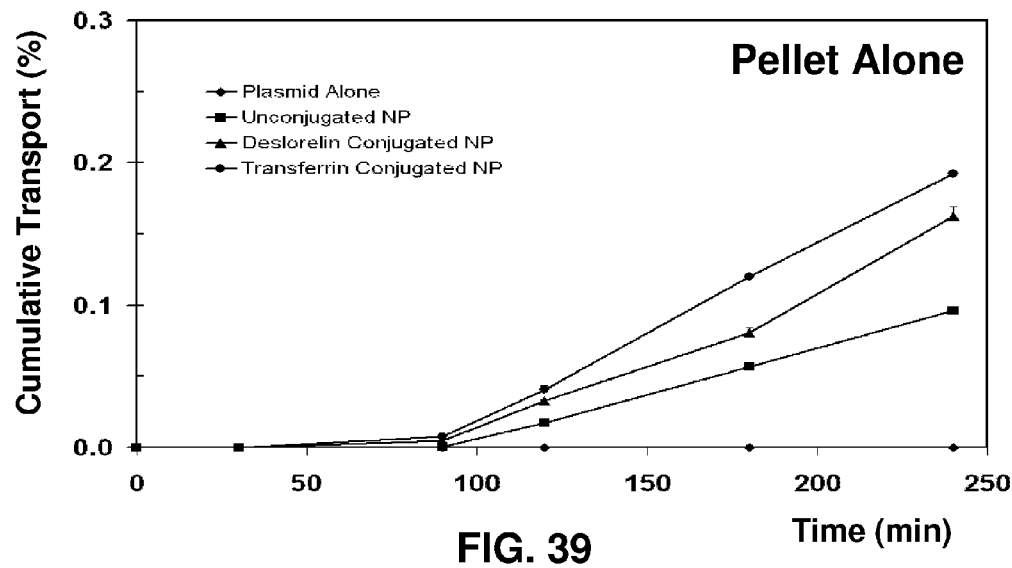
FIGS. 39 and 40 depict the results of transport studies comparing the cumulative transport of unconjugated nanoparticles with targeted nanoparticles and plasmid alone, using the pellet (FIG. 39) or supernatant (FIG. 40) from the studies.
Figure 40:
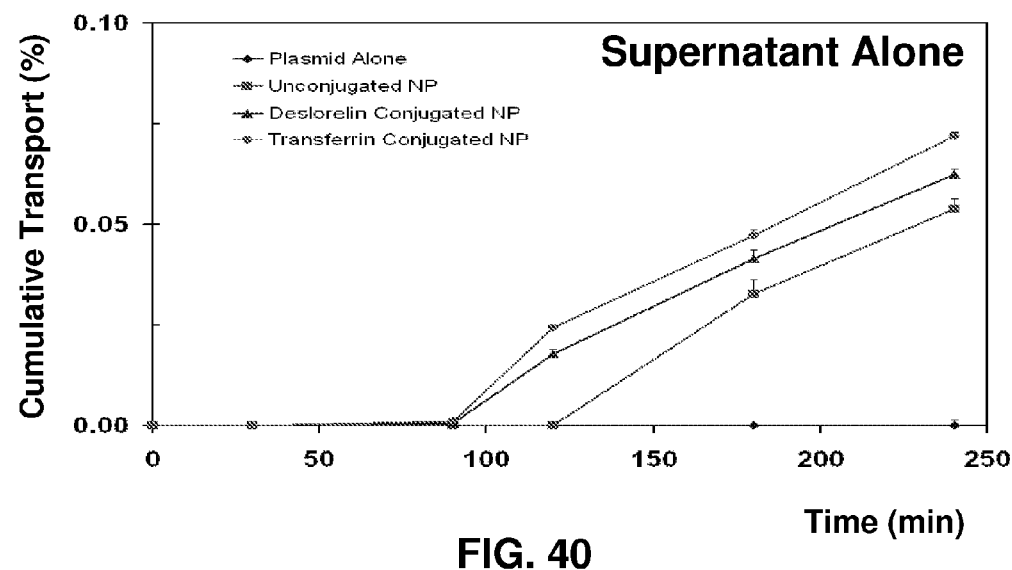
Figure 41:
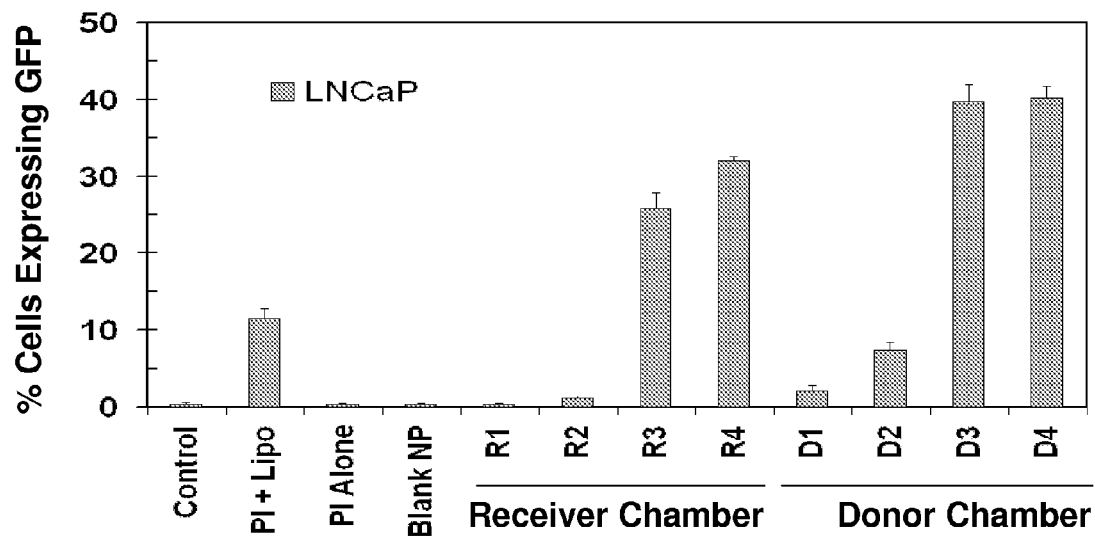
FIGS. 41 and 42 are charts comparing the transfection efficiencies of unconjugated nanoparticles with targeted nanoparticles and plasmid alone, in LNCaP (FIG. 41) and PC-3 (FIG. 42) prostate cancer cell lines.
Figure 42:
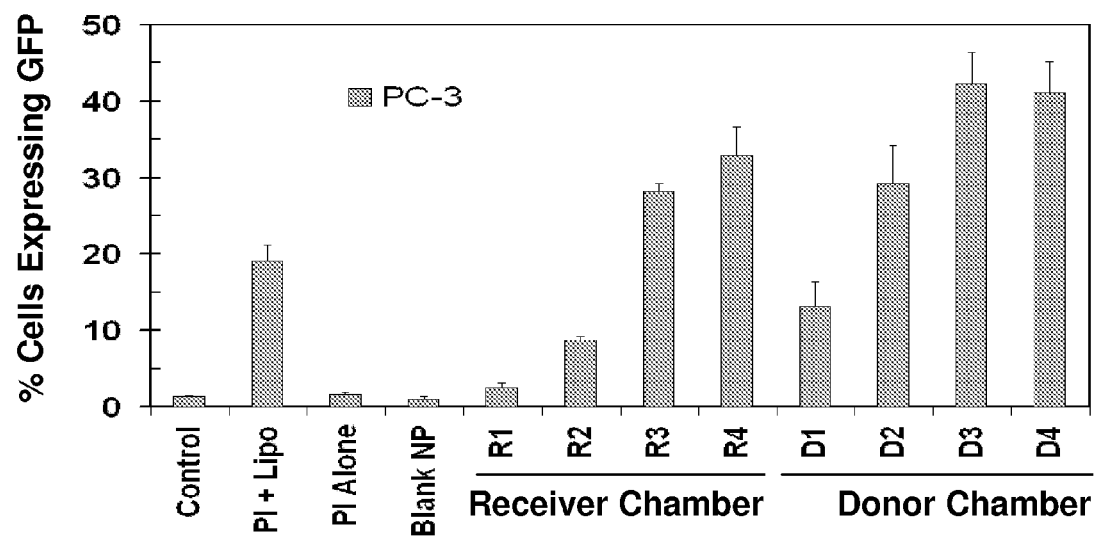

Results indicated that conjugation to a targeting moiety increases nanoparticle uptake by human retinal pigment epithelial cell line. The percentage uptake of deslorelin or transferrin targeted nanoparticles into ARPE-19 cells was significantly higher compared to unconjugated (untargeted) nanoparticles. Specifically, percentage uptake at 3 h by ARPE-19 cells of nonbiodegradable FluoSpheres®, deslorelin-targeted FluoSpheres® and transferrin-targeted Fluo- Spheres® was 3.48±0.08, 5.88±0.67, and 12.2±0.26, respectively (FIG. 37). Similarly, percentage uptake for biodegradable PLGA particles, deslorelin-targeted PLGA particles, and transferrin-targeted PLGA particles was found to be 1.34±0.3, 2.69±0.1, and 3.32±0.1, respectively (FIG. 38). Thus, targeting nanoparticles with deslorelin, an LHRH-receptor-targeting moiety, causes a 2 fold increase in percentage uptake of nanoparticles by ARPE-19 cells and thereby can be employed to enhance delivery of nanoparticles to posterior segment of the eye.

Example 11

Assay for LHRH Receptor mRNA Expression in Bronchial & Nasal Tissue

The expression of LHRH receptor (LHRH-R) was determined in human bronchial epithelium (Calu-3 cells, ATCC No. HTB-55, Manassas, Va.), bovine nasal, rat trachea, and rat lungs using reverse-transcriptase polymerase chain reaction (RT-PCR). Calu-3 cells were maintained free of mycoplasma in culture at 37° C., 5% $CO_2$, and 95% $O_2$ in Minimum Essential Medium with 10% fetal bovine serum (Life Technologies, Grand Island, N.Y.) supplemented with non-essential amino acids, 1% sodium pyruvate, 2% L-glutamine, and 100 U/ml penicillin G and 100 μg/ml streptomycin sulfate (Life Technologies). Cells were plated in 75 $cm^2$ cell culture flasks (Corning Corp., Corning, N.Y.) and subcultured at 90% confluence using a 0.25% trypsin/0.1% EDTA in maintenance medium. The culture medium was changed every two days and cells were split 1:2 during each passage. Cells of passages 25-36 were used in the study. Cell culture materials and reagents were obtained from Gibco (Grand Island, N.Y.) and Becton Dickinson Labware (Franklin Lakes, N.J.).

Excised tissues were assessed in order to ensure the expression of LHRH-receptor in normal tissues. Bovine nasal mucosa was obtained from freshly slaughtered cattle at the local slaughterhouse (J&J Meats, Elkhorn, Nebr.). The nasal tissue was isolated and prepared for experiments as described by Schmidt et al. (2000) J. Pharm. Sci. 89:396-407. The skin covering the nose was removed, and the frontal part of the nasal conchae was dissected. The mucosal tissue was then carefully stripped from the cartilage using a pair of tweezers and used for expression studies. LHRH-receptor expression was assessed in the medium turbinate posterior (beyond 2.5 inches past the tip of nares) region of the bovine nose. In case of rat tissues, following euthanization, an incision was made at the level of the esophagus, and the lung lobes were isolated along with the trachea. The trachea representative of upper airways, and lung lobes representative of lower respiratory tract, were used for expression studies.

Following total RNA isolation using RNA STAT-60 RNA isolation kit (TEL-TEST, Friendswood, Tex.), RT-PCR was performed with an Access RT-PCR system (Promega, Madison, Wis.). RT-PCR for LHRH-receptors and 18s rRNA (internal control) was performed in a standard 50 μl reaction mixture containing 0.2 mM deoxytriphosphate nucleotides, 2 mM $MgCl_2$, 20 μmol each of sense and antisense primers, 5 U of Tfl DNA polymerase, and 5 U of avian myeloblastosis virus (AMV) reverse transcriptase. The amplification of the cDNA was performed as described by Halmos et al. (2000) J. Urology 163:623-629. The amplified products were separated on a 1.5% agarose gel and visualized by staining with ethidium bromide and were subjected to DNA sequencing. The primers used were forward 5'-GACCTTGTCTGGAAA-GATCC-3' (SEQ ID NO: 10) and reverse 5'-CAGGCTGAT-CACCACCATCA-3' (SEQ ID NO: 3). Densitometric analysis for LHRH-receptor mRNA expression was performed using Nucleovision Imaging System (Nucleotech, San Mateo, Calif.). The amplified products were then isolated and sequenced to confirm the identity (University of Nebraska DNA sequencing facility, Omaha, Nebr.). A Blast sequence search revealed that the observed band corresponded to a mammalian LHRH-receptor.

Figure 29:
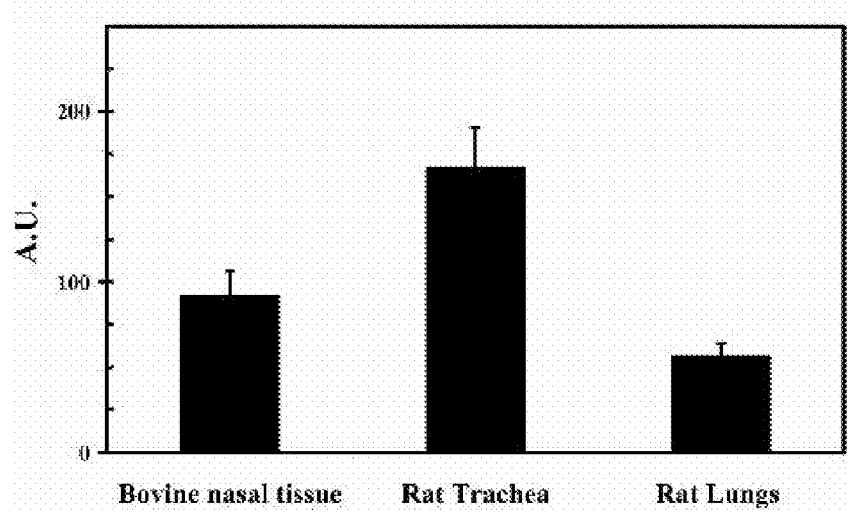
FIG. 29 depicts the expression (mRNA) levels of receptors for LHRH and GAPDH in bovine nasal tissue, rat trachea, and rat lungs.

As shown in FIG. 29, LHRH-receptor is expressed in bovine nasal tissue, rat trachea, and rat lungs. LHRH-receptor distribution was examined in Calu-3 cells using immunofluorescent staining by a monoclonal antibody against LHRH-receptor and a CY3 tagged goat anti-mouse antibody. For confocal microscopy, Calu-3 cells were grown on 6-well clear polyester Transwells (0.4 μm pore size; Costar, Corning, N.Y.) for improved microscopic visualization. On day 10, after removing the medium, cells were washed with PBS (137 mM NaCl, 2.7 mM KCl, 1.4 mM $NaH_2PO_4$, 4.3 mM $Na_2HPO_4$, pH 7.4) and fixed during a 15 minute incubation at room temperature (Histochoice; Sigma). The fixed cells were washed again and permeabilized with 0.1% Triton-X 100 followed by blocking of nonspecific binding sites for 1 hour (1% w/v goat serum in PBS). Following this, cells were incubated for another 1 hour at room temperature with a 1 μg/ml solution of primary LHRH-receptor antibody (GnRH-R Ab03, LabVision Corp., Fremont, Calif.), washed, and incubated with a secondary antibody conjugated with CY3 (Molecular Probes, Eugene, Oreg.). Images of LHRH-receptor immunostained cells were acquired under an oil immersion objective (X63) with a confocal laser microscope (Zeiss Confocal LSM410, Carl Zeiss MicroImaging, Thornwood, N.Y.) equipped with an argon-krypton laser. Negative controls were prepared similarly except that an isotypic IgG1 (Southern Biotechnology Associates, Birmingham, Ala.) was used instead of the primary LHRH-receptor antibody.

Figure 30:
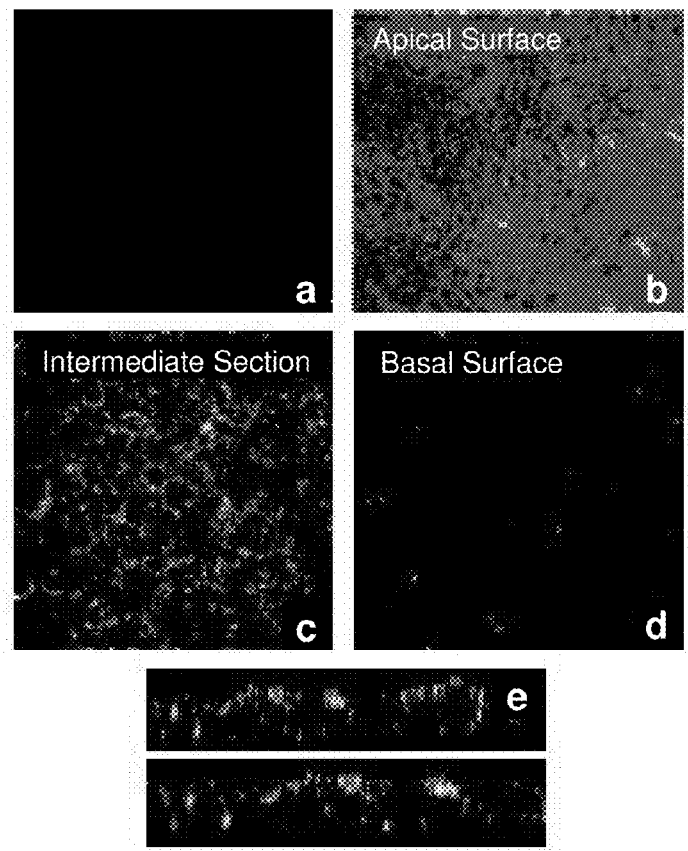
FIG. 30 is a confocal image of immunostaining for LHRH receptors in human airway epithelial cells (Calu-3).

There was no red fluorescence in the negative controls (FIG. 30, panel A). However in cells incubated with the primary antibody, there was a clear red staining pattern and the intensity of staining was strongest at the apical membrane and minimal at the basal membrane, indicating the predominance of LHRH-receptors in the apical and lateral membranes of Calu-3 cells (FIG. 30, panels B through D). No fluorescent endocytotic vesicles at the level of plasma lemma or within the cells could be observed in these sections possibly because the relative number of receptors endocytosed at any point of time may be very less compared to those present on the membrane, thereby making their visualization difficult. Also, the cross section of the monolayers indicated a strong signal along the apical membrane (FIG. 30, panel E).

Example 12

Western Blot Assay for LHRH Receptors in Bronchial & Nasal Tissue

The expression of LHRH receptor (LHRH-R) in human bronchial epithelium, bovine nasal, rat trachea, and rat lungs was assayed by Western blot. Cell monolayers of human bronchial epithelium (Calu-3) were solubilized in phosphate-buffered saline (pH 7.4) containing protease inhibitors (Boehringer Mannheim, Indianapolis, Ind.) and 1% sodium dodecyl sulfate (SDS), and the total protein content of each of the cell lysates was estimated. For separation, lysate samples (50 μg) were loaded onto preformed 10% polyacrylamide gels (Bio-rad, Hercules, Calif.). Cell lysates of prostate cancer carcinoma cell line, LnCap, loaded at 30 μg were used as positive controls. Molecular weight markers ranging from 220 to 14.3 kDa (Amersham Life Science, Arlington Heights, Ill.) were used to identify the LHRH-receptor and β-actin protein bands. The proteins on the gels were separated using SDS-polyacrylamide gel electrophoresis (SDS-PAGE). The gels were run at 60 V for 10 minutes and then continued at 120 V for another 1.5 hours.

Figure 31:
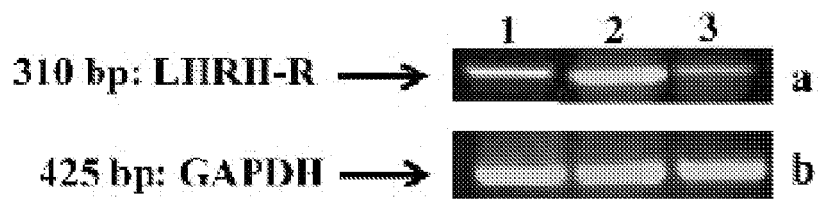
FIG. 31 is a Western blot assay to detect the presence of receptors for LHRH and GAPDH in bovine nasal tissue (lane 1), rat trachea (lane 2) and rat lungs (lane 3).

The proteins were then transferred onto the polyvinylidene fluoride (PVDF) membranes (Millipore, Bedford, Mass.) at 4° C. using a 480 mA current. The immunoblots were done using the LHRH-receptor specific monoclonal antibody GnRHAb-3 (Neomarkers, LabVision, CA) or the monoclonal β-actin antibody (Sigma, St. Louis, Mo.). The transferred proteins were treated with the blocking buffer, which contained 0.3% Tween-20 and 1% BSA and incubated with the specific antibodies overnight at 4° C. for 1 hour. LHRH-receptor bands were visualized using a chemiluminescence kit. As shown in FIG. 31, Western blot analysis indicated the presence of LHRH-R protein in bovine nasal tissue (lane 1), rat trachea (lane 2) and rat lungs (lane 3).

Example 13

Transport Studies in Bovine Nasal Tissue

Transport studies were conducted in bovine nasal tissue. We observed that deslorelin transport across excised bovine nasal tissue exhibited regional variation. To investigate whether this regional variation is due to differences in passive transport, we assessed the transport of sodium fluorescein, a polar solute transported primarily by the paracellular route through the tight junctions between the cells. Consistent with its predominantly passive diffusion in nasal tissue, the fluorescein transport did not exhibit vectorial transport. However, it exhibited regional variability in transport similar to s-m transport of deslorelin. This suggested that at least part of the regional variation observed with deslorelin could be due to differences in paracellular permeability of deslorelin. Another reason for the difference in transport could be the differences in metabolism of deslorelin in the different regions of the nasal tissue. A detailed description of the studies follows.

Bovine nasal tissue was obtained from freshly slaughtered cattle at the local slaughterhouse (J & J Meats, Elkhorn, Nebr.). The nasal tissue was isolated and prepared for experiments as described by Schmidt et al. (2000) J. Pharm. Sci. 89:396-407. The skin covering the nose was removed, and the frontal part of the nasal conchae was dissected. The mucosal tissue was then carefully stripped from the cartilage using a pair of tweezers and immediately used for experiments. Tissues used for experiments typically had an area of 3-4 $cm^2$. Different regions of the bovine nasal tissue, including the medium turbinate anterior (MTA) (up to 2.5 inches from the frontal tip of nares), the medium turbinate posterior (MTP) (beyond 2.5 inches past the tip of nares) and the inferior turbinate posterior (ITP) (beyond 2.5 inches past the tip of nares, below the MTP region and facing the floor of the nasal cavity, i.e., the inferior maetus) regions, were used for the transport studies.

Modified Ussing chambers (Navicyte, Reno, Nev.) were used to mount the nasal tissue for permeation studies. The tissue was exposed to 1.5 ml of assay buffer with drug on one side (donor side) and assay buffer without the drug on the other side (receiver side). The fluid volume was 1.5 ml on each side and the exposed tissue area was 0.64 $cm^2$. In this study, transport studies were conducted in both mucosal-to-serosal (m-s) and serosal-to-mucosal (s-m) directions. The chambers were maintained at a constant temperature (37° C. or 4° C.) with an external circulating water bath. Gas-flow controllers and air manifolds were used to ensure constant gas flow (5% $CO_2$/20% $O_2$/75% $N_2$) into the tissue bathing fluids. The mucosae were initially equilibrated with pre-warmed assay buffer for 15 minutes. Following this, the solution from donor chambers (mucosal and serosal for m-s and s-m transport studies, respectively) was aspirated and immediately replaced with deslorelin or fluorescein solutions and buffer was added to the receiver chamber. Samples (250 μL) were collected from the receiver chamber at various intervals up to 6 h and replaced with pre-warmed buffer. Deslorelin and fluorescein transport in both directions was assessed at 37° C. and 4° C. Also, the effect of 2,4-dinitrophenol was determined on directional transport of deslorelin and fluorescein at 37° C. In these studies, 2,4-dinitrophenol (100 μm) was added only to the donor chamber. That is, for m-s transport studies, 2,4-dinitrophenol was added to the mucosal side and for the s-m transport studies, it was added to the serosal side. The samples were placed in polypropylene tubes, capped and stored at −20° C. until analysis. Samples of the same volume were also taken from the peptide-containing solution.

The apparent permeability coefficient ($P_{app}$) was calculated using the equation: $P_{app}=(dM/dt)/(A*C_d)$. dM/dt is the slope of the cumulative amount of deslorelin transported vs time, A is the area (0.64 $cm^2$) available for transport and $C_d$ is the initial donor drug concentration. Permeation data were corrected for dilution of the receiver solution with sample volume replenishment.

Fluorescein transport across excised bovine nasal tissue was analysed and quantified using a spectrofluorometer (Shimadzu, RF 5000 U). An excitation wavelength of 488 nm and an emission wavelength of 510 nm was used. Band widths of 3 or 5 nm were used for the analysis of samples after dilution, as required. The deslorelin transported was quantified by high performance liquid chromatography using a Waters HPLC system comprising of a Waters 600 S controller, Waters TM 616 solvent delivery pump and a Waters 717 plus auto injector. The deslorelin was detected using a Waters 996 PDA detector set at a wavelength of 220 nm or a Waters 474 scanning fluorescence detector with an excitation of 280 nm and an emission of 350 nm and the peak areas were integrated using Millennium software (version 2.15.01). The mobile phase consisted of 30% acetonitrile and 70% of 0.1% TFA in distilled water delivered at a rate of 1 ml $min^{-1}$. A microsorb C-18 column (250×4 mm) with a particle diameter of 5 μm and a pore size of 100 A from Rainin Instruments (Emeryville, Calif.) was used.

Unless otherwise stated, each experiment was carried out in triplicate using tissues from different animals. Data in all cases are expressed as mean±standard deviation. Comparison of mean values between the different treatments was carried out using two-way analysis of variance followed by Tukey's post-hoc analysis using SPSS (version 8.0) software. The level of significance was set at $P<0.05$.

Figure 32:
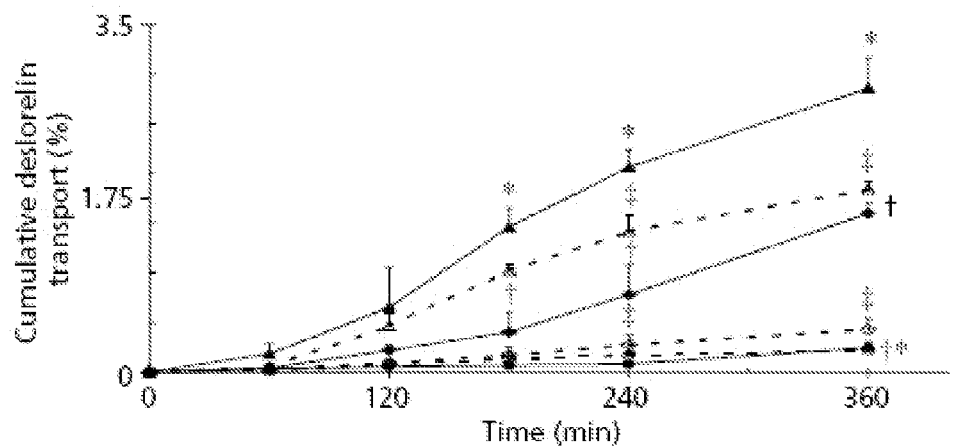
FIGS. 32 and 33 illustrate the cumulative deslorelin transport across various nasal tissues in bovine transport studies over time (FIG. 32), and comparatively (FIG. 33).

Results indicated that deslorelin transport across excised bovine nasal tissue exhibits regional variation and directionality. The transport of deslorelin (1 $mgmL^{-1}$) across medium turbinate anterior (MTA), medium turbinate posterior (MTP) and inferior turbinate posterior (ITP) regions of the excised bovine nasal tissue was assessed in the mucosal-to-serosal (m-s) and serosal-to-mucosal (s-m) directions. The cumulative m-s transport of deslorelin at the end of 6 hours was in the order MTA<MTP<ITP (FIG. 32). Also, the s-m transport exhibited a similar trend. FIG. 32 depicts the time course of deslorelin transport in the mucosal-to-serosal (solid lines; filled symbols) and serosal-to-mucosal (broken lines; open symbols) directions across medium turbinate anterior (MTA)

(circles), medium turbinate posterior (MTP) (diamonds) and inferior turbinate posterior (ITP) (triangles) regions of excised bovine tissue.

Figure 33:
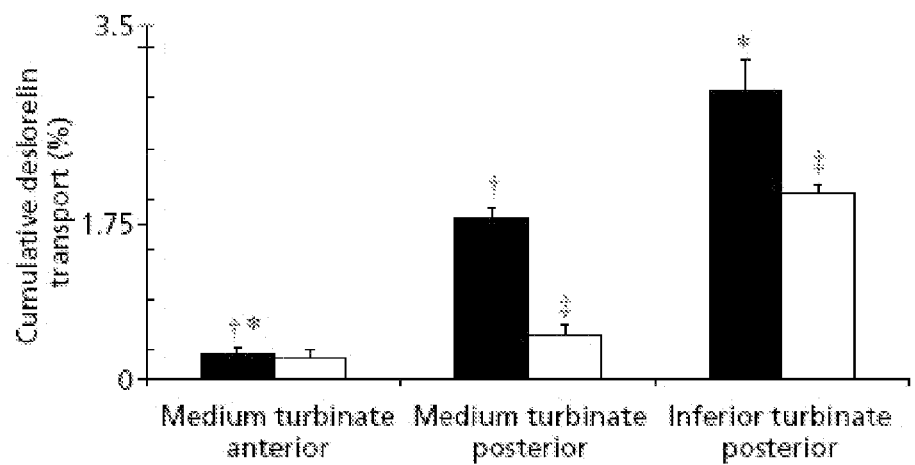
Figure 34:
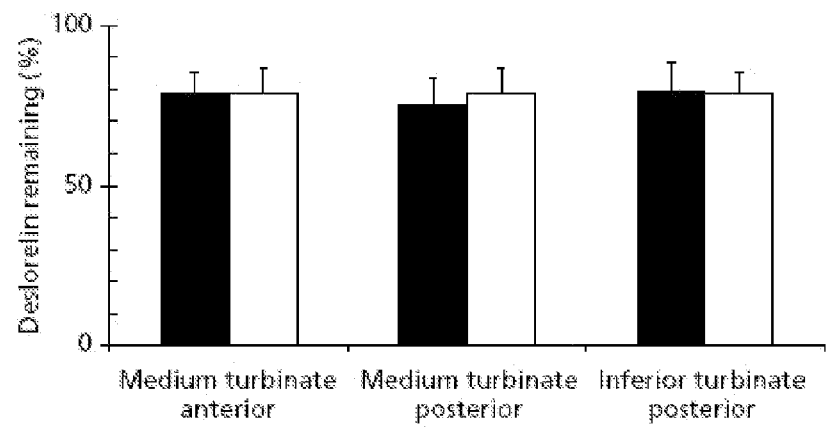
FIG. 34 depicts the percentage remaining deslorelin the donor chamber at the end of the studies.

Furthermore the deslorelin transport was vectorial (FIG. 33) with the m-s:s-m transport ratios being in the order MTA<ITP<MTP (Table 7). FIG. 33 illustrates the percent cumulative deslorelin transported at the end of 6 h across MTA, MTP and ITP regions in the mucosal-to-serosal (closed bars) and serosal-to-mucosal (open bars) directions. The MTP region, which exhibited the highest m-s:s-m ratio, was further evaluated for the temperature and energy dependence of deslorelin transport. The percentage of deslorelin remaining in the mucosal chamber at the end of 6 h was not significantly different and was 78.8±6.8, 74.87±8.4 and 79.3±8.9% for MTA, MTP and ITP, respectively (FIG. 34). Also, no difference was observed between mucosal and serosal donor concentrations. FIG. 34 illustrates the percentage of deslorelin remaining in donor chamber at the end of 6 h of transport across MTA, MTP and ITP regions in the mucosal-to-serosal (closed bars) and serosal-to-mucosal (open bars) directions. For FIGS. 32-34, data are expressed as mean±standard deviation, n=4-6 animals. The asterisk indicates a P<0.05 compared with MTP; the cross indicates a P<0.05 compared with ITP, and the double cross indicates a P<0.05 compared with mucosal-to-serosal transport in the same region.

Figure 35:
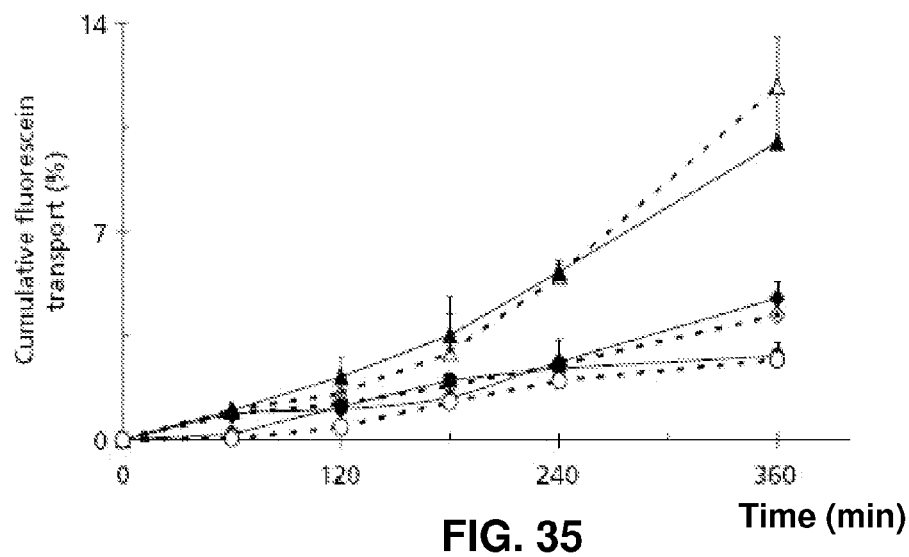
FIGS. 35 and 36 illustrate the cumulative transport of unconjugated nanoparticles across various nasal tissues in bovine transport studies over time (FIG. 35), and comparatively (FIG. 36).
Figure 36:
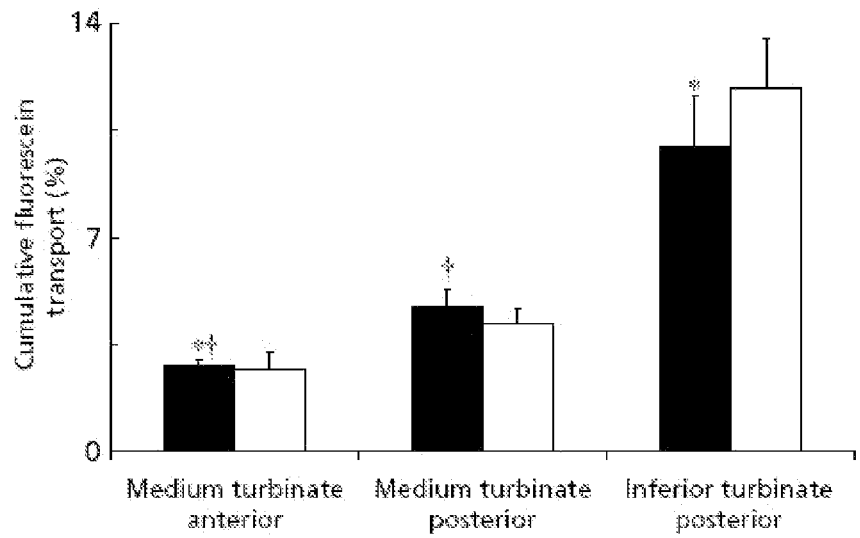

Fluorescein transport across bovine nasal tissue exhibits regional variation but no directionality. The transport of sodium fluorescein, a hydrophilic solute that is predominantly or solely transported via the paracellular route, was assessed across the MTA, MTP and ITP regions of bovine nasal mucosa. The % cumulative sodium fluorescein transport was different across different regions and was in the order: MTA (2.8±0.1%)<MTP (4.2±0.5%)<ITP (9.9±1.6%) (FIG. 35). FIG. 35 illustrates the time course of fluorescein transport in the mucosal-to-serosal (solid lines; filled symbols) and serosal-to-mucosal (broken lines; open symbols) directions across medium turbinate anterior (MTA) (circles), medium turbinate posterior (MTP) (diamonds), and inferior turbinate posterior (ITP) (triangles) regions of excised bovine tissue. However, the transport was not vectorial (FIG. 36) and the m-s:s-m ratios were 1.12±0.27, 1.27±0.18 and 0.89±0.16 for the MTA, MTP and ITP regions, respectively (Table 7). FIG. 36 depicts the percent cumulative fluorescein transported at the end of 6 hours across MTA, MTP and ITP regions in the mucosal-to-serosal (closed bars) and serosal-to-mucosal (open bars) directions. Data are expressed as mean±standard deviation, n=3 animals. The asterisk indicates a P<0.05 compared with MTP; the cross indicates a P<0.05 compared with ITP, and the double cross indicates a P<0.05 compared with mucosal-to-serosal transport in the same region.

TABLE 7

Comparison of m-s:s-m Ratios of Cumulative Transport

| Region | Medium Turbinate Anterior | Medium Turbinate Posterior | Inferior Turbinate Posterior |
|---|---|---|---|
| Deslorelin | 1.5 ± 0.234‡ | 5.4 ± 0.67* | 3.72 ± 0.72*‡ |
| Fluorescein | 1.12 ± 0.27 | 1.27 ± 0.18 | 0.89 ± 0.16 |

Key:
data are expressed as mean ± standard deviation, n = 3 animals.
The asterisk indicates a P < 0.05 compared with fluorescein for the same region;
the cross indicates a P < 0.05 compared with medium turbinate posterior region.

Example 14

Preparation and Characterization of PLGA Carrier Particles with Therapeutic Plasmid PLGA nanoparticles were prepared and loaded with Flt23k plasmid as follows. Nanoparticles were formulated using a double emulsion solvent evaporation method, following which the residual solvent was evaporated using a Rotary evaporation method. Particle size and zeta potential of the nanoparticles was estimated using dynamic light scattering (Brookhaven). Nanoparticles were harvested and lyophilized for conjugation with deslorelin and transferrin. Plasmid loading in the nanoparticles was estimated following lyophilization using an extraction method and estimated using UV spectrophotometry.

Carrier particles were prepared using a double emulsion solvent evaporation method. Resomer 503H (PLGA 50:50; i.v. 0.44 dl/g; Boehringer Ingelheim, Petersburg, Va.) (150 mg) COOH modified and Flt23k plasmid (500 µl of 1 mg/ml). Briefly, plasmid in TE buffer (500 µl) was poured into organic phase (PLGA dissolved in 1 ml dichloromethane) and sonicated using a probe sonicator at 10 W for 1 min to form the primary emulsion. Following sonication, the emulsion was poured into 8 ml of 2% PVA and sonicated at 30 W for 3 min. Following sonication the double emulsion was poured into 40 ml of 2% PVA and solvent was allowed to evaporate at moderate stirring at speed 7000 rpm on Magnetic stirrer (Fisher Scientific, Pittsburgh, Pa.) overnight at room temperature. The suspension was further evaporated using a Rotovap (Buchi Rotavapor R200, Buchi Analytical Inc., New Castle, Del.) for 2 hours at 40° C. in a heated water bath (Buchi Heat Bath B490) to remove residual solvent. Following evaporation the suspension was centrifuged at ~30000 g for 50 min at 4° C. The particle pellet was resuspended in double distilled water (20 ml; repeated twice to remove surface bound PVA and plasmid) and lyophilized. Blank particles without the plasmid were prepared as controls following the above procedure.

Conjugation with deslorelin and transferrin: 20 mg of nanoparticles were resuspended in 10 ml of MOPS buffer (pH 6.5) and incubated at room temperature for 2 hours. Following incubation, 10 ml of 200 µg/ml protein solution was added dropwise to the particle suspension and incubated at room temperature for 12 hours. The reaction was stopped using 100 µl of 100 mM glycine solution. The conjugated nanoparticles were harvested by centrifugation at 35000 g for 50 min. The particle pellet was resuspended in double distilled water (20 ml) and lyophilized.

Particle Size Analysis: Particle size and zeta-potential of the nanoparticles before and after conjugation following lyophilization were measured in double distilled water (100 µl of particle/1 ml of water) using dynamic light scattering (DLS). After lyophilization the plasmid loaded particles were weighed (1 mg) into glass Kimble tubes. To each tube, 1 ml of double distilled water was added and vortexed at high speed (Vortex Genie, Scientific Industries, Bohemia, N.Y.) till the particles were resuspended. The particle size and zeta potential was determined using dynamic light scattering after dilution (1:10 in double distilled water) (Brookhaven Instruments Corp., Holtsville, N.Y.). Nanoparticle size after lyophilization was 210.4±0.68 nm and zeta potential was −32.85±0.87 mV. Nanoparticle size and zeta potential was measured after conjugation with deslorelin and transferrin. Similarly, the unconjugated nanoparticles were also treated under the same conditions as with the conjugated nanoparticles (the conjugation protocol as mentioned above).

TABLE 8

Physical Properties of Various Nanoparticles

| Parameters | After Lyophilization | Unconjugated | Deslorelin Conjugated | Transferrin Conjugated |
|---|---|---|---|---|
| Particle size (nm) | 210.4 ± 0.68 nm | 217.98 ± 0.78 | 203.89 ± 0.76 | 207.45 ± 0.91 |
| PDI | 0.097 ± 0.012 | 0.087 ± 0.011 | 0.043 ± 0.012 | 0.087 ± 0.014 |
| Zeta potential (mV) | −32.85 ± 0.87 | −23.89 ± 0.99 | −24.87 ± 0.78 | −23.87 ± 0.67 |
| Distribution | Unimodal | Unimodal | Unimodal | Unimodal |
| Loading | 2.09% | | | |

Plasmid Loading: Lyophilized plasmid loaded PLGA particles were weighed (1 mg) into glass Kimble tubes. To each tube, 1 ml of methylene chloride was added and sealed. The tubes were vortexed at high speed (Vortex Genie, Scientific Industries, Bohemia, N.Y.) at 10 on the scale of speed. After 1 hour of vortexing, 1 ml of water was added to the organic phase with further vortexing for 30 min. At the end of 30 min the mixture was allowed to settle down to separate organic and aqueous phase. The aqueous phase was collected into the quartz UV cuvette (with appropriate dilution) and analyzed using UV spectrophotometry. Similarly, the standard curves were prepared by extraction of plasmid from known amounts of plasmid and polymer (6 mg and 14 mg, respectively) followed by serial dilution.

Example 15

Transport and Transfection Studies Using PLGA Carrier Particles with Therapeutic Plasmid in Bovine Nasal Tissue Transport studies were performed in bovine nasal tissue to determine whether Flt23k plasmid loaded PLGA nanoparticles enhance plasmid transport across the bovine nasal tissues, and to determine the efficacy of ocular targeting moieties (deslorelin and transferrin) in enhancing plasmid transport. Transport and uptake was highest across the bovine ITP region, hence the transport studies were carried out across the ITP region in this study. Further, the transport across bovine nasal ITP region was in the order: transferrin moiety-targeted carrier particle>deslorelin moiety-targeted carrier particle>unconjugated carrier particle>plasmid alone. PLGA carrier nanoparticles loaded with Flt23k plasmid and targeted with ocular targeting moieties were prepared according to the preceding Example. The nanoparticle had a narrow size distribution with mean particle size of 250.4±0.68 nm and zeta potential of −32.85±0.87 mV.

Nanoparticle Transport Studies: Modified Ussing's chambers (Navicyte, Reno, Nev.) were used to mount the ITP region of bovine nasal tissue for permeability studies. The tissues were exposed to 5 ml of assay buffer with either plasmid alone or plasmid-loaded nanoparticles (conjugated and unconjugated) on the donor side (mucosal surface). Assay buffer without particles was exposed to the receiver side (serosal surface). The buffers used were pre-equilibrated to 37° C. The donor plasmid and nanoparticle concentration was 100 µg/ml and 500 µg/ml respectively. The chambers were maintained at 37° C. with an external circulating water bath. Samples (500 µl) were collected from the receiver chamber at various intervals up to 4 hours and replaced with equivalent amount of assay buffer. Donor samples were collected at the end of the experiment. The samples were collected in polypropylene tubes, capped, and stored at 4° C. until analysis. The aperture/tissue area exposed to the bathing fluids in this set up was 1.78 $cm^2$. The samples were centrifuged at 6000 g to separate the nanoparticles from the plasmid released during transport. Following centrifugation the pellet was subjected to the extraction process similar to the plasmid loading method as mentioned above.

Receiver (various time points) and donor chamber samples (at 4 hour) (5001) were collected. The samples were centrifuged at 6000 g for 30 min twice to separate the nanoparticles from the released plasmid. Following centrifugation the supernatant was collected and the pellet was dissolved in 200 µl of dichloromethane. The tubes were vortexed at room temperature for 2 hours following which the plasmid was extracted using TE buffer. The aqueous phase was collected into another Eppendorf tube. The samples were estimated for plasmid content using a fluorescent Pico green assay. The plasmid content in the pellet was higher as compared with the plasmid content in the supernatant. However, the plasmid alone samples were not detected in the supernatant samples alone, but when the samples from the pellet and supernatant were combined the plasmid transport was approximately 0.03% at 4 hours. Further, plasmid transport was in the order transferrin moiety-targeted carrier particle>deslorelin moiety-targeted carrier particle>unconjugated carrier particle>plasmid alone, as shown in FIGS. 39-40.

Transfection studies: The donor and receiver chamber samples (4.5 ml) were collected at the end of the four hour transport study. The samples were lyophilized and resuspended in serum free medium. 500 µl of the medium was added to the cells, and incubated for 24 hours, following which the medium was removed and fresh serum containing medium was added. After 24 hours incubation, the medium was collected (for VEGF studies) and the cells were harvested with trypsin-EDTA. The trypsin was neutralized with serum containing medium followed by centrifugation at 3000 rpm for 10 min. The cells were resuspended in 500 µl of PBS buffer at pH 7.4 and analyzed for GFP expression using flow cytometry using excitation and emission wavelengths of 488 nm and 510 nm respectively. Receiver and donor chamber samples collected after transport and lyophilized were used for transfection of prostate cancer cell lines: LNCaP and PC-3. Controls used for the study included: Control (no treatment), plasmid+lipofectamine, plasmid alone and blank carrier nanoparticles (no plasmid; no conjugation). The treatment was carried out for 12 hours in serum free media followed by further 12 hours incubation in serum containing media to allow for protein expression. The GFP expression was measured by flow cytometry as the percentage of cells expressing the GFP protein.

As shown in FIGS. 41 and 42, the GFP expression (R1 and D1) following receiver and donor chamber samples was in the order: transferrin moiety-targeted carrier particle (R4 and D4)>deslorelin moiety-targeted carrier particle (R3 and D3)>unconjugated carrier particle>plasmid alone (R2 and D2). Further, donor chamber samples showed higher transfection than receiver chamber samples. This could be due to the concentration of plasmid and nanoparticles in the donor chamber being higher compared with the concentration in the receiver chamber. However, the plasmid alone treated groups were less effective than the plasmid+lipofectamine groups, indicating that plasmids alone are not effectively taken up by the cells. Similarly, the unconjugated particle group also exhibited significantly lower transfection compared with the plasmid+lipofectamine group indicating that the targeting of the carrier particles with the ocular targeting moieties (deslorelin and transferrin) was effective in increasing the transfection efficiencies on cells.

VEGF studies: LNCaP and PC-3 cells were cultured in RPMI-1640 medium containing 10% fetal bovine serum, 100 U/mL penicillin, 100 mg/mL streptomycin, and 2 mM L-glutamine. The medium was changed every 3 days, and all studies were conducted with 60-70% confluent cells. VEGF secretion studies in LNCaP and PC-3 cells were performed on the medium collected after 24 hours incubation of the cells in the above study. Briefly, the manufacturer's protocol was followed for VEGF ELISA (Research Diagnostics Inc, Concord, Mass.). The kit is capable of detecting the secreted human VEGF isoforms VEGF165 and VEGF121. The kit has no cross-reactivity with recombinant human VEGF-B196. Following primary antibody coating, the 96 well plate was blocked with blocking solution. The samples were then plated on to the plate followed by incubation with secondary antibody. The binding was detected by poly-HRP streptavidin and biotin reaction using an ELISA plate reader at 450 and 550 nm.

Figure 43:
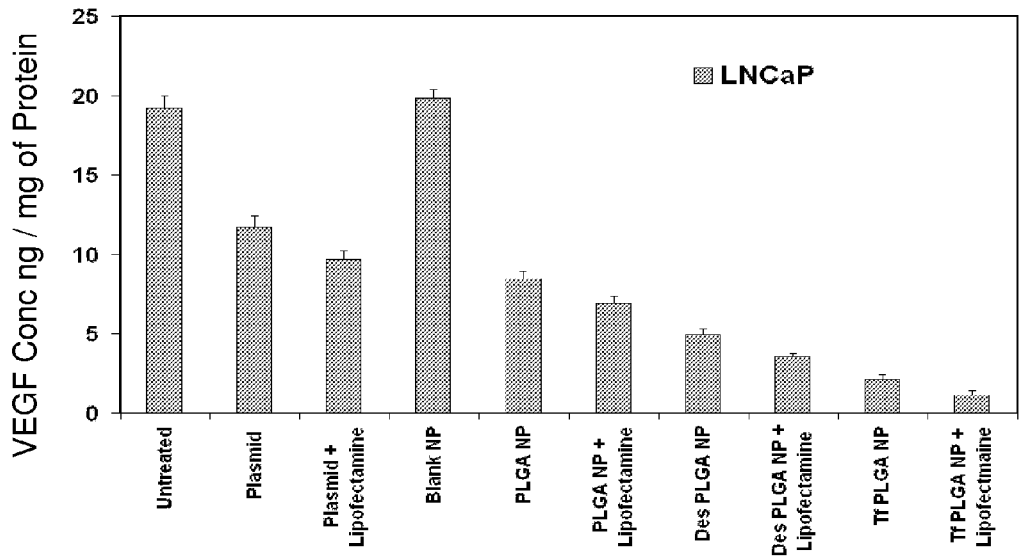
FIGS. 43-45 are charts comparing the VEGF secretion after treatment with PLGA nanoparticles loaded with Flt23k plasmid in prostate cancer cells following treatment with or without lipofectamine (FIG. 43), or transport across bovine nasal ITP region (FIG. 44: LNCaP cells.
Figure 44:
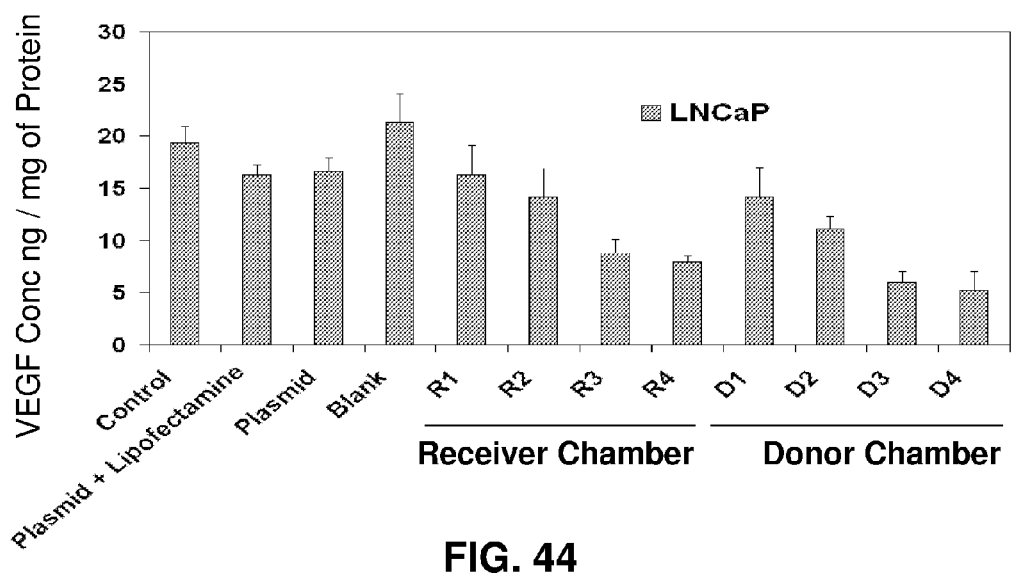
Figure 45:
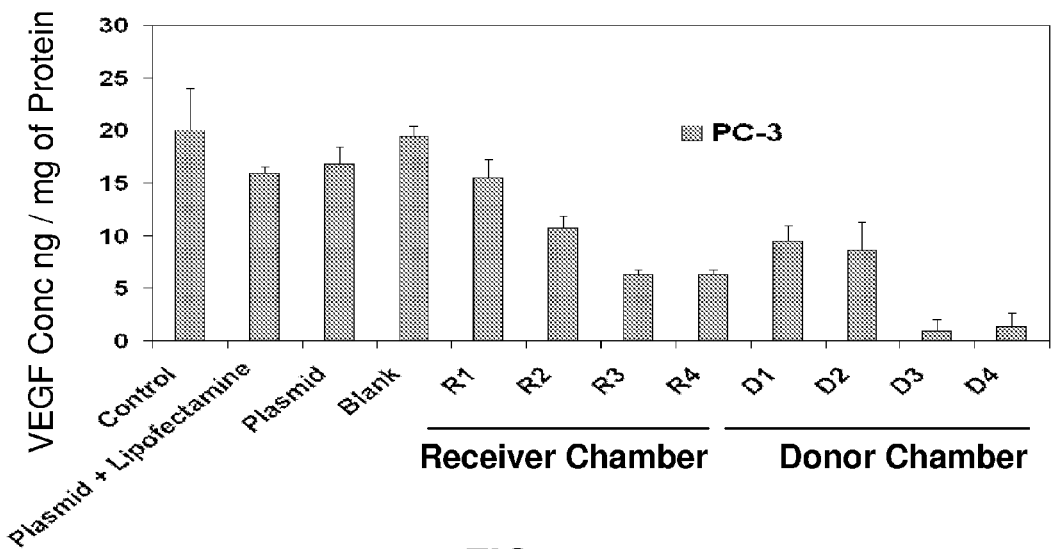

The media collected from the treated cells were used for VEGF ELISA to determine the VEGF secreted. The ELISA was performed using a previously described method including 12 hours treatment in serum free media, followed by 7 days culture in serum free media, with a medium changed every 3 days (FIG. 43), 12 hours in serum free media with receiver and donor chamber samples, 24 hours incubation, with a medium change 12 hours post treatment (FIGS. 44 and 45). LNCaP and PC-3 were used for these studies. Controls used for the study included: Control (no treatment), plasmid+lipofectamine, plasmid alone and blank nanoparticles (no plasmid; no conjugation). The VEGF was measured by ELISA as the concentration of VEGF (ng/ml) in the medium. As shown in FIGS. 43-45, the VEGF secretion was in the order: transferrin (Tf) moiety-targeted carrier particle (R4 and D4)≤deslorelin (des) moiety-targeted carrier particle (R3 and D3)<unconjugated carrier particle (R2 and D2)<plasmid alone (R1 and D1). Further, donor chamber samples exhibited greater reduction in the VEGF secretion compared with the receiver chamber samples.

Example 16

Receptor Binding Assays in Bovine Nasal Tissue

In various regions of the nose, $B_{max}$, $K_D$, and $IC_{50}$ values for LHRH-receptor and deslorelin were determined. Bovine tissues were obtained from a local slaughterhouse (J & J Meats, Elkhorn, Nebr.). The nasal tissues were isolated and prepared for experiments as described by Schmidt et al. (2000) J. Pharm. Sci. 89:396-407. The frontal part of the nasal conchae was dissected and the mucosal tissues were then separated from the cartilage using a pair of tweezers. Different regions of the bovine nasal tissue, including the medium turbinate anterior (MTA)—up to 2.5 inches from the frontal tip of the nares; the medium turbinate posterior (MTP)—beyond 2.5 inches past the tip of the nares; and the inferior turbinate posterior (ITP)—beyond 2.5 inches past the tip of the nares, below the MTP region and facing the floor of the nasal cavity, i.e., the inferior meatus, were isolated and used immediately for the experiments.

Preparation of Tissue for Receptor Binding Assay: The isolated tissues (~200 mg) were homogenized using the Tissue Tearor® in 2 ml of Tris-HCl buffer. The tissue homogenate was then centrifuged at 15000 g for 15 min at 4° C. to separate the crude membrane from the buffer. Further, the tissue pellet was resuspended in 2 ml of the Tris-HCl buffer and rehomogenized with a Dounce Tissue Grinder having a capacity of 15 ml (Sigma-Aldrich, St Louis, Mo.). The membrane preparation was stored in 2 ml aliquots at −70° C.

Receptor binding studies were conducted using an incubation buffer containing 40 mmol of Tris-HCl, 10 mmol of EDTA, and 0.5% BSA, adjusted to pH 7.4. Transport across excised bovine nasal tissue was conducted using assay buffer. The assay buffer (pH 7.4) contained 1.14 mM $CaCl_2$, 1.2 mM $MgSO_4$, 3 mM KCl, 0.4 mM $KH_2PO_4$, 25 mM $NaHCO_3$, 10 mM glucose, 122 mM NaCl and 10 mM HEPES (N-2-hydroxyethylpiperazine-N'-2-ethanesulfonic acid). The assay buffer was pre-equilibrated to 37° C. for 30 min. The assay buffer adjusted to pH 5 with 1 N HCl was used as acid wash buffer.

Kinetic Study: To determine the time taken to achieve maximum binding with a small amount of radioactivity, time-course of tissue association was determined with 100 cpm of $I^{125}$-deslorelin (Bachem California, Torrance, Calif.). At the end of various time points (0 to 4 hr), the incubation tubes were centrifuged at 10,000 g for 20 min at 4° C. to separate the bound fraction. Radioactivity was measured in the pellet using a Perkin-Elmer γ-counter. Controls without tissue, with and without unlabelled deslorelin were included for correction of nonspecific binding to the tubes, as were positive controls using bovine pituitary tissue homogenates. Kinetic studies at 4° C. indicated that binding of $^{125}$I-deslorelin reached a maximum at 1.5 hr and remained stable until 4 hr. All subsequent experiments were conducted up to 4 hr at 4° C.

Figure 46:
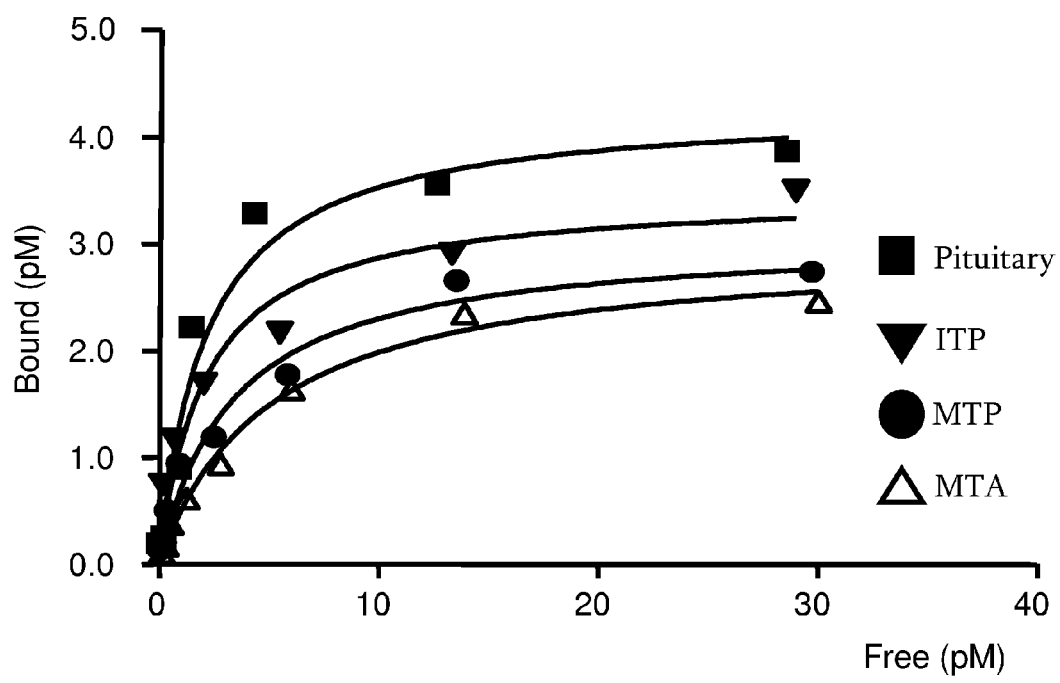
FIG. 46 is a saturation curve for $^{125}$I-deslorelin comparing the saturation in bovine pituitary versus three regions of bovine nasal tissue.
Figure 47:
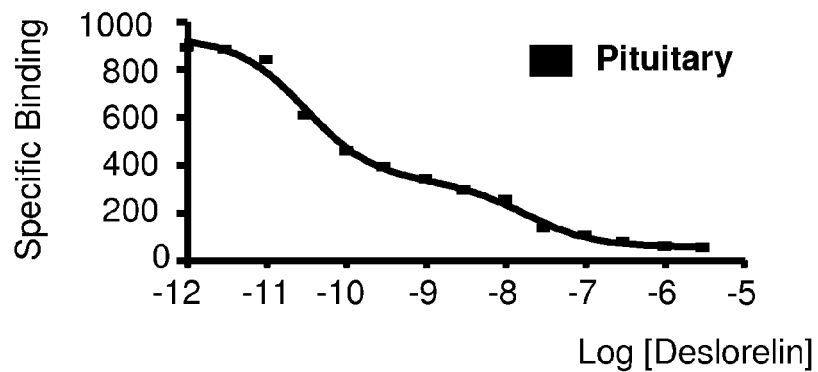
FIGS. 47-50 are competition binding curves of $^{125}$I-deslorelin in the presence of unlabeled deslorelin, to various regions of bovine tissue: pituitary (FIG. 47); medium turbinate posterior (MTP.
Figure 48:
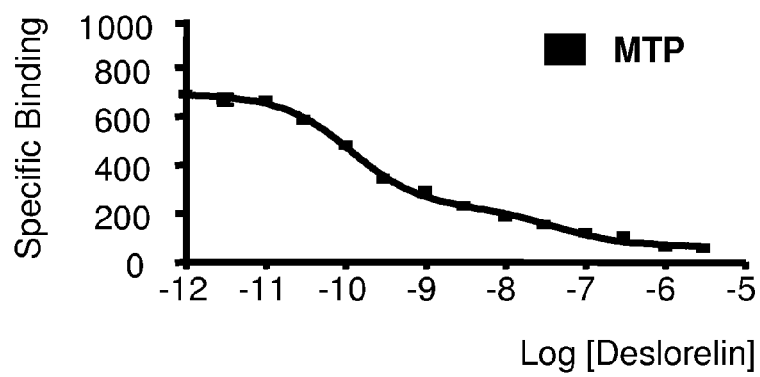
Figure 49:
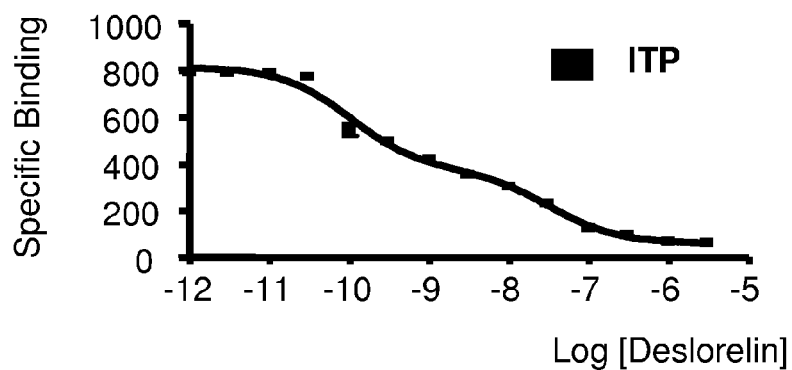
Figure 50:
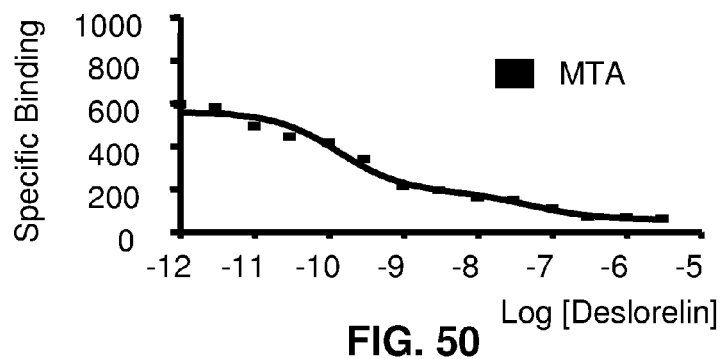

Saturation Study: To determine the amount of ligand that will saturate receptors in nasal tissue preparations, receptor binding assays were performed in polypropylene tubes as previously described by Bramley et al. (1999) Mol. Hum. Reprod. 5(12):1095-1106, Bramley et al. (1999) Mol. Hum. Reprod. 5(8):777-783, and Bylund et al. (2004) Methods Mol. Biol. 259:1-28. Bovine tissue homogenates (0.5 mg) in Tris buffer were incubated with 100-100,000 cpm $I^{125}$ labeled deslorelin in a final volume of 200 µl in the presence or absence of unlabelled deslorelin (80 ng) for 4 hr at 4° C. At the end of 4 hr, the incubation tubes were centrifuged at 10000 g for 20 min at 4° C. to separate the bound fraction. Radioactivity was measured in the pellet using a Perkin-Elmer γ-counter. Controls were the same as those used in the kinetic study. $B_{max}$ and $K_D$ values were obtained from each of the experiments. The experiment was repeated three times. Saturation studies indicated that LHRH-R exhibits differential expression (Bmax) and deslorelin has differential affinity for the receptor (Kd) in different regions of the bovine nasal tissue (FIG. 46). Statistical analysis indicated significant difference between the $B_{max}$ values of the tissues in the following order: MTA<MTP<ITP<Pituitary. The affinity of deslorelin for the receptor also exhibited a similar trend (Table 9).

TABLE 9

Saturation Studies In Pituitary and Bovine Nasal Tissue

| Tissue | $B_{max}$ | $K_d$ |
|---|---|---|
| Pituitary | 425.03 ± 3.92 | 2.374 ± 0.186 |
| ITP | 353.10 ± 5.311* | 2.236 ± 0.102 |
| MTP | 311.30 ± 6.61*† | 3.426 ± 0.246* |
| MTA | 298.53 ± 3.29*†‡ | 5.118 ± 0.5167*† |

Key:
Data are expressed as mean ± standard deviation for n = 3 experiments.
The asterisk (*) indicates a P < 0.05 compared with pituitary for $B_{max}$ and compared with ITP region for $K_d$,
the cross (†) indicates a P < 0.05 compared with ITP region for $B_{max}$ and compared with MTP region for $K_d$, and
the double cross (‡) indicates a P < 0.05 compared with MTP region for $B_{max}$.
MTA = medium turbinate anterior region,
MTP = medium turbinate posterior region,
ITP = inferior turbinate posterior region of bovine nasal tissue.

Competition Studies: To determine the amount of unlabelled deslorelin required to displace the radioactivity, competition studies were conducted. Briefly, membranes were incubated with 100,000 cpm of $I^{125}$ deslorelin in the presence or absence of unlabelled deslorelin (0.01-3,000 ng) in a total volume of 200 µl for 4 hr at 4° C. Assays were performed in triplicates. At the end of 4 hr, the incubation tubes were centrifuged at 10,000 g for 20 min at 4° C. to separate the bound fraction. Radioactivity was measured in the pellet using a Perkin-Elmer γ-counter. The same controls as in the kinetic and saturation studies were used. The experiment was repeated three times. Competition studies indicated two deslorelin binding sites in each of the nasal tissue regions (FIG. 47-50). The high affinity binding sites accounted for approximately 60-70% of all the binding sites available. Statistical analysis indicated significant differences in IC50 values, for both low and high affinity sites, in the order: MTA<MTP<ITP (Table 10).

TABLE 10

Competition Studies In Pituitary and Bovine Nasal Tissue

| Tissue | High affinity - $IC_{50}$ I (nM) | Low affinity - $IC_{50}$ II (nM) |
|---|---|---|
| Pituitary | 0.031 ± 0.001 | 17.93 ± 0.449 |
| ITP | 0.102 ± 0.001* | 32.87 ± 1.255* |
| MTP | 0.112 ± 0.004*† | 42.10 ± 1.835*† |
| MTA | 0.136 ± 0.002*†‡ | 53.25 ± 4.005*†‡ |

Key:
Data are expressed as mean ± standard deviation for n = 3 experiments.
The asterisk (*) indicates a P < 0.05 compared with pituitary,
the cross (†) indicates a P < 0.05 compared with ITP region, and
the double cross (‡) indicates a P < 0.05 compared with MTP region.

Example 17

Assay for Receptor mRNA Expression in Nasal Tissue

The expression of LHRH receptor (LHRH-R), transferrin receptor 1 (TfR1) and transferrin receptor 2 (TfR2) mRNA levels were quantified relative to the expression of these receptors in pituitary by real time polymerase chain reaction (real-time PCR). RNA isolation from bovine conjunctiva and corneal epithelium was carried out using RNA STAT-60 RNA isolation kit (TEL-TEST, Friendswood, Tex.). Briefly, freshly excised tissues were homogenized in 1 ml RNA STAT-60 (TEL-TEST, Friendswood, Tex.) solution followed by extraction with 200 µl of chloroform. The tissue debris, DNA as well as proteins were separated into the organic phase by centrifugation at 12,000 g for 15 min at 4° C. The aqueous phase contained the RNA. Further extraction was carried out with isopropanol (1:1 v/v ratio with the aqueous phase). The RNA was precipitated and separated by centrifugation at 12,000 g for 15 min at 4° C. The RNA pellet obtained was washed with 70% ethanol. Purified RNA was separated by centrifugation at 7500 g for 5 min at 4° C. The pellet was air dried and redissolved in 100 µl of nuclease free water by incubation at 55° C. for 15 min. Care was taken not to over dry the pellet in order to facilitate redissolution. The RNA samples were analyzed with UV spectrophotometry. Samples with $A_{260}$ to $A_{280}$ ratio equal to or more than 1.8 were considered to be free of DNA and protein contamination.

The RNA (5 µg/ml) isolated from different regions of the bovine nasal tissues was converted into cDNA by reverse transcription. Real-time PCR was carried out using the ABI PRISM 7500 Sequence Detection System (Applied Biosystems). The reactions were performed with 2×SYBR Green PCR master mix (Applied Biosystems), in the presence of 30 ng cDNA and 300 nM of specific primer sets, as shown in Table 1 (in Example 1). Samples were analyzed in triplicates. Amounts of input RNAs in each sample were corrected for by dividing threshold cycle (Ct) of each specific gene by the Ct for 18s rRNA. Fold values were calculated as $2^{-\Delta Ct}$, where $\Delta Ct = Ct$ for the specific gene—Ct for 18s rRNA in the same RNA. The sample with the lowest expression was set to 1.0 fold and other data were adjusted to that baseline, as described in Roth et al. (2001) J. Endocrinology 169(2):361-71 and Schirman-Hildesheim et al. (2005) Endocrinology 146(8):3401-8.

Figure 51:
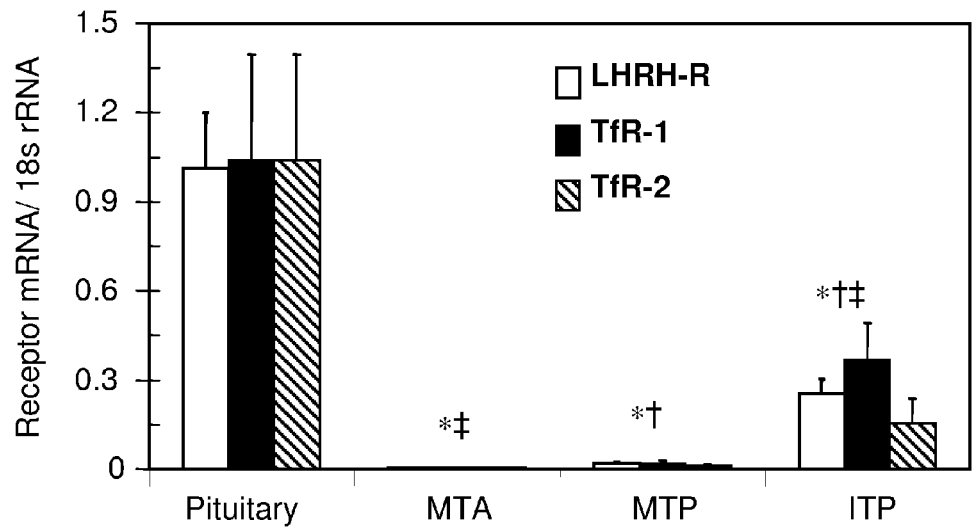
FIG. 51 illustrates differential expression of LHRH and transferrin receptors in various regions of bovine nasal tissue as compared to pituitary.

Real time PCR studies indicated that the mRNAs of LHRH-R I, TfR1, and TfR2 exhibit regional differences in the order: MTA<MTP<ITP (FIG. 51), with the differences being significant between MTA and either of the other two regions. Comparison of mean values between the different treatments was carried out using two way analysis of variance (ANOVA) followed by Tukey's post-hoc analysis with the SPSS (version 8) software. Differences were considered statistically significant at P≤0.05. Data is presented as means±standard deviation for n=3 samples. The asterisk indicates a p<0.05 compared with expression in the bovine pituitary, the cross indicates a p<0.05 compared with expression in the MTA region, and the double cross indicates a p<0.05 compared with expression in the MTP region.

Example 18

Western Blot Assay for Receptors in Nasal Tissue

The expression of LHRH receptor (LHRH-R), transferrin receptor 1 (TfR1) and transferrin receptor 2 (TfR2) in nasal tissue was assayed by Western blot. Homogenates of freshly excised bovine tissues were prepared in the presence of protease inhibitors mixture including 1% PMSF (Sigma-Aldrich, St Louis, Mo.), 5% protease inhibitor cocktail (Sigma-Aldrich, St Louis, Mo.) and 1% sodium dodecyl sulfate (SDS) Total protein content of each of tissue homogenate was estimated using Pierce's BCA kit (Pierce Biotechnology, Rockford, Ill.). Tissue samples (20 µg of protein) were then loaded onto polyacrylamide gels with PC-3 (prostate carcinoma cell line) cell lysates as positive controls. Molecular weight markers ranging from 14.3 to 220 kDa (Amersham Life Science, Arlington Heights, Ill.) were used to identify LHRH receptor, transferrin receptors, and β-actin protein bands.

Figure 52:
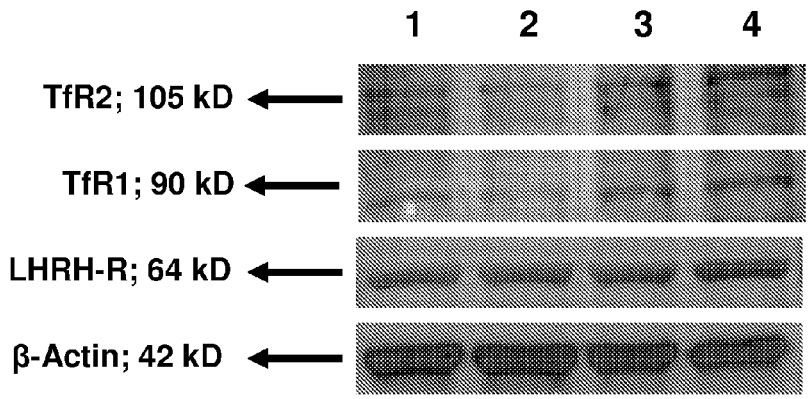
FIG. 52 is a Western blot assay to detect the presence of receptors for LHRH and transferrin in bovine tissue: MTA (lane 1), MTP (lane 2) ITP (lane 3), and pituitary (lane 4).

The proteins were separated using preformed 10% polyacrylamide gels (Bio-Rad, Hercules, Calif.) and SDS-PAGE. The gels were run at 60 V for 10 min and then continued at 120 V for another 1.5 hours. The proteins were then transferred to polyvinylidene fluoride (PVDF) membranes (Millipore, Bedford, Mass.) at 4° C. using a current of 480 mA. Immunoblotting was performed with specific antibodies for LHRH-R (1:100 dilution) (LabVision, Freemont, Calif.), TfR1 (1:1000 dilution) (Biodesign International, Saco, Me.), and TfR2 (1:1000 dilution) (Abcam Inc, Cambridge, Mass.) or the monoclonal anti α-actin antibody (1:1000 dilution) (Sigma-Aldrich, St Louis, Mo.) after treatment with blocking buffer containing 0.3% Tween, 1% BSA, and 5% non-fat dry milk (NFDM). Incubation with antibody was done overnight at 4° C. Following washes with Tris buffer at pH 7.4, secondary antibody, horseradish peroxidase conjugated mouse or rabbit immunoglobulin (Ig) (Jackson Immunoresearch, West Grove, Pa.), was added (1:1500) as needed and incubated at 4° C. for 1 hour. Protein bands were visualized using a ECL-Plus chemiluminescence kit (Amersham Biosciences, Piscataway, N.J.). Protein expression analysis using the Western blot indicated the expression of LHRH-R in all three regions of the nose. Further, TfR1 was expressed in all three regions. However, TfR2 was not readily discernible in the western blots (FIG. 52). Lanes 1, 2 and 3 represent bovine nasal MTA, MTP, and ITP regions, respectively, and Lane 4 represents pituitary.

Example 19

Nanoparticle Transport Studies in Bovine Nasal Tissue

Transport studies were conducted in bovine nasal tissue. Bovine nasal tissue was obtained from freshly slaughtered cattle, and different regions (MTA, MTP, ITP) were prepared as described in Example 13. Nanoparticles coupled to deslorelin or transferring via aldehyde sulfate moieties were prepared as described in Example 3. The nanoparticle size was measured using a Zeta Plus Analyzer (Brookhaven Instruments Limited, UK). Particle size was analyzed before and after ligand conjugation in deionized filtered water.

Nanoparticle Transport Studies: Modified Ussing's chambers (Navicyte, Reno, Nev.) were used to mount the nasal tissue for permeability studies. The tissues were exposed to 5 ml of assay buffer with either peptide conjugated or plain nanoparticles on the donor side (mucosal or serosal surface). Assay buffer (5 ml) without particles was exposed to the receiver side (serosal or mucosal surface). The buffers used were pre-equilibrated to 37° C. or 4° C. The donor nanoparticle concentration was 20 or 100 μg/ml. The chambers were maintained at a constant temperature (37° C. or 4° C.) with an external circulating water bath. Samples were collected from the receiver chamber at various intervals up to 4 hr and replaced with assay buffer. Donor samples were collected at the beginning (replenished with particle stock suspension) and at the end of the experiment. The samples were collected in polypropylene tubes, capped, and stored at 4° C. until analysis. The aperture/tissue area exposed to the bathing fluids in this set up was 1.78 $cm^2$.

Nanoparticle Uptake: At the end of 4 hr in the above transport studies, the tissues exposed (1.78 $cm^2$) to the nanoparticle suspension were cut and washed thrice using 1 ml of assay buffer at pH 5. After the washes, the tissues were weighed and placed in 1 ml of 2% Triton-X 100™ and homogenized until a tissue suspension was formed using the Tissue Tearor™. The tissue debris was separated by centrifugation at 3000 rpm (Marathon Micro A, Fisher Scientific, Pittsburgh, Pa.) for 10 min. The supernatant was collected to analyze the amount of nanoparticles taken up by the tissue. Standard curves were prepared by homogenizing serial dilution of the stock solution with approximately 100-150 mg of nasal tissue. The homogenates were then centrifuged and the supernatant was analyzed.

Transport and uptake of nanoparticles across excised bovine nasal tissue exhibited regional differences and directionality. The cumulative 4 hr percent transport and percent uptake of the plain nanoparticles, deslorelin-targeted nanoparticles, and transferrin-targeted nanoparticles was in the order: MTA<MTP<ITP in both the m:s and s:m directions. Further, the cumulative transport and percent uptake of nanoparticles was in the order: NP<deslorelin-NP<transferrin-NP in both m:s and s:m directions (FIGS. 53-58).

The percent transport of deslorelin-nanoparticles as compared with the plain nanoparticles, in the m:s direction was approximately 2.5-, 1.5-, and 1.4-times higher, respectively, in the MTA, MTP and ITP regions. Similarly, the uptake of deslorelin-nanoparticles was 2.9-, 2-, and 1.4-times higher compared to plain nanoparticles, in the three respective regions. The percent transport of transferrin-nanoparticles as compared with plain nanoparticles, in the m:s direction, was approximately 3.3-, 2.1-, and 1.8-times higher in the MTA, MTP and ITP regions, respectively. Similarly, transferrin-nanoparticle uptake was 3.6-, 2.9-, and 2.5-times higher when compared to plain nanoparticles in the three respective regions. The percent transport as well as uptake of transferrin nanoparticles was 1.3-1.4-times higher compared with deslorelin-nanoparticles in the MTA, MTP and ITP regions. A mass balance analysis in various experiments for the particles used in this study accounted for nearly 100% of initial amount added to the donor chamber (Table 11). The mass balance was done using nanoparticle suspensions from the receiver chamber, tissue washes and remainder of the particles in the donor chamber, and tissue extracts.

TABLE 11

Mass Balance of Nanoparticles in Tissues After Transport Experiments

| Particles Used | Region | Tissue Uptake | Transport | Washes | Remaining in Donor | Total |
|---|---|---|---|---|---|---|
| NP | MTA | 0.58 ± 0.08 | 0.34 ± 0.02 | 0.20 ± 0.05 | 97.70 ± 0.32 | 99.25 ± 0.45 |
|  | MTP | 1.07 ± 0.09 | 0.71 ± 0.04 | 0.19 ± 0.04 | 96.54 ± 0.55 | 99.14 ± 0.19 |
|  | ITP | 1.64 ± 0.16 | 1.05 ± 0.03 | 0.17 ± 0.04 | 95.49 ± 1.40 | 99.87 ± 0.12 |
| Des-NP | MTA | 1.68 ± 0.12 | 0.84 ± 0.04 | 0.15 ± 0.02 | 96.30 ± 0.42 | 98.08 ± 0.85 |
|  | MTP | 2.20 ± 0.08 | 1.06 ± 0.01 | 0.28 ± 0.04 | 95.06 ± 0.28 | 98.24 ± 1.95 |
|  | ITP | 2.75 ± 0.09 | 1.45 ± 0.07 | 0.47 ± 0.02 | 94.31 ± 0.24 | 102.74 ± 1.07 |

TABLE 11-continued

Mass Balance of Nanoparticles in Tissues After Transport Experiments

| Particles Used | Region | Tissue Uptake | Transport | Washes | Remaining in Donor | Total |
|---|---|---|---|---|---|---|
| Transf-NP | MTA | 2.13 ± 0.13 | 1.13 ± 0.07 | 0.50 ± 0.13 | 93.06 ± 0.99 | 98.77 ± 0.95 |
|  | MTP | 2.99 ± 0.14 | 1.52 ± 0.11 | 0.60 ± 0.11 | 92.14 ± 2.20 | 98.99 ± 0.52 |
|  | ITP | 3.98 ± 0.10 | 1.97 ± 0.05 | 0.75 ± 0.10 | 94.51 ± 1.10 | 98.62 ± 1.13 |

Key:
NP = unconjugated nanoparticles, particle mean diameter = 20 nm,
Des-NP = deslorelin-targeted nanoparticles, particle mean diameter = 129 nm,
Transf-NP = transferrin-targeted nanoparticles, particle mean diameter = 90 nm. All were conjugated using aldehyde sulfate functionalities. Mass balance for particles in donor chamber, receiver chamber, tissue, and washes is provided.
Data are expressed as mean ± standard deviation for n = 4.

Figure 53:
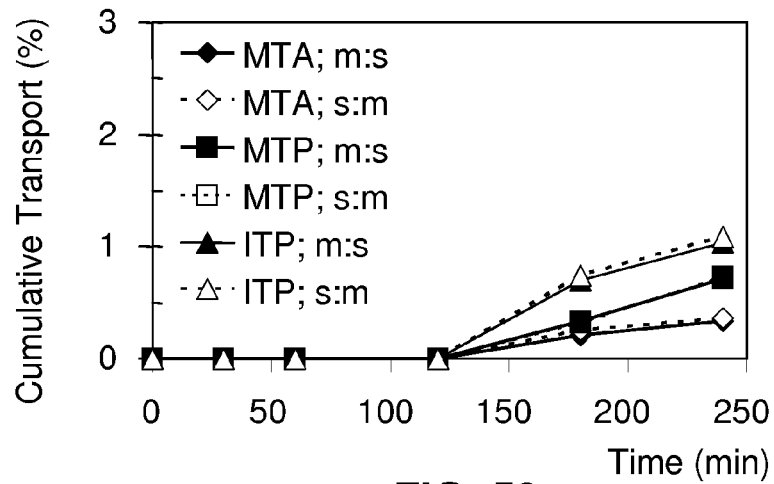
FIGS. 53-55 are graphs depicting the in vitro transport of nanoparticles across various regions of bovine nasal epithelium over time for unconjugated nanoparticles (FIG. 53), deslorelin-conjugated nanoparticles (FIG. 54), and transferrin-conjugated nanoparticles (FIG. 55).
Figure 54:
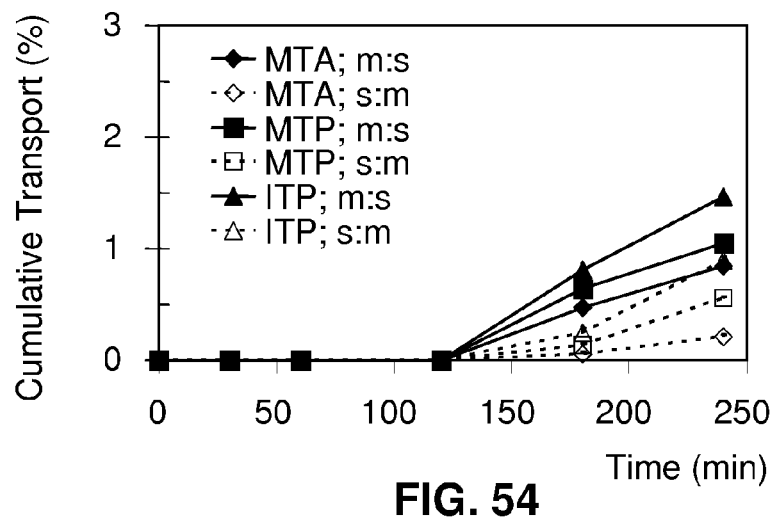
Figure 55:
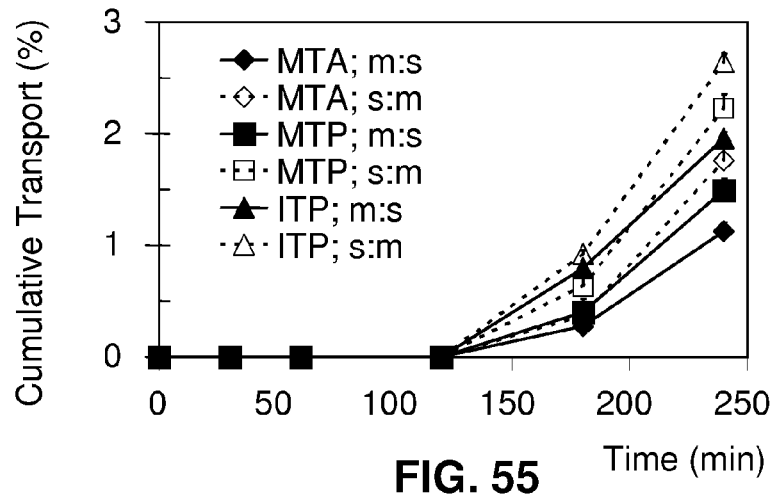
Figure 56:
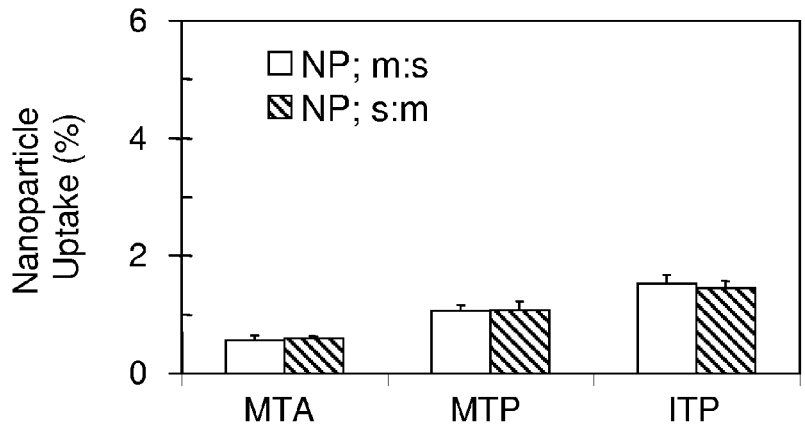
FIGS. 56-58 are charts illustrating the percent nanoparticle uptake in bovine nasal tissue in the mucosal-to-serosal (m-s) and serosal-to-mucosal (s-m) directions, for unconjugated nanoparticles (FIG. 56), deslorelin-conjugated nanoparticles (FIG. 57), and transferrin-conjugated nanoparticles (FIG. 58).
Figure 57:
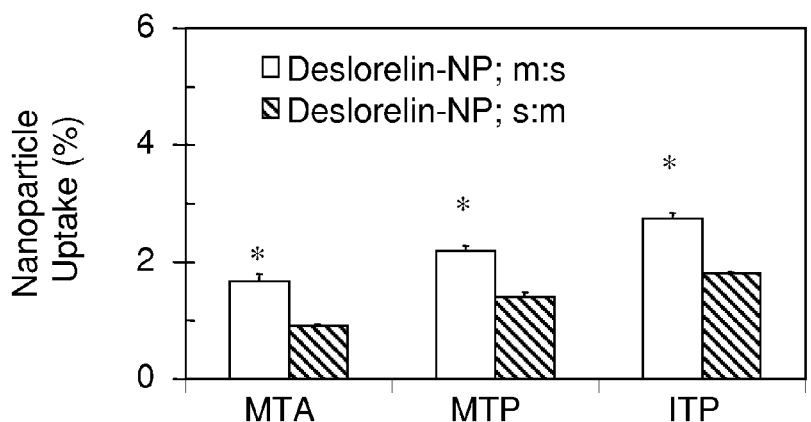
Figure 58:
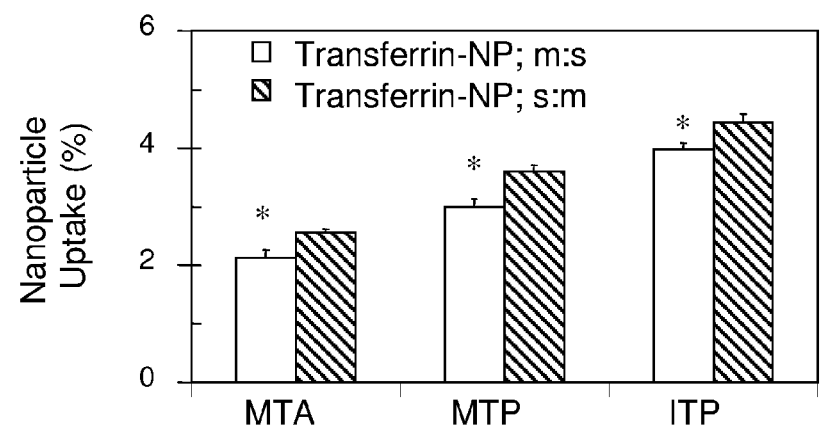

In the s:m direction, the transport and uptake of nanoparticles exhibited trends similar to the transport and uptake in the m:s direction and was in the order: plain nanoparticles<deslorelin-targeted nanoparticles<transferrin-targeted nanoparticles. There was no significant difference in the transport and uptake of plain nanoparticles in either direction (FIGS. 53 and 56). Transport and uptake of deslorelin-nanoparticles was higher in the mucosal to serosal (m:s) direction as compared to transport in the serosal to mucosal (s:m) direction. Deslorelin-nanoparticle transport in the s:m direction when compared to m:s direction was 60, 45, and 30% lower in the MTA, MTP, and ITP regions, respectively (FIG. 54). The corresponding decrease in uptake was 46, 49, and 34%, respectively (FIG. 57). Transport and uptake of transferrin-targeted nanoparticles was higher in the s:m direction as compared with transport in the m:s direction. Transferrin-nanoparticle transport in the s:m direction, when compared to the m:s direction is 16, 17, and 10% greater in the MTA, MTP, and ITP regions, respectively (FIG. 55). The uptake for transferrin-NP in m:s direction compared to s:m direction was 40, 29, and 25%, lower in the MTA, MTP, and ITP regions, respectively (FIG. 58).

Figure 59:
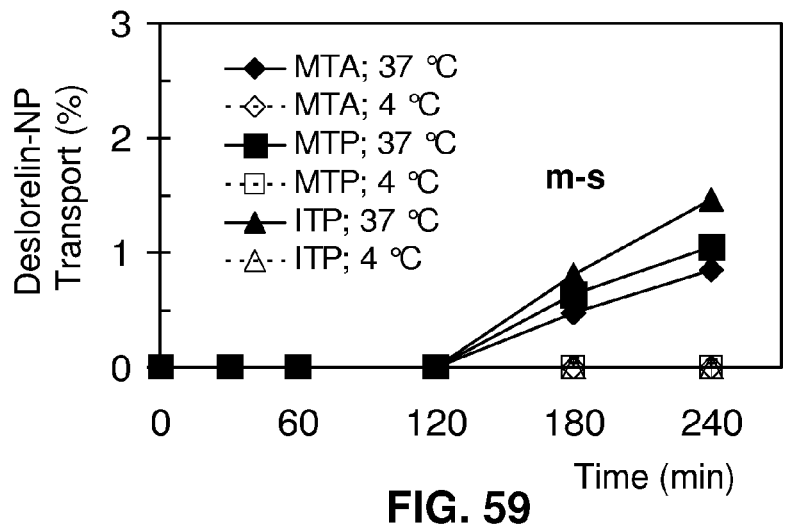
FIGS. 59, 60, 62 and 63 are graphs depicting how the in vitro transport of nanoparticles across various regions of bovine nasal epithelium varies over time depending on the temperature. Deslorelin-conjugated and transferrin-conjugated particle transport is shown for the m-s (FIG. 59, 62) and s-m (FIG. 60, 63) directions.
Figure 60:
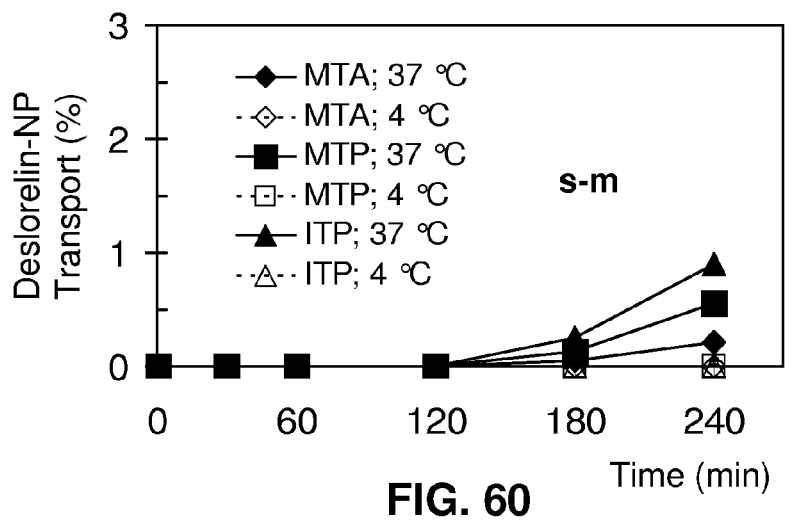
Figure 61:
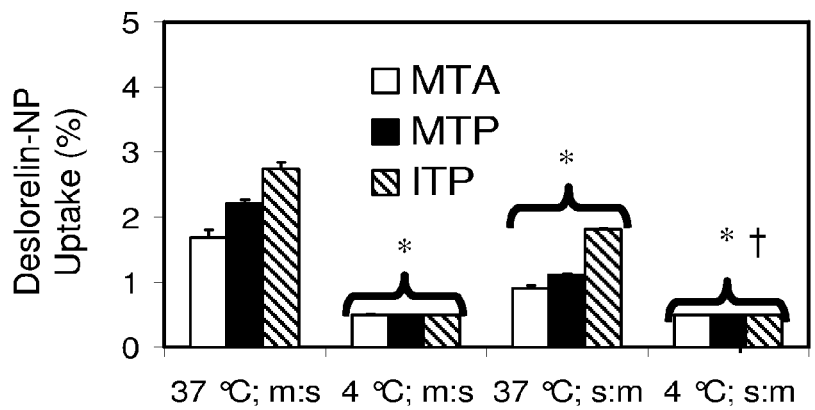
FIGS. 61 and 64 are charts illustrating the percent nanoparticle uptake in bovine nasal tissue for deslorelin-conjugated (FIG. 61) and transferrin-conjugated (FIG. 64) nanoparticles.
Figure 62:
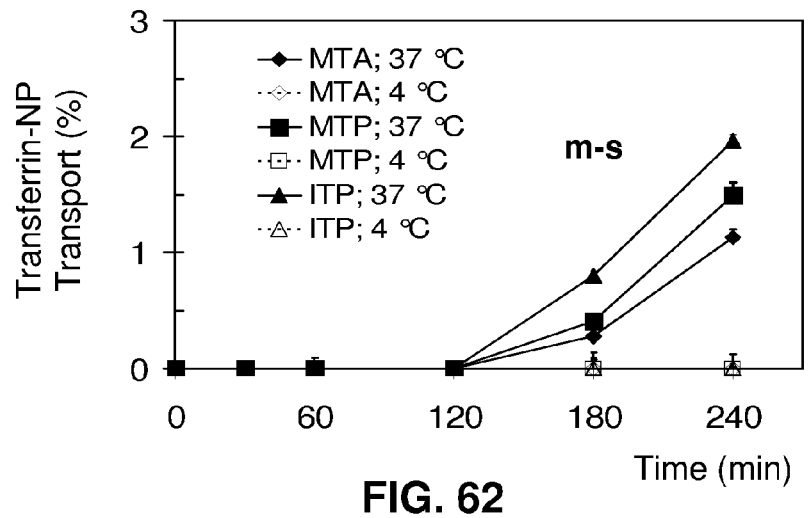
Figure 63:
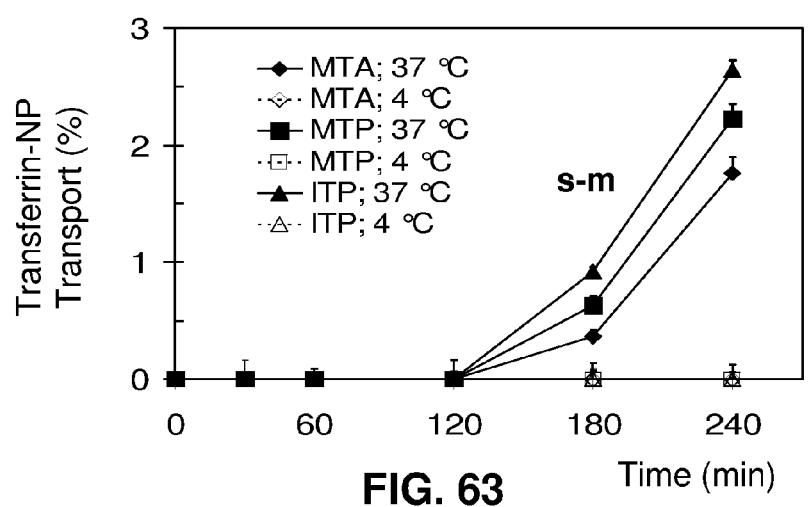
Figure 64:
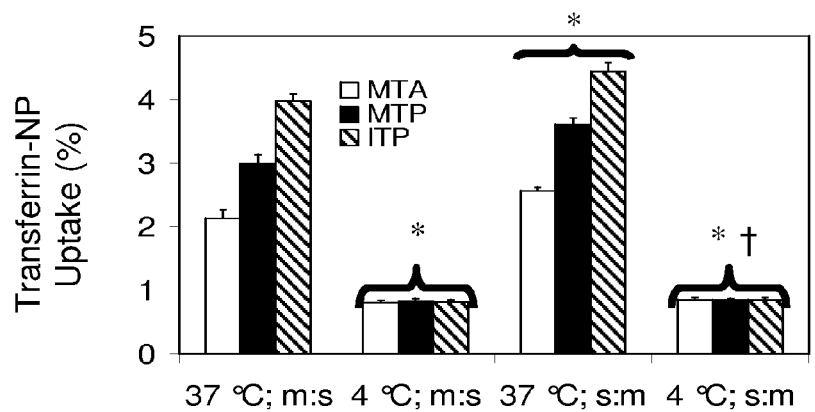

At low temperature (4° C.) when compared to 37° C., the transport of deslorelin (FIGS. 59 and 60) and transferrin (FIGS. 62 and 63) targeted nanoparticles was reduced dramatically and the directionality was abolished. Uptake of nanoparticles was also lower at 4° C. and did not exhibit directionality. Deslorelin-nanoparticle uptake, in the m:s direction at 4° C., was 70, 78, and 82% lower in the MTA, MTP, and ITP regions, respectively. The analogous decrease in uptake in the s:m direction was 43, 57, and 72%, respectively (FIG. 61). Transferrin-nanoparticle uptake, in the m:s direction at 4° C., decreased by 58, 70, 77% in the MTA, MTP, and ITP regions, respectively. The analogous decrease in uptake in the s:m direction was 65, 75, 80%, respectively (FIG. 64).

Nanoparticle Transport and Uptake: Competition with Free Ligand: Similar to the transport and uptake studies mentioned above, the competition study was carried out using the modified Ussing chambers. The tissues were exposed to 20 µg/ml of nanoparticles conjugated with deslorelin or transferrin in the presence of 10 times (200 µg/ml) of plain deslorelin or transferrin in the donor chamber. Receiver samples were obtained at various intervals up to 4 hr and replaced with pre-warmed assay buffer. At the end of 4 hr the tissue region exposed to the nanoparticle preparation was cut and washed in assay buffer at pH 5. The tissues were then homogenized and centrifuged. The supernatants were analyzed to determine nanoparticle uptake.

Figure 65:
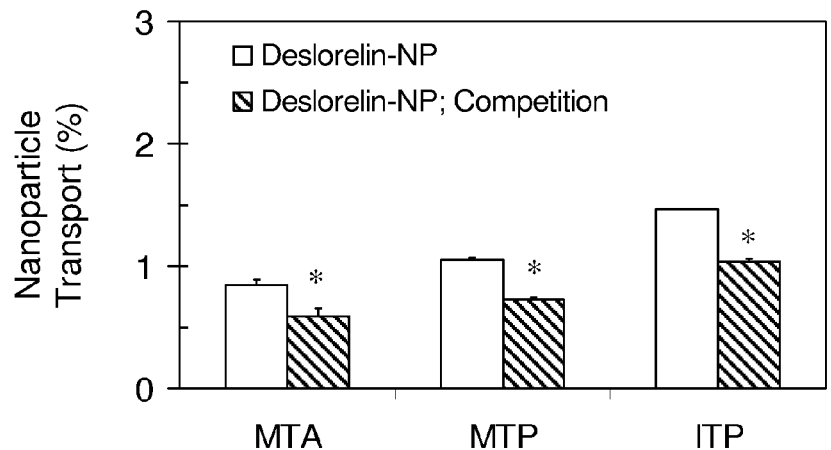
FIGS. 65-68 are charts depicting the in vitro transport and uptake of nanoparticles in various regions of bovine nasal epithelium in the presence of excess amounts of free ligand. Transport and uptake are shown for both deslorelin-conjugated nanoparticles (FIGS. 65, 66) and transferrin-conjugated nanoparticles (FIGS. 67, 68), respectively.
Figure 66:
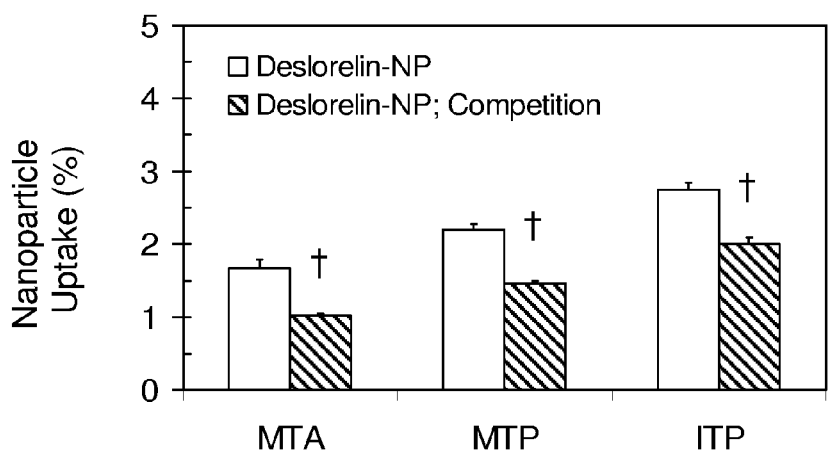
Figure 67:
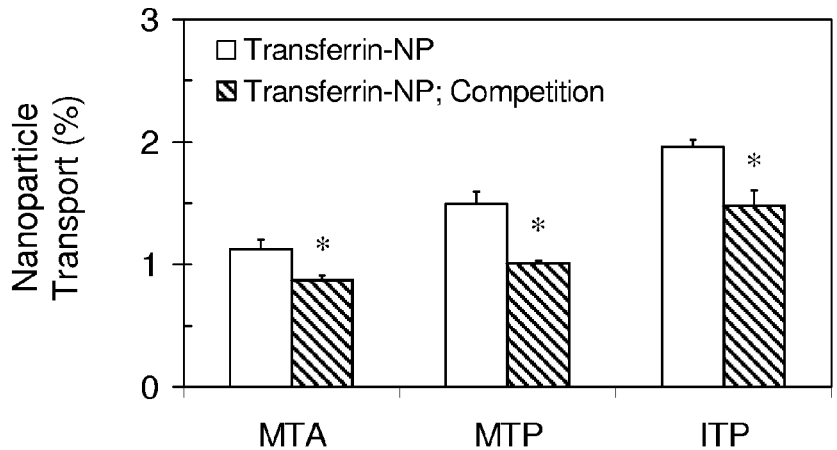
Figure 68:
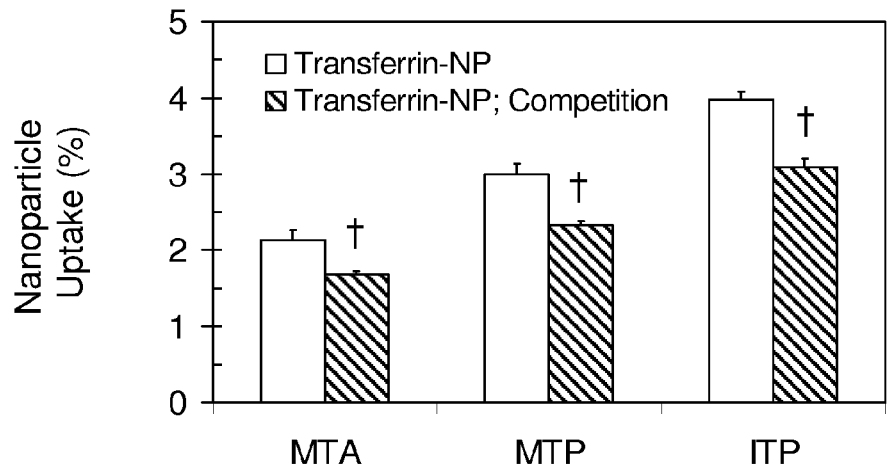

Free ligands (deslorelin and transferrin) competed with targeted nanoparticles for m:s uptake and transport. Co-treatments with excessive free peptides significantly reduced the transport of deslorelin or transferrin conjugated nanoparticles. Deslorelin co-treatment decreased deslorelin-nanoparticle transport by 30, 31, and 28% in the MTA, MTP, and ITP regions, respectively (FIG. 65). The corresponding decrease in uptake was 39, 33, and 27%, respectively (FIG. 66). Transferrin co-treatment decreased transferrin-nanoparticle transport by 22, 33, and 25%, respectively (FIG. 67). The corresponding decrease in transferrin-nanoparticle uptake was 43, 45, and 44%, respectively (FIG. 68). However, even in the presence of free peptide/protein, the transport still exhibited regional differences in the order: MTA<MTP<ITP.

Nanoparticle Uptake—Confocal Laser Scanning Microscopy and Flow Cytometry: At the end of 4 hr in the above transport studies, the tissues exposed to the drug were cut and washed thrice in 1 ml of acid buffer. The tissues were then fixed in 4% paraformaldehyde for 15 min and washed thrice in 2 ml of PBS buffer. The tissues were then permeabilized for 30 min at room temperature with 0.1% Triton-X solution in PBS. The tissues were again washed thrice with PBS and were finally stained with 1 µg/ml propidium iodide for 5 min. Images of the particles taken up by the tissues were obtained at 40× magnification with a confocal laser microscope (Zeiss Confocal LSM410, Carl Zeiss MicroImaging Inc., Thornwood, N.Y.). Following confocal microscopy of the tissues, the epithelial cells on the mucosal surface were isolated. Images of the particle uptake in epithelial cells were obtained at 100× magnification under oil immersion lens. Blank controls with plain assay buffer in the donor chamber served as negative controls and were treated the same way as the experimental samples.

Figure 69:
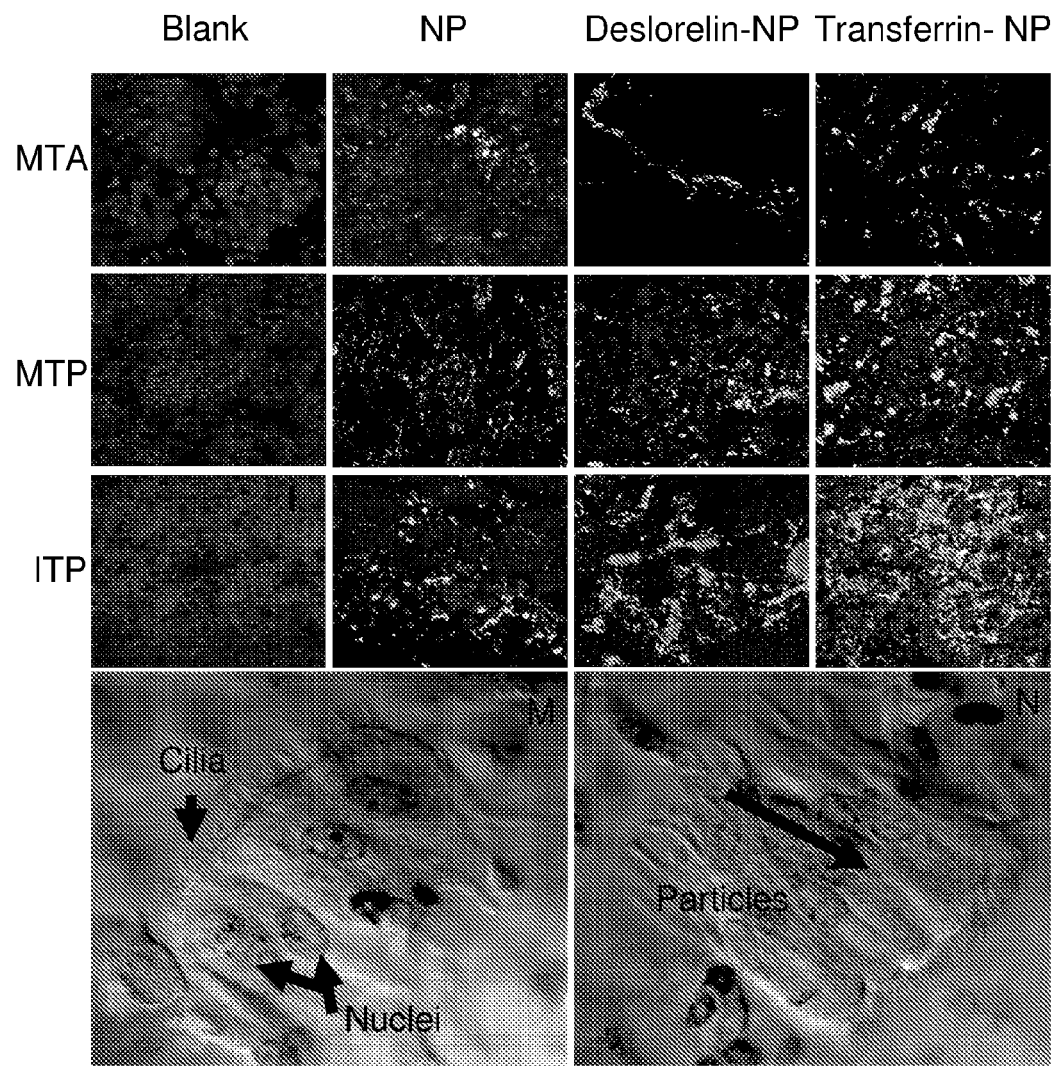
FIG. 69 is a panel of confocal images illustrating the uptake of nanoparticles in multiple layers of bovine nasal and epithelial tissue after transport studies. The images in column 1 (panels A, E, I) are negative controls, in column 2 (panels B, F, J) are unconjugated nanoparticles, in column 3 (panels C, G, K) are deslorelin-conjugated nanoparticles, and in column 4 (panels D, H, L) are transferrin-conjugated nanoparticles. Panels M and N illustrate the unconjugated and transferrin-conjugated nanoparticle uptake, respectively, in ITP cells.

Particle uptake in tissue and isolated epithelial cells was visualized using a confocal laser microscope at 40× and 100× magnifications, respectively, under oil immersion lens with an argon-krypton laser. The epithelial cells observed were pseudostratified columnar cells with non-ciliated cells observed in the MTA region and ciliated cells observed in the MTP and ITP regions. The particles were seen to be present in the cytoplasm of epithelial cells around the nucleus. No green fluorescence was observed in the negative controls. Similar to the uptake measured using spectrofluorometer, the uptake visualized using confocal microscopy showed regional differences in the order: MTA<MTP<ITP and the uptake of plain nanoparticles<deslorelin-nanoparticles<transferrin-nanoparticles (FIG. 69).

Figure 70:
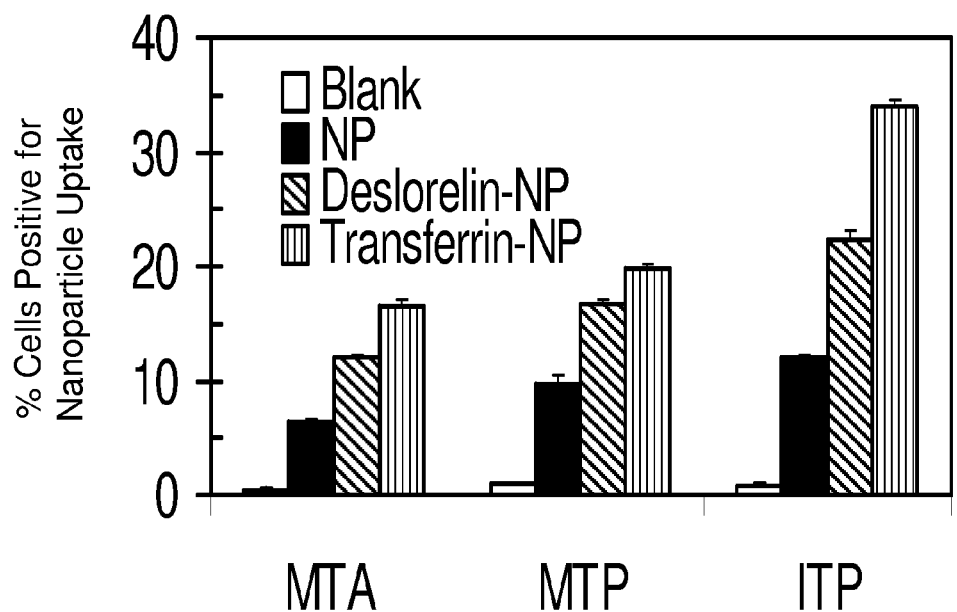
FIG. 70 is a chart depicting the results of flow cytometry quantification showing the percent of cells uptaking various nanoparticles in different bovine nasal tissue.

Flow cytometry was performed on single cell suspensions isolated from the tissues after 4 hr of transport of nanoparticles. Briefly, the tissues exposed to nanoparticles were isolated and washed thrice in 1 ml of acid buffer followed by fixing in 4% paraformaldehyde for 15 min at room temperature. The fixed tissues were placed in a test tube, washed thrice in PBS at pH 7.4, and exposed to trypsin-EDTA for 5 min at 37° C. to loosen the epithelial cells. At the end of 5 min the tubes were vigorously vortexed and the trypsin-EDTA was collected. The tissues were also scraped at the mucosal surface and the cells were collected and treated again with trypsin-EDTA. The two trypsin-EDTA fractions were combined and neutralized with 10% FBS containing RPMI-1640 media to avoid cell lysis by trypsin-EDTA. The tissue scraping, trypsin-EDTA exposure, and FBS neutralization was repeated two more times. The suspension was then centrifuged at 600 g for 5 min. The cell pellet obtained was resuspended in 1 ml of distilled water and analyzed using flow cytometry. Particle uptake in epithelial cells of bovine nasal tissues from all three regions was also quantified using flow cytometry. No particle uptake was observed in the blank control tissues. Epithelial cell uptake in the bovine nasal tissues was in the order: MTA<MTP<ITP. The uptake of the various nanoparticles was in the order: NP<Deslorelin-NP<Transferrin-NP (FIG. 70).

Nanoparticle Quantification: The samples obtained from the transport studies, washes and supernatants of tissue homogenates were analyzed for nanoparticle content using a spectrofluorometer (Cary Eclipse, Varian Inc.). The excitation wavelength of 505 nm and an emission wavelength of 515 nm were used. Bandwidths of 3 or 5 nm were used for the sample analysis after dilution as required. The procedure used for extraction of the nanoparticles was performed as mentioned in the methods section under nanoparticle uptake. A similar approach was used for the preparation of standards in tissues. Briefly, similar amounts of tissues (weighed to match weight of tissues obtained from the transport experiment) were spiked with serially diluted stock nanoparticle suspensions (0.3 μg/ml-100 μg/ml) prepared in 2% Triton-X 100™. The tissues were homogenized, centrifuged and the supernatant obtained was used for standards. Standard curves were also prepared in assay buffer and acid wash buffer.

Example 20

Preparation of Targeted Compositions Using PLA Carrier Particles

Polymeric nano- and microparticles are formulated by a solvent-evaporation method. Briefly, a therapeutic agent (or agents) and the polymer are dissolved in 1 ml dichloromethane, and this solution is added to 10 ml of an aqueous polyvinyl alcohol (2% wt/vol) solution. The resultant mixture is sonicated for 1.5 minutes at 20 W or 5 minutes at 50 W with a probe sonicator (Misonix, Farmingdale, N.Y.) to obtain an oil-and-water (O/W) emulsion for microparticle and nanoparticle formulations, respectively. The O/W emulsion is immediately added drop-wise to 125 ml of an aqueous polyvinyl alcohol (2% wt/vol) solution. The contents are stirred overnight at room temperature to evaporate the methylene chloride, allowing the formation of a turbid particulate suspension. The nano- and microparticles are separated by ultracentrifugation (35,000 g for 1 hour) and centrifugation (1000 g for 30 minutes), respectively. The pellets are washed two times, resuspended in deionized water, and freeze dried to obtain lyophilized particles. Carboxylate surface functionalities are added to the particles by conventional means.

Targeting moieties for both LHRH and transferrin receptors are attached to the carrier particles by conjugation. Both LHRH and transferrin moieties are used with both the nano- and microparticles, each of which includes as a therapeutic agent budesonide, celecoxib, Flt23K plasmid, or a combination of any or all of the foregoing agents. The targeting moieties include deslorelin, an LHRH analog having the N-terminal domain of LHRH and a D-amino acid substitution at the sixth amino acid residue, transferrin, a transferrin variant having the C-terminal domain of transferrin, an LHRH antibody, and a transferrin antibody. Of particular interest are the nanoparticle carriers of budesonide that are targeted with either deslorelin or the LHRH analog having the N-terminal domain of LHRH and a D-amino acid substitution at the sixth amino acid residue, which are referred to as Formulation 1 (deslorelin) and Formulation 2 (LHRH analog).

The carrier particles are conjugated to the targeting moiety by covalent conjugation of the protein to the carboxylate surface functionality on the particles using carbodiimide. Briefly, 5 ml of 2 mg/ml NP suspension in 3(N-Morpholino) propanesulfonic acid (MOPS) buffer is added dropwise to 5 ml of 200 μg/ml protein solution. The mixture is allowed to react at room temperature for 15 min. Carbodiimide (4 mg) is added to the reaction mixture and the pH adjusted to 7.3-7.4. The reaction mixture is allowed to incubate at room temperature for 2 hours with vortexing. After 2 hours, the reaction is quenched by the addition of 100 mM glycine. The conjugated particles are separated from unreacted protein by dialyzing across a membrane with 50,000 molecular weight cut off (Spectra/Por, Spectrum Laboratories, CA). Compositions of the targeted carrier particles are formulated by suspending particles in assay buffer (pH 7.4), containing 1.14 mM $CaCl_2$, 1.2 mM $MgSO_4$, 3 mM KCl, 0.4 mM $KH_2PO_4$, 25 mM $NaHCO_3$, 10 mM glucose, 122 mM NaCl, and 10 mM HEPES (N-2-hydroxyethylpiperazine-N'-2-ethanesulphonic acid), creating a solution of particles with 10% wt/wt of cyclodextrin as a solubilizing agent, or by suspending the particles in a vehicle such as PBS (pH 7.4). Eyedrops may be formulated using any of these compositions.

Example 21

Ophthalmic Administration of Therapeutic Compositions in a Mouse Model

A newborn mouse animal model of neovascularization conditions and diseases such as age-related macular degeneration, diabetic retinopathy, and oxygen-induced blindness demonstrates the utility and surprisingly advantageous topical, ophthalmic administration of a VEGF inhibitor using the targeted carrier particles of the present invention. Newborn mice on postnatal day 7 are kept in high oxygen (75 percent) from day 7 to 11, and then are brought to normal room air on day 12. A relative hyperoxia results, and retinal neovascularization is seen in 100 percent of the exposed animals by day 17. Some of the animals (n=9) initially exposed to the oxygen cycle receive Formulation 1 eyedrops four times a day in the right eye on days 14-17 (four days) (Group I). Some animals (n=9) receive the same eyedrops, administered similarly, on days 13-17 (Group II). In another group of animals (n=9) (Group III), the eyedrops are instilled in the right eye and normal saline is instilled in the left eye (control). Groups IV (n=9) and V (n=9) receive Formulation 2 eyedrops according to the same procedure as Groups I and III. Animals are sacrificed on day 17. Newborn animals kept in room air only for 17 days may serve as controls. Eye tissue is processed for paraffin embedding sections, which are stained for nuclei with DAPI (diamidinophenylindole). Sections can be examined under a fluorescence microscope and nuclei on the vitreous side of the inner limiting membrane of the retina, representing microvascular cells, are counted in each section using a masked protocol. Numerous neovascular tufts may be seen protruding from the retina into the vitreous in animals exposed to hyperoxia (75 percent oxygen) followed by room air. Quantification reveals about 50 neovascular nuclei per section in experimental animals (without drug treatment) compared to controls (less than 1 neovascular nuclei per section). Animals treated with Formulations 1 and 2 eyedrops show a decrease in neovascular nuclei, resulting from a decrease in the activity of VEGF in the retina.

In another study, animals are treated with hyperoxia conditions, as described above. Then, Formulations 1 and 2 are separately introduced into the animals via intraocular injection. A course of injection on days 12, 14 and 16 results in a reduction in neovascularization in the same animal model.

Example 22

Ophthalmic Administration of Therapeutic Compositions in Rabbits

A study in rabbits examines the $^{14}C$ activity in ocular tissues and blood plasma following administration of a topical ophthalmic composition containing the targeted carrier particles of Example 20, including Formulations 1 and 2. The ocular tissues examined are the aqueous humor, cornea, iris and ciliary body, vitreous humor, retina and choroid, and the sclera. The study has three step-wise phases: phase 1 examines $^{14}C$ activity at 20 minutes, 40 minutes, 1 hour and 2 hours post-administration, phase 2 examines $^{14}C$ activity at 3 and 4 hours post-administration, and phase 3 examines $^{14}C$ activity at 6 and 8 hours post-administration. Initially, 6 rabbits (12 eyes) are examined at each time point. To control bias, animals are randomly enrolled in the study. Within an animal room (total capacity 54 rabbits), each rabbit eligible for enrollment in the study is randomly assigned a temporary sequential number. Rabbits are selected for use in the study in sequential order of temporary number.

This study uses female New Zealand White rabbits that weigh approximately 1.8 to 2.8 kg upon arrival and are approximately 9 weeks old. Each rabbit is identified with an ear tag bearing a unique number, and the rabbit's cage also bears the same number. Rabbits are acclimated to the laboratory environment in a specified quarantine area for a minimum of two weeks before being used in the study. Rabbits receive a daily ration of commercially available feed and tap water ad libitum. Rabbit health is monitored daily. Rabbits are placed in temporary housing after instillation of 14C-labeled test material. The rabbits are anesthetized and euthanized at the conclusion of the in vivo experimental period.

The test material is administered with a positive displacement micropipettor. The average mass and standard deviation of dispensed test material is estimated. Approximately 25 mg of test material is instilled into the lower cul-de-sac of both eyes. The material is placed into the eye by gently pulling the lower lid away from the globe to form a cup into which the material will be instilled. Rabbits are anesthetized with an intramuscular injection of ketamine and xylazine (0.4 ml/kg each) approximately 20 minutes prior to the scheduled collection time of aqueous humor. Aqueous humor is collected from both eyes according to methods known in the art. Aqueous humor is collected from OD, then OS. A 0.5 ml syringe with a fixed 28G×½" needle is used, and an ophthalmic solution of 0.5 percent proparacaine hydrochloride is administered prophylactically to all eyes without testing for corneal reflex. Eyes are irrigated with commercially available Eye Irrigating Solution. Both eyes are enucleated starting with OD. Tissues collected include: bulbar conjunctiva, cornea, iris, sclera, vitreous humor, and retina. Tissues are placed into preweighed scintillation vials. All scintillation vials are capped and weighed. Immediately after the aqueous humor has been collected from both eyes, approximately 5 ml of blood is withdrawn by intracardiac puncture. Blood is collected into a heparinized tube.

For the bulbar conjunctiva, cornea, iris, sclera and retina/choroid, 100 µl of reverse osmosis (RO) purified water is added to each sample and the sample vortexed. 250 µl of hyamine hydroxide is added to each vial and the sample again vortexed. For the vitreous humor, 100 µl of reverse osmosis (RO) purified water is added to each sample and the sample vortexed. 750 µl of hyamine hydroxide is added to each vial and the sample again vortexed. The samples are then incubated at 55 degrees Celsius in a water bath until solubilized (approximately 1-4 hours). After solubilization is complete, the samples are vortexed again, and 6 ml of CytoScintES® scintillation cocktail is added to each sample. Solubilized samples are immediately mixed with the scintillation cocktail by repeatedly inverting the capped vial. Vigorous shaking is avoided.

For the aqueous humor, 6 ml of CytoScintES® scintillation cocktail is added directly to each aqueous humor sample and mixed by repeatedly inverting the capped vial. There is no need to solubilize the aqueous humor sample. Blood samples are kept in a cooler containing ice packs to keep them cold until separation. Plasma is separated from the red blood cells by centrifugation at 4 degrees Celsius and 1200-1500 g for 15 minutes. Immediately after centrifuging, 1 ml of the plasma is pipetted from the tube and placed into a 20 ml scintillation vial. 18 ml of CytoScintES® scintillation cocktail is added directly to each plasma sample and mixed by repeatedly inverting the capped vial. All samples are dark-adapted overnight before counting in a Beckman LS 3801. Results reveal that the therapeutic agents reach the intraocular and retinal tissues shortly after topical administration to the eye; and are maintained in the intraocular retinal tissue at therapeutically effective levels for at least 6 hours.

Example 23

Ophthalmic and Intranasal Administration of Therapeutic Compositions in Rats

A study in rats examines the tissue levels of therapeutic agents after subconjunctival injection of ophthalmic compositions containing the targeted carrier particles of Example 20 (the "test solutions"), including Formulations 1 and 2, and after intranasal delivery of compositions containing the targeted carrier particles of Example 20 (the "test solutions"), including Formulations 1 and 2. Sprague-Dawley rats weighing 180 to 200 g are anesthetized with an intraperitoneal injection of pentobarbital sodium (40 mg/kg). After this, 50 or 75 µl of each test solution is injected into the subconjunctival space of one eye (ipsilateral) by 27-gauge needle. The other eye (contralateral) will serve as the control. At the end of 1, 3, 7, and 14 days the animals are killed, the eyes are enucleated, frozen immediately, and stored at −80° C. The frozen eyes are dissected, and the ocular tissues including retina, vitreous, lens, and cornea are isolated and the drug levels estimated with a HPLC method. Similarly, rats enrolled in the nasal study are immobilized and 50 or 75 µl of each test solution is sprayed into the nasal cavity of one nostril. At the end of 1, 3, 7, and 14 days the animals are killed, the nasal tissues are isolated, and the drug levels estimated with a HPLC method.

The isolated ocular or nasal tissues are homogenized in 200 µl of PBS buffer (Tissue Tearor; Fisher Scientific). To the homogenate, 2.5 µl of a 40-µg/mL solution of celecoxib is added as an internal standard and mixed thoroughly. Methylene chloride (2 mL) is added and mixed thoroughly at room temperature for 5 minutes. The resultant solution is evaporated to dryness under nitrogen, and the dried residue is reconstituted with 150 µl acetonitrile:water (70:30) mixture. This reconstituted solution is vortexed for 1 minute and centrifuged at 12,000 g for 5 minutes, and 100 µl of the supernatant is injected on to an HPLC system (Waters, Milford, Mass.) equipped with a pump (TM616; Waters), a controller (600S; Waters), an autoinjector (717plus; Waters), and a PDA detector (996; Waters). The peak areas are integrated on computer (Millennium software, ver. 2.15.01; Millennium Software, Torrance, Calif.). The drugs are separated with a 25-cm long C-18 column (Discovery; Supelco, Emeryville, Calif.) with a particle diameter of 5 µm and a pore size of 10 nm. The mobile phase for the assay consists of acetonitrile and aqueous buffer mixture (70:30 vol/vol). The buffer is 0.1% acetic acid in water at pH 3. The aqueous samples obtained from drug loading, and in vitro release studies are analyzed under the same HPLC conditions.

Example 24

Pulmonary Administration of Therapeutic Compositions in Rats

A study in rats examines the tissue levels of therapeutic agents after pulmonary administration of compositions containing the targeted carrier particles of Example 20 (the "test solutions"), including Formulations 1 and 2. Materials include Sprague Dawley female rats 225-300 g (Charles River, Raleigh, N.C.), fiber optic laryngoscope (Custom Manufactured, EPA, Research Triangle Park, N.C.), heating blanket thermostatically controlled via rectal probe (Harvard Apparatus, Cambridge, Mass.), siliconized Eppendorf tubes, Helix Medical Silicone Tubing Spray instillator (Penn Century, Philadelphia, Pa.), ketamine (100 mg/ml) and acepromazine (10 mg/ml) (Fort Dodge Laboratories Inc. Fort Dodge, Iowa), xylazine (100 mg/ml) (Vedco Inc. St. Joseph. MO), heparin 1000 units/mil (Elkins-Sinn, Inc. Cherry Hill, N.J.), and 0.9% Sodium Chloride Injection USP sterile solution (Baxter Healthcare Corporation, Deerfield, Ill.).

A cocktail of anesthetic solution is prepared containing Xylazine (100 mg/ml) Ketamine (100 mg/ml): Acepromazine (10 mg/ml) in the proportion of 1:3:1. 0.9% Sodium Chloride Injection USP containing Heparin 20 units/ml Insulin is dissolved in pH=3 distilled water titrated with 0.01 N HCl. When solution is clear, pH 7 distilled water is added. Then, pH is brought to 7.5 with 0.01 NaOH. Each rat is weighed and identified using an indelible marker and is anesthetized by intraperitoneal injection of ketamine: Xylazine: Acepromazine cocktail, at 80 mg/kg, 10 mg/kg and 2.0 mg/kg, respectively and returned to its cage. The rat is transferred to the surgical bench and placed on a heating blanket thermostatically controlled via rectal probe, once deep anesthesia is achieved. The right jugular vein of each rat is catheterized using silicone tubing and the patency of the catheter is confirmed by slowly flushing the cannula with 200 μl heparin saline and then withdrawing 100 μl of blood. The cannula is then cleared with 200 μl of heparinized saline solution. An endotracheal tube is inserted using a fiber optic laryngoscope. The syringe (Hamilton syringe) of the instillator is attached to the endotracheal tube and used to instill solution (100 μl) in the airways. The endotracheal tube is removed following administration, and the breathing rate is monitored throughout the remainder of the study. Blood samples (500 μl) are withdrawn at 0, 10, 30, 60, 90, 120 and 180 min and the cannula flushed with approximately 200 μl of heparinized saline solution. The blood is collected in 1 ml tuberculin syringes (containing 100 μl heparin 20μ/ml) placed directly into microcentrifuge tubes. Blood samples are immediately centrifuged at 10 000 rpm for 4 min. Aliquots of approximately 30 μl are transferred to labeled siliconized 1 ml Eppendorf tubes and kept on ice until completion of the study.

All publications and patents mentioned in the above specification are herein incorporated by reference. The above description, drawings and examples are only illustrative of preferred embodiments which achieve the objects, features and advantages of the present invention. It is not intended that the present invention be limited to the illustrative embodiments. Any modification of the present invention which comes within the spirit and scope of the following claims should be considered part of the present invention.

What is claimed is:

1. A composition for use in treating or preventing ophthalmic disorders in a mammal by administration to the eye, comprising:
   a plurality of poly(lactide) carrier particles comprising a therapeutically effective amount of a therapeutic agent;
   a plurality of ocular targeting moieties conjugated to the outer surface of said carrier particles, wherein said ocular targeting moieties are LHRH-receptor targeting moieties, and wherein the therapeutic agent and the ocular targeting moieties are not the same; and
   a plurality of transferrin-receptor-targeting moieties conjugated to the outer surface of said carrier particles.

2. The composition of claim 1, wherein said carrier particles are nanoparticles.

3. The composition of claim 1, wherein said poly(lactide) is poly(lactide-co-glycolide).

4. The composition of claim 1, wherein said therapeutic agent is an anti-VEGF agent or anti-angiogenic agent.

5. The composition of claim 1, wherein said therapeutic agent is a glaucoma therapeutic agent.

6. The composition of claim 1, wherein said therapeutic agent is a dry eye therapeutic agent.

7. The composition of claim 1, wherein said therapeutic agent is an antibiotic.

8. The composition of claim 1, wherein said therapeutic agent is an anti-inflammatory.

9. The composition of claim 1, wherein said therapeutic agent is a nucleic acid based therapeutic agent selected from the group consisting of oligomers, siRNAs, plasmids, and aptamers.

10. The composition of claim 1, wherein said carrier particles further comprise a second therapeutic agent.

11. The composition of claim 1, wherein at least one of said ocular targeting moieties is deslorelin.

12. The composition of claim 1, wherein at least one of said ocular targeting moieties is an LHRH-receptor antibody.

13. The composition of claim 1, wherein at least one of said plurality of transferrin-receptor-targeting moieties is transferrin.

14. The composition of claim 1, wherein at least one of said plurality of transferrin-receptor-targeting moieties is a transferrin-receptor antibody.

15. A method of treating or preventing ophthalmic disorders in a mammal, comprising administering to the eye a composition capable of delivering a therapeutically effective amount of a therapeutic agent, wherein said composition comprises a plurality of poly(lactide) carrier particles comprising a therapeutically effective amount of a therapeutic agent, a plurality of ocular targeting moieties conjugated to the outer surface of said carrier particles, wherein said ocular targeting moieties are LHRH-receptor targeting moieties, and a plurality of transferrin-receptor-targeting moieties conjugated to the outer surface of said carrier particles, and wherein the therapeutic agent and the ocular targeting moieties are not the same.

16. The method of claim 15, wherein said administration is topical administration.

17. The method of claim 15, wherein said administration is by injection.

18. The method of claim 15, wherein said ophthalmic disorder is a disorder of the anterior segment of the eye.

19. The method of claim 18, wherein said disorder of the anterior segment of the eye is selected from the group consisting of dry eye, glaucoma, allergic conditions, inflammatory conditions of the anterior segment and cornea, allergic conditions of the anterior segment and cornea, infectious conditions of the anterior segment and cornea, and corneal angiogenesis.

20. The method of claim 15, wherein said ophthalmic disorder is a disorder of the posterior segment of the eye.

21. The method of claim 20, wherein said disorder of the posterior segment of the eye is selected from the group consisting of macular degeneration, diabetic retinopathy, inflammatory conditions of the posterior segment, infectious conditions of the posterior segment, neurodegenerative disease, and vascular disease of the posterior segment.

22. The method of claim 15, wherein said administration is intravenously.

* * * * *